US011566133B2

(12) United States Patent
Enrione Cáceres et al.

(10) Patent No.: US 11,566,133 B2
(45) Date of Patent: Jan. 31, 2023

(54) GELATIN POLYMER DERIVED FROM NATURAL SOURCES OF COLD-ADAPTED MARINE SPECIES AND USES THEREOF

(71) Applicants: UNIVERSIDAD DE LOS ANDES, Santiago (CL); CELLS FOR CELLS S.A., Santiago (CL)

(72) Inventors: Javier Enrione Cáceres, Santiago (CL); Paulo Díaz-Calderón, Santiago (CL); Alessandro Zaupa, Santiago (CL); Juan Pablo Acevedo Cox, Santiago (CL)

(73) Assignees: UNIVERSIDAD DE LOS ANDES, Santiago (CL); CELLS FOR CELLS S.A., Santiago (CL)

( * ) Notice: Subject to any disclaimer, the term of this patent is extended or adjusted under 35 U.S.C. 154(b) by 0 days.

(21) Appl. No.: 16/310,780

(22) PCT Filed: Jun. 19, 2017

(86) PCT No.: PCT/IB2017/053637
§ 371 (c)(1),
(2) Date: Dec. 17, 2018

(87) PCT Pub. No.: WO2017/216780
PCT Pub. Date: Dec. 21, 2017

(65) Prior Publication Data
US 2019/0194460 A1   Jun. 27, 2019

(30) Foreign Application Priority Data
Jun. 17, 2016   (EP) .................................... 16175153

(51) Int. Cl.
*C08L 89/06* (2006.01)
*C07K 14/78* (2006.01)
*C08H 1/00* (2006.01)
*C08J 3/075* (2006.01)
*C08K 5/101* (2006.01)
*C07K 14/46* (2006.01)
*B33Y 70/00* (2020.01)

(52) U.S. Cl.
CPC .............. *C08L 89/06* (2013.01); *C07K 14/78* (2013.01); *C08H 1/00* (2013.01); *C08J 3/075* (2013.01); *C08K 5/101* (2013.01); *B33Y 70/00* (2014.12); *C07K 14/461* (2013.01); *C08J 2389/06* (2013.01); *C08L 2312/00* (2013.01)

(58) Field of Classification Search
CPC ........ C07K 14/461; C07K 14/78; C08H 1/00; C08K 5/101; C08L 2312/00; C08L 89/06
See application file for complete search history.

(56) References Cited

U.S. PATENT DOCUMENTS

| 2008/0287565 A1 | 11/2008 | Liska et al. |
| 2012/0220691 A1 | 8/2012 | Shreiber et al. |
| 2018/0303878 A1 | 10/2018 | Khoury et al. |
| 2018/0304502 A1 | 10/2018 | Acevedo et al. |
| 2019/0038675 A1 | 2/2019 | Khoury et al. |
| 2019/0365804 A1 | 12/2019 | Khoury et al. |

FOREIGN PATENT DOCUMENTS

| EA | 007463 B1 | 10/2006 |
| JP | H10-195169 A | 7/1998 |
| RU | 2 124 537 C1 | 1/1999 |
| RU | 2 564 824 C1 | 10/2015 |
| WO | 98/55161 A1 | 12/1998 |
| WO | 2008/103045 A1 | 8/2008 |
| WO | 2008/103046 A1 | 8/2008 |
| WO | 2009/153750 A2 | 12/2009 |
| WO | 2010/125163 A1 | 11/2010 |
| WO | 2014/147415 A1 | 9/2014 |

OTHER PUBLICATIONS

Teramoto et al. "Preparation and Mechanical Properties of Photo-Crosslinked Fish Gelatin/Imogolite Nanofiber Composite Hydrogel" Materials 5:2573-2585. (Year: 2012).*
Yu et al. "Synthesis, properties, and biomedical applications of gelatin methacryloyl (GelMA) hydrogels" Biomaterials 73:254-271. (Year: 2015).*
Chiou et al. "Cold water fish gelatin films: Effects of cross-linking on thermal, mechanical, barrier, and biodegradation properties" European Polymer Journal 44:3748-3753. (Year: 2008).*
Cole, CGB "Gelatin" Encyclopedia of Food Science and Technology, 2nd Edition, New York: John Wiley & Sons, p. 1183-1188. (Year: 2000).*
Pereira et al. "3D bioprinting of photocrosslinkable hydrogel constructs" J. Applied Polymer Sci. 132 (Year: 2015).*
Ofori R "Preparation of Gelatin from Fish Skin by an Enzyme Aided Process" Master Thesis, McGill University. (Year: 1999).*
Chiou et al. "Effect of drying temperature on barrier and mechanical properties of cold-water fish gelatin films" J. Food Engin. 95: 327-331. (Year: 2009).*
Amudeswari et al., "Hydrogels Based on Graft Copolymers of Collagen Synthesis," *Journal of Applied Polymer Science* 32(5):4939-4944, 1986.
Brinkman et al., "Photo-Cross-Linking of Type I Collagen Gels in the Presence of Smooth Muscle Cells: Mechanical Properties, Cell Viability, and Function," *Biomacromolecules* 4(4):890-895, 2003.
Chiou et al., "Rheological and mechanical properties of cross-linked fish gelatins," *Polymer* 47(18):6379-6386, 2006.

(Continued)

*Primary Examiner* — Sudhakar Katakam
*Assistant Examiner* — Zachary J Miknis
(74) *Attorney, Agent, or Firm* — Seed IP Law Group LLP

(57) ABSTRACT

The present invention refers to a composition comprising a solution which in turn comprises an amino acidic chain gelatin polymer derived from natural sources of cold-adapted marine species, at a concentration from 1% to 20% (w/v), which optionally further comprises a polymerizing initiator such as a photoinitiator, and is chemically functionalized to become reactive to polymerization or crosslinking in presence of free radicals. This composition is especially useful for 3D printing, extrusion systems (additive fabrication), spray systems, casting, micro- and nano fibers fabrication systems (electrospinning, solution blow spinning) or microfluidics.

10 Claims, 31 Drawing Sheets

(56) References Cited

OTHER PUBLICATIONS

Gómez-Guillén et al., "Functional and bioactive properties of collagen and gelatin from alternative sources: A review," 25(8):1813-1827, 2011.

Karim et al., "Fish gelatin: properties, challenges, and prospects as an alternative to mammalian gelatins," *Food Hydrocolloids* 23(3):563-576, 2009.

Nichol et al. "Cell-laden microengineered gelatin methacrylate hydrogels," *Biomaterials* 31(21):5536-5544, 2010.

Yi et al., "Influence of Transglutaminase-Induced Cross-Linking on Properties of Fish Gelatin Films," *Journal of Food Science* 71(9):E376-E383, 2006.

*Pharmaceutical Polymer Materials*, eds. Zheng Junmin, China Medical Science and Technology Press, pp. 175-177, published Jan. 1, 2009, URL= http://img.duxiu.com/n/jpgfs/book/base/12186131/56f8d0fa3d9c410a8bcee8a6048b7520/ca659bd220fda5d0fbf20fc637ea87a0.shtml?uf=1&t=4&t, retrieved on Dec. 6, 2020, 8 pages. (English abstract).

Avena-Bustillos et al., "Gelation, Oxygen Permeability, and Mechanical Properties of Mammalian and Fish Gelatin Films," *J. Food Sci.* 76(7):E519-E524, 2011.

Leuenberger, "Investigation of viscosity and gelatin properties of different mammalian and fish gelatins," *Food Hydrocolloids* 5(4):353-361, 1991.

\* cited by examiner

GELATIN POLYMER DERIVED FROM NATURAL SOURCES OF COLD-ADAPTED MARINE SPECIES AND USES THEREOF

TECHNICAL FIELD OF THE INVENTION

The present invention refers to the biomedical field and the alimentary sector, in particular it refers to a composition comprising a solution which in turn comprises an amino acidic chain gelatin polymer derived from natural sources of cold-adapted marine species, at a concentration from 1% to 20% (w/v), which optionally further comprises a photoinitiator or any other type of radical-derived initiators and is chemically functionalized to become reactive to polymerization or crosslinking in presence of free radicals. Such composition is particularly suitable for new bio fabrication technologies for use in the biomedical and alimentary fields.

BACKGROUND OF THE INVENTION

In the biomedical field, new bio fabrication technologies allow the production of biomaterials, such as scaffolds, beads, engineered tissues, devices and micro-devices for therapeutic or diagnostic purposes. Some of these (bio fabrication or biomanufacturing) technologies comprise the use of techniques such as 3D bio-printing, extrusion systems (additive fabrication), spray systems, casting, micro- and nano fibers fabrication systems (electrospinning, solution blow spinning) and microfluidics, amongst others. In food science some of these technologies are also used, in particular extrusion and spray systems.

The use of these techniques or technologies requires the control of the state of aggregation and polymerization or crosslinking of the biomaterial. In this sense, biomaterials are initially handled in its liquid state and then through the control of polymerization/crosslinking the final product is obtained at a more solid state. In this regard, high-performance functioning of these technologies is highly dependent on the rheological properties of the biomaterial at the liquid state and the level of control that the system has over the transition into a more solid state, taking into account that functionality of the final product in any given particular application is dependent on the mechanical, physicochemical and biological properties of the biomaterial at the solid state. In other words, high-performance of these technologies requires specific rheological properties before polymerization/crosslinking, control of polymerization/crosslinking and mechanical properties of the polymerized or crosslinked biomaterial.

Indeed, high precision biomanufacturing technologies (such as inkjet bioprinting, spraying-coating and microfluidic derived systems) require compositions enabling the control of the state of polymerization/crosslinking of the biomaterial, with specific rheological properties in order to allow formation of very small drops (pL) or to avoid high flow resistance within micro-sized channels. Thus, the ideal composition will have specific rheological properties (resulting for instance in good jetting capability when conducting 3D bioprinting) prior to cross-linking/polymerization and good mechanical properties once the biomaterial is in a solid state. Ideal compositions will have prior to the cross-linking/polymerization step: Newtonian fluid behavior, a viscosity between 25-10 cP and stability at different share rates and/or temperatures. Preferably the ideal composition will also have low surface tension (25-30 mN/m).

The biomedical field demands a number of physicochemical and biological properties that influences the results of the therapeutic or diagnostic applications. Some of these properties are related to control of the microenvironment of the cellular components and a direct interaction of the biomaterial with the cells that derived in specific biological responses and active remodeling of the biomaterial in response to cell biological activities. These properties are also listed as control delivery of biologically meaningful elements, cytocompatibility, bioactivity and biodegradability. On the other hand, in the alimentary field, there is a need for specialized and cost-efficient technologies for deposition of food coatings such as spray systems or beads fabrication for supplementation of encapsulated vitamin or other active compounds.

Unfortunately, both of these fields are limited in performance due to the suboptimal rheological nature and control of polymerization/crosslinking of the majority of the biomaterials used thus far.

In recent years there has been an increasing interest in finding gelatin sources alternative to mammalian gelatins (e.g. porcine and bovine). In particular, fish gelatins have been proposed as an alternative but an important challenge to be overcome are its inferior rheological properties. This limitation has been attributed to the lack of proline rich regions of the collagen/gelatin of cold water fish (Karim A A et al: Food Hydrocolloids 2009, 23(3), 563-576; Gomez-Guillén M C et al: Food Hydrocolloids 2011, 25(8) 1813-1827).

With the aim of providing fish gelatin polymers with improved mechanical properties the induction of intra- and inter-molecular cross-linking has previously been reported. Chiou B S et al: Polymer 2006, 47(18), 6379-6386 describes traditional gelatin cross-linking methods adding cross-linking agents (i.e. glutaraldehyde and/or genipin) to the gelatin containing composition. The time required to obtain optimal cross-linking with this strategy is in the range from hours to days.

Besides, J. B. Yi et al: Journal of Food Science 2006, 71(9), E376-E383 describes fish gelatin cross-linking using enzymatic transglutaminase (i.e. MTGase). This document teaches that the time required for the obtaining of a gel with suitable viscosity through cross-linking with enzymatic transglutaminase is in the range of minutes.

Accordingly, it exists the need to obtain a gelatin composition with suitable rheological properties for high precision biomanufacturing technologies which further to cross-linking results in a composition with good mechanical (compressive and/or tensile) properties, preferably, wherein the cross-linking time is decreased to the range of seconds to a few minutes, for instance a maximum of 5 minutes.

Therefore, new biomaterials for use in these technologies are urgently needed. Consequently, there is still a need for novel highly bioactive biomaterials that can create structurally complex scaffolds with the desired geometry, biological and physical properties for optimal application in biomedicine and food.

BRIEF DESCRIPTION OF THE INVENTION

In the present invention, we proposed the use of gelatin polymers derived from natural sources of cold-adapted marine species, such as salmon gelatin, with introduced chemical substituents, such as methacryloyl groups, in the amino acidic sequence as new photo-cross-linkable biomaterials with unique properties for the biomedical and food industries, properties that derived from its cold-adapted nature. A distinctive feature of cold-adapted organisms such as Salmon is their typically more structural flexibility of proteins. In this sense, salmon gelatin in solution at 10% w/v has shown a 4 fold lower viscosity than bovine gelatin. This property allows the use of specialized fabrication technologies such as multijet or polyjet technology for high resolution 3D printing or microfluidic derived techniques which require biomaterials with low viscosity and rapid polymerization. Our initial working hypothesis stated that higher flexibility of salmon gelatin at the molecular level, beside the rheological benefit, could enhance the catalytic efficiency of MMP (metalloproteinases). This would improve cells migration/invasion, angiogenesis and tissue integration in vivo, in spite of the undesired impairment of the mechanical toughness of the photo-fabricated hydrogel based on this new biomaterial. However, in contrast, we have observed the unexpected fact that although the increased catalytic turnover of MMP due to higher flexibility of salmon gelatin, and that the molecular flexibility of hydrogel based on modified salmon gelatin is higher than bovine, the mechanical properties of salmon hydrogel showed higher young modulus than bovine. In addition, hydrogels of photo-crosslinkable salmon gelatin have shown higher levels of vascularization and tissue integration when combined with mesenchymal stem cells, HUVECs and implanted subcutaneously in mice models. Moreover, gelatin polymers derived from natural sources of cold-adapted marine species, such as salmon gelatin, with introduced chemical substituents, such as methacryloyl groups, in the amino acidic sequence as new photo-cross-linkable biomaterials, constitute magnificent compositions for food processing and preservations.

Therefore, in a first aspect the present invention refers to a composition comprising a solution which in turn comprises an amino acidic chain gelatin polymer derived from natural sources of cold-adapted marine species, at a concentration from 1% to 20% (w/v), which optionally further comprises a polymerizing initiator such as a photoinitiator, and is chemically functionalized to become reactive to polymerization or crosslinking in presence of free radicals. Preferably, the composition comprises an amino acidic chain gelatin polymer at a concentration from 5% to 20% (w/v). More preferably, the composition further comprises a surfactant. Still more preferably, the amino acidic chain gelatin polymer of the composition is functionalized with a chemical agent selected from the group consisting of methacryloyl groups, acryloyl groups or any functional group or a moiety capable of mediating formation of a polymer or reaction with a surface or other molecule. Functional groups include the various radicals and chemical entities taught herein, and include alkenyl moieties such as acrylates, methacrylates, dimethacrylates, oligoacrylates, oligomethacrylates, ethacrylates, itaconates or acrylamides. Further functional groups include aldehydes. Other functional groups may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrile and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene, and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid, and styrene carboxylic acid. Suitable polyethylenically unsaturated monomers include butadiene, isoprene, allylmethacrylate, diacrylates of alkyl diols such as butanediol diacrylate and hexanediol diacrylate, divinyl benzene, and the like. It is preferred that the amino acidic chain is functionalized with methacryloyl groups.

In a preferred embodiment of the first aspect of the invention, the degree of functionalization of the acidic side chain of the gelatin polymer with a chemical agent capable of polymerizing or crosslinking in presence of free radicals is from 10% to 100%, preferably from 20% to 100%, more preferably from 30% to 100%, more preferably from 40% to 100%, more preferably from 50% to 100%, more preferably from 60% to 100%, more preferably from 70% to 100%, more preferably from 80% to 100%, more preferably from 90% to 100%, of the lysine residues. In a more preferred embodiment the degree of functionalization is about 90%.

In another preferred embodiment of the first aspect of the invention, the surfactant is selected from the group consisting of SDS, tween 20, Kolliphor® P 188 (Sigma-Aldrich), or the like.

In another preferred embodiment of the first aspect of the invention, the polymerizing initiator is a photoinitiator such as Irgacure® 2959 [(Ciba specialty chemical now BASF Resins], preferably in a concentration of about 0.01% to 5% (w/v). It is noted that in the context of the present invention, a "polymerizing initiator" refers to any substance that can initiate polymerization of monomers or macromers by, for example, free radical generation. The polymerizing initiator often is an oxidizing agent. Exemplary polymerization initiators include those which are activated by exposure to, for example, electromagnetic radiation or heat. Polymerization initiators can also be used and are described, e.g., in U.S. Patent Application Publication No. 2010/0137241, which is incorporated by reference in entirety.

In another preferred embodiment of the first aspect of the invention, the solution is pre-treated with temperature of from −5° C. to 15° C., prior to cross-linking, during a time interval of from 1 msec to 4 hours, preferably from 1 second to 4 hours, more preferably from 1 minute to 4 hours, preferably from 10 minutes to 4 hours, more preferably from 30 minutes to 4 hours, more preferably from 45 minutes to 4 hours, still more preferably from about 1 hr to about 4 hrs, still more preferably from about 1 hr to about 3 hrs.

In another preferred embodiment of the first aspect of the invention, the gelatin polymer is derived from the genus *Salmo* or *Oncorhynchus*, preferably the gelatin polymer is derived from salmon.

A second aspect of the invention, refers to a process to manufacture a composition comprising a solution which in turn comprises an amino acidic chain gelatin polymer derived from natural sources of cold-adapted marine species, preferably from the genus *Salmo* or *Oncorhynchus*, at a concentration from 1% to 20% (w/v), preferably from 5 to 20% (w/v), which optionally further comprises a polymerizing initiator such as a photoinitiator and is chemically functionalized to become reactive to polymerization or crosslinking in presence of free radicals, comprising the following steps:

a. Obtaining an amino acidic chain gelatin polymer derived from natural sources of cold-adapted marine species, preferably from the genus *Salmo* or *Oncorhynchus*, and dissolving it in a solvent to a final concentration between 1% and 20% (w/v), preferably from 5 to 20% (w/v);
b. Chemically modifying the primary structure of the amino acidic chain gelatin polymer of step a), by adding a chemical agent capable of becoming reactive to polymerization or crosslinking in presence of free radicals to the solution of step a);
c. Removing all unreacted chemically agents from the solution of step b); and
d. Optionally adding a polymerizing initiator such as a photoinitiator and/or a surfactant to the solution.

In a preferred embodiment of the second aspect of the invention, the amino acidic chain is functionalized with a chemical agent selected from the group consisting of methacryloyl groups or acryloyl groups.

In another preferred embodiment of the second aspect of the invention, the process comprises the following steps:
a. Obtaining an amino acidic chain gelatin polymer derived from natural sources of cold-adapted marine species, preferably from the genus *Salmo* or *Oncorhynchus*, and dissolving it in a solvent to a final concentration between 1% and 20% (w/v), preferably from 5 to 20% (w/v);
b. Chemically modifying the primary structure of the amino acidic chain gelatin polymer of step a), by adding methacrylic anhydride to the solution of step a);
c. Removing all unreacted methacrylic anhydride from the solution of step b);
d. Optionally adding a radical-derived initiator such as photoinitiator and/or a surfactant;
e. optionally filtering and freeze drying the resultant composition from step c) or d) if applicable.

In another preferred embodiment of the second aspect of the invention, the process further comprises exposing the solution comprising the chemically modified amino acidic chain and a photoinitiator to light, visible, UV light or infrared depending on the nature of the photoinitiator, to provide a crosslinked composition.

A third aspect of the invention refers to the solution obtained or obtainable by any of the processes of the second aspect of the invention.

A fourth aspect of the invention refers to a crosslinked composition obtained or obtainable by exposing the solution comprising the chemically modified amino acidic chain as defined in the second aspect of the invention to a polymerizing initiator, more particularly to a photoinitiator to light, visible, UV light or infrared depending on the nature of the photoinitiator, to provide a cross-linked composition.

A fifth aspect of the invention refers to the use of a solution which in turn comprises an amino acidic chain gelatin polymer derived from natural sources of cold-adapted marine species, preferably from the genus *Salmo* or *Oncorhynchus*, at a concentration from 1% to 20% (w/v), preferably from 5 to 20% (w/v); for 3D printing, extrusion systems (additive fabrication), spray systems, casting, micro- and nano fibers fabrication systems (electrospinning, solution blow spinning) or microfluidics.

A sixth aspect of the invention refers to the use of a composition as defined in the first aspect of the invention or as defined in the third aspect of the invention, for 3D printing, extrusion systems (additive fabrication), spray systems, casting, micro- and nano fibers fabrication systems (electrospinning, solution blow spinning) or microfluidics.

A seventh aspect of the invention refers to the use of a composition as defined in the first aspect of the invention or as defined in the third or fourth aspects of the invention, for the production of scaffolds, beads, engineered tissues or devices and micro-devices, suitable for therapeutic or diagnostic purposes.

An eighth aspect of the invention refers to the use of a composition as defined in the first aspect of the invention or as defined in the third or fourth aspects of the invention, for food coating.

A ninth aspect of the invention refers to the use of a solution which in turn comprises an amino acidic chain gelatin polymer derived from natural sources of cold-adapted marine species, preferably from the genus *Salmo* or *Oncorhynchus*, at a concentration from 1% to 20% (w/v), preferably from 5 to 20% (w/v); for food coating or for the production of scaffolds, beads, engineered tissues or devices and micro-devices, suitable for therapeutic or diagnostic purposes.

DESCRIPTION OF THE INVENTION

Definitions

Figure 1:
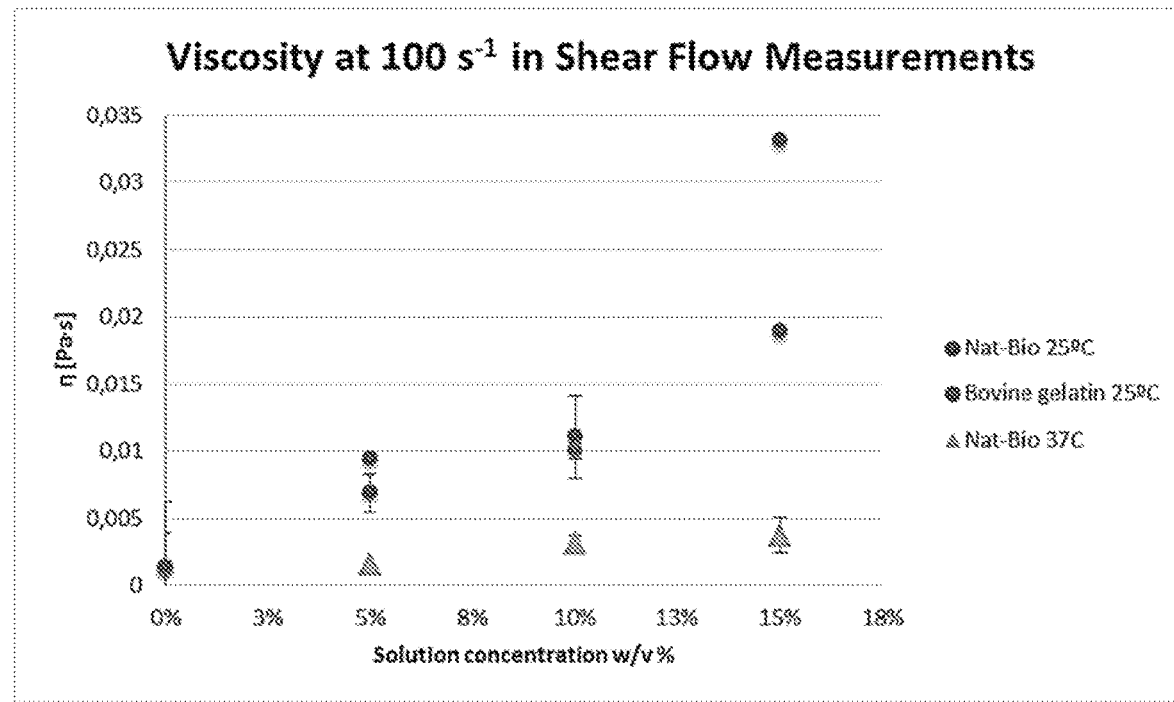
FIG. 1. Viscosity measured at 100 $s^{-1}$ shear flow. At 25° C. increases in concentration gave much higher increases in viscosity in the case of bovine methacrylated gelatin in comparison to salmon methacrylated gelatin. 0.02 Pa·s is equivalent to 20 centipoises. All biomaterials had de same level of chemical functionalization as illustrated in the examples.

As used herein, "natural sources of cold-adapted marine species" is understood as biological compounds, in particular gelatin extracted from living species that habitats or is adapted to marine cold-environments. As such, these types of compounds, especially cold-adapted polymers, acquire special properties for well functioning at lower temperatures. Some of these properties are: Lower viscosity at certain concentrations compare to mammalians-derived compounds, lower gelation temperature, liquid state stability at lower temperatures, lower surface tension in solution and higher molecular mobility or flexibility.

As used herein, "chemically functionalized" is understood as a compound, biological compound or polymer in which chemical groups are been added to their chemical structure by a chemical or biochemical reaction. Positions at which the chemical group can be added during the chemical or biochemical reaction can be determined by the reactivity of the chemical groups present in the original chemical structures. Additionally, compounds or polymers can be previously treated to add reactive groups in their chemical structure in order to give access to new chemical groups that constitute a functionalization.

As used herein, "acryloyl groups" is form of enone with structure $H_2C=CH-C(=O)-$; it is the acyl group derived from acrylic acid. The preferred IUPAC name for the group is prop-2-enoyl, and it is also (less correctly) known as acrylyl or simply acryl. Compounds containing an acryloyl group can be referred to as "acrylic compounds". An acrylic compound is typically an α,β-unsaturated carbonyl compound: it contains a carbon-carbon double bond and a carbon-oxygen double bond (carbonyl) separated by a carbon-carbon single bond, thus possessing properties characteristic for both functional groups:

at the C=C bond: electrophilic addition of acids and halogens, hydrogenation, hydroxylation and cleavage of the bond at the C=O bond: nucleophilic substitution (such as in esters) or nucleophilic addition (such as in ketones).

The carboxyl group of acrylic acid can react with ammonia to form acrylamide, or with an alcohol to form an acrylate ester.

As used herein, "chemical photoinitiator" is understood as a chemical compound or molecule that after light stimulation or application, covalent bonds break forming one, two or more radicals to assist radical polymerization.

As used herein, "amino acidic chain gelatin polymer" is understood as a series of amino acid monomers connected together by peptidic-bonds. This chain of bonded amino acids as a particular sequence of amino acidic identity corresponded to sequence of collagen type I, however, after the extraction process, these collagen polymer suffers from some amino acidic modifications and shortening of the sequence to a certain extend depending on the extraction conditions. In this way, gelatin is understood as a partially hydrolyzed and de-naturated collagen.

As used herein, "a degree of functionalization at the amino acidic side chains" is understood as the number of amino acids from the total number of amino acids comprising a peptide, polypeptide or otherwise sequence of covalently bonded amino acids that had suffered a chemical modification and in consequence an addition of a chemical group in their original chemical structure.

As used herein, "cooling pre-treatment" is understood as a step in a process in which a compound or polymer is subjected to incubation at temperatures lower than room temperature, approximately lower than 21° C.

As used herein, "solution" is a homogeneous mixture composed of two or more substances. In such a mixture, a solute is a substance dissolved in another substance, known as a solvent. The solution more or less takes on the characteristics of the solvent including its phase, and the solvent is commonly the major fraction of the mixture. The concentration of a solute in a solution is a measure of how much of that solute is dissolved in the solvent, with regard to how much solvent is present like salt.

As used herein, "3D printing" is understood as the process of fabrication of 3 dimensional structures usually created in successive steps of layer by layer generation. It differentiates from carving since 3D printings create specific structures either accessible or not accessible from the peripheral boundary of the structure, while carving recreate features by removing material from an original solid, where all created structures are accessible from the outside.

As used herein, "extrusion systems (additive fabrication)" is understood as systems capable to make pass material through a nozzle by applying pressure in order to deposited material on a surface.

As used herein, "spray systems" is understood as a system capable to push material through a specially design nozzle by applying pressure in order to create small spread particles or drops.

As used herein, "casting" is understood as a process of filling a previously generated mold in order to recreate specific shapes out of the filler material after curing, polymerization or crosslinking.

As used herein, "micro- and nano fibers fabrication systems (electrospinning)" is understood as a system that extrudes a polymeric solution within a strong electric field form between the extrution nozzle and the zone of material deposition, generating a deposition of nano and microfibers of the polymer in a more solid state. The term "electrospinning" is known in the art, and is a process in which a charged polymer jet is collected on a grounded collector; a rapidly rotating collector results in aligned nanofibers while stationary collectors result in randomly oriented fiber mats. The polymer jet is formed when an applied electrostatic charge overcomes the surface tension of the solution. There is a minimum concentration for a given polymer, termed the critical entanglement concentration, below which a stable jet cannot be achieved and no nanofibers will form—although nanoparticles may be achieved (electrospray). A stable jet has two domains, a streaming segment and a whipping segment. While the whipping jet is usually invisible to the naked eye, the streaming segment is often visible under appropriate lighting conditions. Observing the length, thickness, consistency and movement of the stream is useful to predict the alignment and morphology of the nanofibers being formed. The stream can be optimized by adjusting the composition of the solution and the configuration of the electrospinning apparatus, thus optimizing the alignment and morphology of the fibers being produced. Any known methods for electrospinning the polymers used herein can be used with the methods of the present invention to provide the multifunctional biomaterials disclosed herein. As used herein, "microfluidics" is understood as devices comprise of a circuit of channels at micrometric sizes, where fluids are been perfused forming generally laminar flows (flows with parallel vectors and non-turbulent flows) within the channels.

Description

As already mentioned, the biomedical field demands a number of physicochemical and biological properties that influences the results of the therapeutic or diagnostic applications. Some of these properties are related to control of the microenvironment of the cellular components and a direct interaction of the biomaterial with the cells that derived in specific biological responses and active remodeling of the biomaterial in response to cell biological activities. These properties are also listed as control delivery of biologically meaningful elements, cytocompatibility, bioactivity and biodegradability. On the other hand, in the alimentary field, there is a need for specialized and cost-efficient technologies for deposition of food coatings such as spray systems or beads fabrication for supplementation of encapsulated vitamin or other active compounds. Unfortunately, both of these fields are limited in performance due to the suboptimal rheological nature and control of polymerization/crosslinking of the majority of the biomaterials used thus far. Therefore, new biomaterials for use in these technologies are urgently needed. Consequently, there is still a need for novel highly bioactive biomaterials that can create structurally complex scaffolds with the desired geometry, biological and physical properties for optimal application in biomedicine and food.

The present invention solves the above problem by providing a composition (from hereinafter "composition of the invention") comprising an amino acidic chain gelatin polymer derived from natural sources of cold-adapted marine species, in particular from the genus *Salmo* and *Oncorhynchus*, and chemically functionalized to become reactive to polymerization or crosslinking in presence of free radicals. The nature of functionalization could be diverse, including methacryloyl groups to acryloyl groups (see brief description of the invention). Such chemical functionalization of the biomaterial provides for a quick control of polymerization or crosslinking into a more solid and thermally stable hydrogel when such chemically functionalized hydrogel is subjected to free radicals. Moreover, surprisingly such functionalization modifies the rheological properties of the biomaterial, as illustrated below.

To illustrate such rheological properties, we have manufactured a basic formulation of the composition of the invention, which comprises a solution of methacryloyl salmon gelatin in a concentration of about 1% to 20% (w/v), adding a chemical photoinitiator (which generates free radicals in presence of intense light at certain wave length) in a concentration of about 0.01% to 5% (w/v). The degree of chemical functionalization at different amino acidic side chains, especially lysine, can be from 1% to 100%. Polymerization or crosslinking of this solution is induced by exposition with light. We have also manufactured a further basic formulation, which comprises a solution of methacryloyl bovine gelatin in a concentration of about 1% to 20% (w/v), adding a chemical photoinitiator (which generates free radicals in presence of intense light at certain wave length) in a concentration of about 0.01% to 5% (w/v), as a comparative example Lastly, we have also manufactured a solution of non-methacryloyl salmon gelatin in a concentration of about 1% to 20% (w/v). All of these solutions have been manufactured according to examples 1 to 3 as detailed in the present specification.

As shown in FIG. 1, at 25° C. there is an increased in the concentration of both gelatin solutions, methacryloyl bovine gelatin solution and the methacryloyl salmon gelatin solution. However, such increased of the viscosity as measured at 100 s$^{-1}$ shear flow, gave much higher increases for bovine methacrylated gelatin in comparison to salmon methacrylated gelatin. In fact, a solution of salmon methacrylated gelatin in a concentration of about 1% to 20% (w/v), provided for a solution comprising amino acids polymers with the following rheological properties:

Viscosity at 25° C.: 3-20 centipoises.
Viscosity at 37° C.: 1.5-8 centipoise.

These values of viscosity are especially useful in bio fabrication technologies such as, but not limited to, spraying or 3D printing, since high-performance functioning of these technologies is highly dependent on the rheological properties of the biomaterial at the liquid state.

Figure 2:
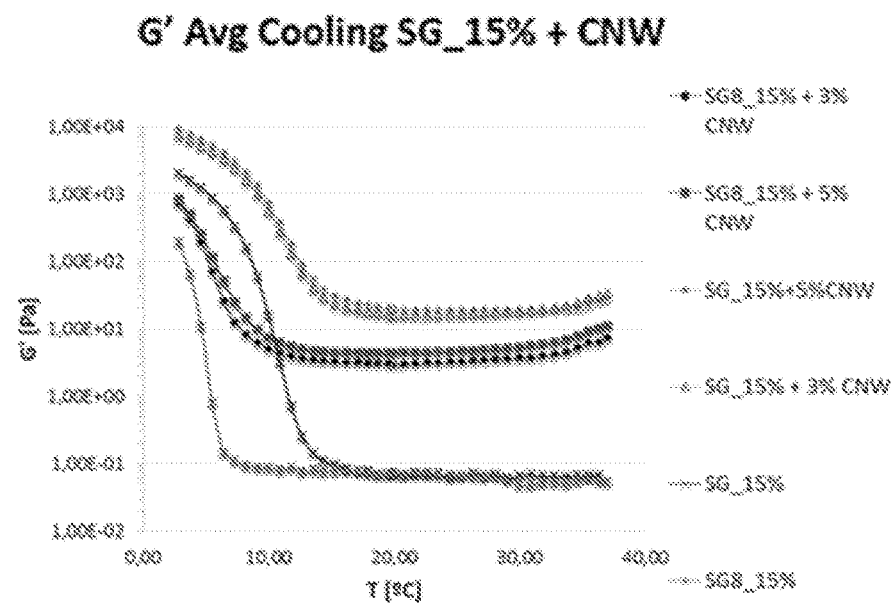
FIG. 2. Gelification temperatures. Shear modulus or modulus of rigidity, denoted as G', increases during gelification of biomaterials. Methacrylated Salmon gelatin (SG8) at 15% concentration (w/v) decreases its gelification temperature as compared with non-methacrylated salmon gelatin (SG). The other curves shown in this figure correspond to composites which included filler molecules such as cellulose nanowhiskers (CNW), showing similar correlation of gelification/temperature, but higher shear modulus.

As regards the gelification temperature and as shown in FIG. 2, methacrylated Salmon gelatin (SG8) at 15% concentration (w/v) decreases its gelification temperature compared with non-methacrylated salmon gelatin (SG), thus making methacrylated salmon gelatin more rheologically stable at a broader range of temperatures. In addition, the other curves illustrated in FIG. 2 correspond to composites which included filler molecules such as cellulose nanowhiskers (CNW). Such composites showed similar correlation of gelification/temperature, but higher shear modulus. Such higher shear modulus makes these composites much less favorable for inkjet bio-printing processes.

Figure 3:
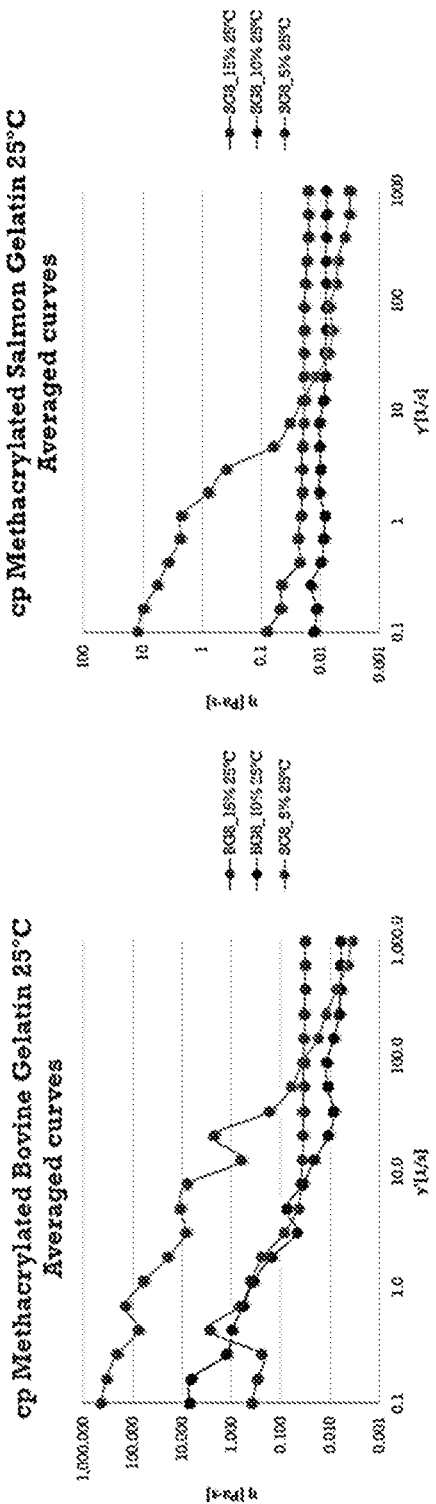
FIG. 3. Change of fluid's viscosity in response to changes in shear flow. Bovine gelatin shows a shear thinning effect, typical of non-Newtonian behavior of fluids, while for salmon gelatin, Newtonian behavior is observed (no changes in viscosity as a result of increasing shear flow).

In addition, as shown in FIG. 3, change of fluid's viscosity in response to changes in shear flow, bovine gelatin shows a shear thinning effect, typical of non-Newtonian behavior of fluids, while for salmon methacrylated gelatin Newtonian behavior is observed (no changes in viscosity as a result of increasing shear flow). In particular, in a concentration range of the methacryloyl salmon polymer from 5% to 20% the solution behaved as a Newtonian solution.

Figure 4:
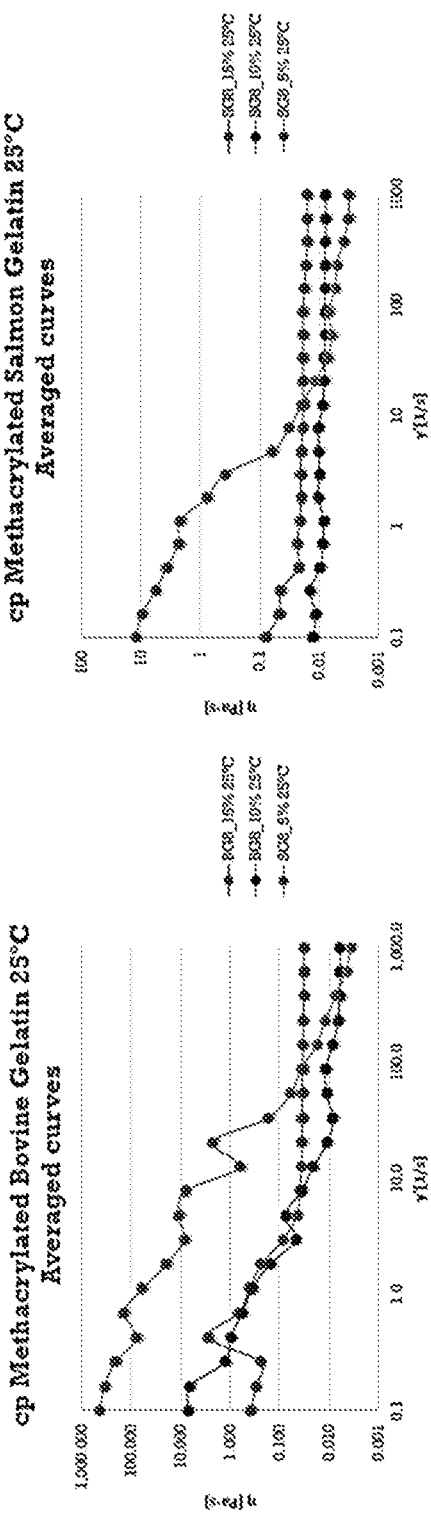
FIG. 4. Change of fluid's viscosity in response to changes in shear flow. Comparing methacrylate gelatin from bovine or salmons, salmon showed much lower values of viscosity at different shear flow. Methacrylated salmon gelatin showed Newtonian behavior at different concentrations, excepting for the 5% (v/w) concentration. On the other side, all tested concentrations of methacrylated bovine gelatin showed non-Newtonian behavior.
Figure 5:
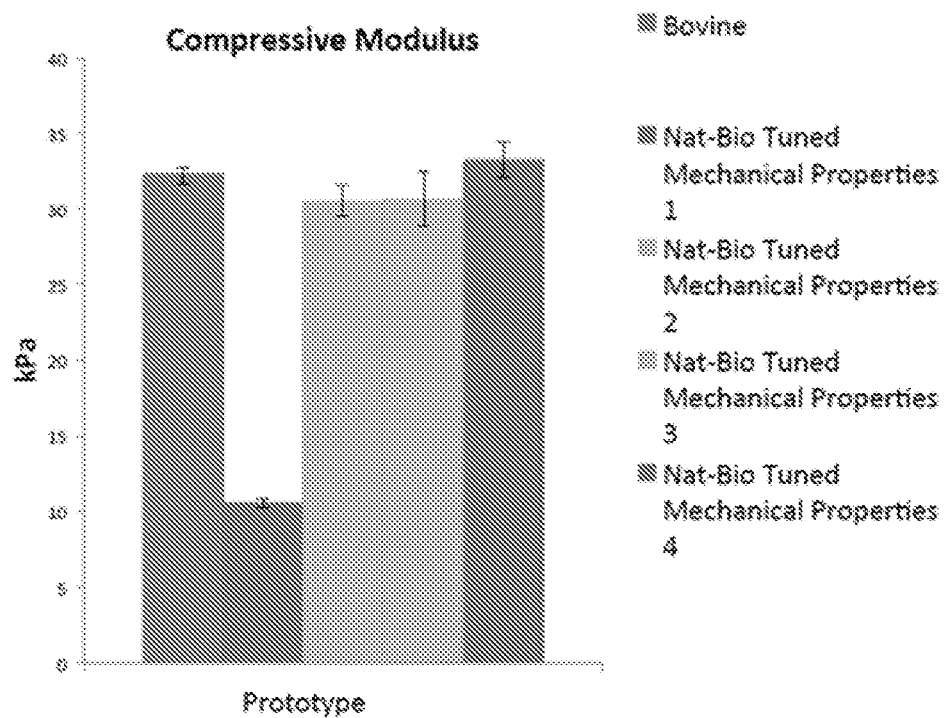
FIG. 5. Compressive modulus of photocrosslinked (0.5% photoinitiator) hydrogel of methacrylated bovine gelatin at 10% concentration and 80% functionalization at lysine amino acids, and comparisons to hydrogel based on salmon gelatin at the same concentration but with 20% functionalization (red), 60% (green), 78% (orange) and 85% (purple).

Furthermore, as shown in FIG. 4, comparing methacrylated gelatin obtained from bovine or salmons, salmon showed much lower values of viscosity at different shear flows. In addition, methacrylated salmon gelatin showed Newtonian behavior at different concentrations. On the other hand, all tested concentrations of methacrylated bovine gelatin showed non-newtonian behavior.

It is additionally noted that although surface tension has not been calculated in the experiments conducted thus far, adding surfactant concentrations between 0.01% up to 5%, does not change the viscosity or the Newtonian behavior of the methacrylated salmon gelatin. This means that surface tension of the biomaterial solution can be controlled by adding a surfactant such as Kolliphor® P 188 (Sigma-Aldrich).

In 3d printing technologies such as high precision inkjet (polyjet, stratasys), printing biomaterials with viscosities above 20 centipoises deteriorate significantly the 3D printing performance. As shown above, the methacrylated salmon gelatin solution has a viscosity lower than 20 centipoises at a wide range of temperatures, making this solution or composition especially useful in 3d printing technologies and other applications which required such low viscosities at a broad range of temperatures (i.e. spraying for food coating applications). Similarly, biomaterials with non-Newtonian behavior or high surface tension also deteriorate bio fabrication technologies. In this regard, the methacrylated salmon gelatin solution, as shown above, behaved as a Newtonian solution in a broad range of concentrations and temperatures.

Furthermore, stability of the liquid state and rapid polymerization is another important aspect in bio fabrication technologies, such as 3D printing. In this sense, biomaterials with gelation temperatures close to room temperature, during the printing process, caused serious deleterious effects in these systems, and eventually blockage of the flow circuits in the printer head due to gelification of the biomaterial. The same problems apply for microfluidics systems in which their functioning is based on precise control of laminar nano- and microliter flows, where any change in viscosity and gelification episodes disrupts the control of flows in the system. Spray systems likewise cannot perform using highly viscous or worse, gelling biomaterials.

For all of the above reasons, a solution comprising an amino acidic chain gelatin polymer, derived from natural sources of cold-adapted marine species, preferably from the genus *Salmo* and *Oncorhynchus*, and chemically functionalized to become reactive to polymerization or crosslinking in presence of free radicals at a concentration of about 1% to 20% (w/v), provides for a composition having rheological properties especially suitable for bio fabrication technologies such as 3D printing, microfluidic systems and spraying systems for use in biomedical applications or for applications in the alimentary field.

Therefore, in a first aspect the present invention refers to a composition comprising a solution which in turn comprises an amino acidic chain gelatin polymer derived from natural sources of cold-adapted marine species, at a concentration from 1% to 20% (w/v), which optionally further comprises a polymerizing initiator such as a photoinitiator, and is chemically functionalized to become reactive to polymerization or crosslinking in presence of free radicals.

As above-mentioned, gelatin is obtained by partial hydrolysis of collagen, which is the main fibrous protein constituent of bones, skin and connective tissue. It is known in the art that the source of collagen influences the properties of the gelatins.

An amino acid chain gelatin polymer derived from natural sources of cold-adapted marine species, includes for instance an amino acid chain gelatin polymer derived from cold-adapted marine fish species (e.g. from its skin, bones, fins and/or scales). The list of cold-adapted marine fish species includes members of the genus *Gadus*, such as cod (e.g *Gadus morhua* or *Gadus macrocephalus*) or Allaska Pollok (*Gadus chalcogrammus*), of the genus *Salmo*, such as atlantic salmon (*Salmo salar*, of the genus *Oncorhynchus* (pacific salmon), which includes pink salmon (*Oncorhynchus gorbuscha*), Chinook salmon (*Oncorhynchus tshawytscha*), Chum salmon (*Oncorhynchus keta*), Coho salmon (*Oncorhynchus kisutch*), Masu salmon (*Oncorhynchus masou*), and Sockeye salmon (*Oncorhynchus nerka*), haddock (*Melanogrammus aeglefinus*) belonging to the the Gadidae family as cod; and of the *Merluccius* genus. This list is not particularly limited, as mentioned by Gomez-Guillén M C et al (Food Hydrocolloids 2011, 25(8) 1813-1827) the number of fish or marine species which are suitable for gelatin extraction is continually growing.

In recent years, several studies aiming to structurally and functionally characterize fish gelatins have been conducted, see for instance Leuenberger B H: Food Hydrocolloids 1991, 5(4) 353-61. Lim et al: Food Science 1999, 64(4), 616-22; Choi and Regenstein Food Science 2000, 65(2), 194-9; Gilsenan P M et al: Food Hydrocolloids 2000, 14(3), 191-5; Gomez-Guillén M C et al: Journal of Science and Food Agriculture 2001, 81(7), 665-73; Haug I J et al: Food Hydrocolloids 2004, 18(2), 203-13; Cho S M et al: Food Hydrocolloids 2005, 19(2), 221-9, Gomez-Guillén M C et al: Food Hydrocolloids 2011, 25(8) 1813-1827; Karim A A et al: Food Hydrocolloids 2009, 23(3), 563-576; and Boran G and Regenstein J M, Adv Food Nutr Res. 2010; 60:119-43, which are hereby incorporated by reference.

The amino acid composition of gelatin is very close to that of its parent collagen, and is characterized by a repeating sequence of Gly-X-Y triplets, where X is mostly proline and Y is mostly hydroxyproline. Fish gelatins, and in particular cold-adapted species are characterized by having a proline and hydroxyproline content which is lower than that of gelatin isolated from mammalian species (Karim A A et al: Food Hydrocolloids 2009, 23(3), 563-576).

Overall, fish gelatins have lower concentrations of imino acids (proline and hydroxyproline) compared to mammalian gelatins, and warm-water fish gelatins (such as bigeye-tuna and tilapia) have a higher imino acid content than cold-water fish (such as cod, whiting and halibut) gelatins (Eastoe & Leach, chemical constitution of gelatin. In A. G. Ward, & A. Courts (Eds.), The science and technology of gelatin (pp. 73-107). New York: Academic Press). The proline and hydroxyproline contents are approximately 30% for mammalian gelatins, 22-25% for warm-water fish gelatins (tilapia and Nile perch), and 17% for cold-water fish gelatin (cod) (Muyonga et al., Food Hydrocolloids. 2004, 18. 581-592). To illustrate this, Karim A A et al (Food Hydrocolloids 2009, 23(3), 563-576) shows in Table 2 of the amino acid content of some fish gelatins compared to pork gelatin (number of residues/1000 amino acid residues).

In a particular embodiment, optionally in combination with one or more of the features described above or below, the amino acidic chain gelatin polymer derived from natural sources of cold-adapted marine species of the invention is characterized by presenting a content of proline and hydroxyproline equal to or less than 20%, preferably equal to or less than 19%, 18%, 17%, 16% or 15%. In addition to, or alternatively, this amino acidic chain gelatin polymer is characterized by presenting from 50 to 60 residues of hydroxyproline per 1000 total amino acid residues and from 95 to 115 residues of proline per 1000 total amino acid residues.

In a preferred embodiment of the first aspect of the invention, optionally in combination with one or more of the features described above or below, the gelatin polymer is derived from the genus *Salmo* or *Oncorhynchus*, preferably the gelatin polymer is derived from salmon.

Preferably, the composition comprises an amino acidic chain gelatin polymer at a concentration from 5% to 20% (w/v). More preferably, the composition further comprises a surfactant. Still more preferably, the amino acidic chain gelatin polymer of the composition is functionalized with a chemical agent selected from the group consisting of methacryloyl groups, acryloyl groups or any functional group or a moiety capable of mediating formation of a polymer or reaction with a surface or other molecule. Functional groups include the various radicals and chemical entities taught herein, and include alkenyl moieties such as acrylates, methacrylates, dimethacrylates, oligoacrylates, oligomethacrylates, ethacrylates, itaconates or acrylamides. Further functional groups include aldehydes. Other functional groups may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrile and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene, and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid, and styrene carboxylic acid. Suitable polyethylenically unsaturated monomers include butadiene, isoprene, allylmethacrylate, diacrylates of alkyl diols such as butanediol diacrylate and hexanediol diacrylate, divinyl benzene, and the like. It is preferred that the amino acidic chain is functionalized with methacryloyl groups.

As stated, such solution or composition is functionalized with chemical groups reactive to free radicals, thus allowing quick polymerization/crosslinking when combined with photoinitiators and exposed to light, visible or UV light or infrared depending on the nature of the photoinitiator. Preferred chemical groups are methacryloyl groups or acryloyl groups. Suitable photoinitiators useful in the present invention are well known in the art.

In a preferred embodiment of the first aspect of the invention, optionally in combination with one or more of the features described above or below, the polymerizing initiator is a photoinitiator such as Irgacure® 2959 [(Ciba specialty chemical now BASF Resins], preferably in a concentration of about 0.01% to 5% (w/v). It is noted that in the context of the present invention, a "polymerizing initiator" refers to any substance that can initiate polymerization of monomers or macromers by, for example, free radical generation. The polymerizing initiator often is an oxidizing agent. Exemplary polymerization initiators include those which are activated by exposure to, for example, electromagnetic radiation or heat. Polymerization initiators can also be used and are described, e.g., in U.S. Patent Application Publication No. 2010/0137241, which is incorporated by reference in entirety.

Additionally, such solution or composition having a concentration range of the chemically functionalized polymer from 1% to 20%, preferably from 5% to 20%, can comprise a variable degree of functionalization at the amino acidic side chains, especially lysine, from 5% to 100%, preferably such solution or composition comprises a variable degree of functionalization at the amino acidic side chains, especially lysine, from 20% to 100%, 30% to 100%, 50% to 100%, 60% to 100%, 70% to 100%, 80% to 100% or from 90% to 100%, preferably of about 90%.

Conversion of collagen into soluble gelatin can be achieved by chemical or enzymatic hydrolysis. This process results in the cleavage of a number of intra- and intermolecular covalent crosslinking that are present in collagen. In addition, some amide bonds in the chains of collagen molecules undergo hydrolisis. The extraction process may influence the length of the polypeptide chains and the functional properties of the gelatin.

Typically, chemical hydrolysis comprises mildly heating collagen in either acid or alkali to break cross-linking bonds. In general, a mild acid pretreatment is used prior to gelatin extraction. Fish gelatins have been extracted using a number of different methods. Because of the acid lability of the crosslinks found in fish skin collagen, mild acid treatment is generally sufficient to produce adequate swelling and to disrupt the non-covalent intra- and intermolecular bonds. The pH of extraction of gelatin of a cold-adapted marine species is typically between 3 and 5.5, preferably it is between 4 and 5, such as about 4.1, 4.2, 4.3, 4.4, 4.5, 4.6, 4.7, 4.8, 4.9 or 5, more preferably the pH of extraction is about 5. In order to increase collagen extraction yield, appropriate protease inhibitors (e.g. pepstatin A) can also be used during the extraction process. Table 4 of Karim A. A. et al. Food Hydrocolloids 2009, 23(3), 563-576 summarizes several processes previously described for extracting fish gelatin which may be used for the extraction of the amino acidic chain gelatin polymer derived from natural sources of cold-adapted marine species of the invention.

In a particular embodiment, the method of extracting the amino acidic chain gelatin polymer derived from natural sources of cold-adapted marine species comprises a mild acidic and mild basic pre-treatment. Preferably, said gelatin extraction process comprises:

An alkalyne hydrolysis at a pH about 13 (e.g. with NaOH 0.1M at pH: 13.4);

An acid hydrolysis at a pH about 4 (e.g. acetic acid 0.05 M at a pH: 3.8); and

Gelatin extraction at a temperature between 50° C. and 70° C. (preferably about 60° C.) and pH adjustment between 3 and 5.5 (preferably about pH 5). The time of incubation is not particularly limited and usually takes from minutes to hours, preferably from 2 to 4 hours, more preferably 3.5 h. In a preferred embodiment, the gelatin extraction takes place at 60° C. for 3.5 h at a pH of about 5.

Said composition may further comprise a surfactant in a concentration from 0.001% to 10%, preferably from 0.01% to 1%. In a particular embodiment, said surfactant is selected from the group consisting of SDS, tween 20, and poloxamers (such as Kolliphor® P 188 (Sigma-Aldrich)), or the like.

In another embodiment, said surfactant is a biocompatible surfactant. Biocompatible surfactants are well known in the art and include as illustrative non-limiting examples Perfluoropentane (PFP), polyethylene oxide-co-polylactic acid (PEO-PLA), polyethylene oxide-co-poly-ε-caprolactone (PEO-PCL), cetyl trimethyl ammonium bromide (CTAB), bovine serum albumin (BSA), Pico-Surf™ 1, Novec™ 7500, FC-40, Amino-acid-based surfactants (amino acid-based surfactants with one single chain, cystine or arginine gemini surfactants, lysine derivatives, and surfactants with glycerolipid-like structure). Preferably, this biocompatible surfactant is selected from the group consisting of fluoro-surfactants. Fluorosurfactants are characterized by presenting perfluorated alkyl tails. These surfactants have been shown to be more efficient in decreasing surface tension than non perfluorated surfactants. There is however the associated drawback that these compounds are known to bioaccumulate and thus to be toxic. Biocompatible fluorosurfactants include for instance perfluorohexanoic acid (PFHxA), perfluorobutanesulfonic acid_and perfluorobutane sulfonate (PFBS). It has been shown that perfluorated surfactants with alkyl tails of less than 6 carbons have reduced bioaccumulation. Accordingly, in a preferred embodiment, said biocompatible surfactant is a perfluorated surfactant with alkyl tails of less than 6 carbons. This includes but it is not limited to Novec FC-4430 (3M™), Zonyl FSN-100 (DuPont™) y trisiloxane surfactant (Silwet L-77). Particularly preferred perfluorated surfactants with alkyl tails of less than 6 carbons are fluorosurfactants with a ramified short alkyl tail, such as of 2, 3, 4 or 5 carbons, preferably of 2 carbons. In a more preferred embodiment, these surfactants are branched fluorosurfactants comprising several $C_2F_5$ chains. This includes TIVIDA™ surfactants developed by Merck, such as TIVIDA 2300 and TIVIDA 2500.

Example 9.2 shows that branched fluorosurfactants with less than 6 carbons (i.e TIVIDA 2300 and TIVIDA 2500) have reduced cell toxicity (notably in comparison with BYK-345 which was found to be cytotoxic) and improved cell viability (it was higher than the control of hydrogel based on modify salmon gelatin alone). It is possibly that this better cell viability is correlated to a higher diffusion coefficient of nutrients, metabolites and gases within the hydrogel due to presence of fluorosurfactants (TIVIDA 2300, TIVIDA 2500).

In a particular embodiment, optionally in combination with one or more of the features described above or below, said fluorosurfactant with alkyl tails of less than 6 carbons is in a concentration from 0.005% to 0.1% (w/v), preferably from 0.01% to 0.03% (w/v), even more preferably of about 0.02% (w/v).

In addition, said composition can comprise a branched polyethyleneglycol derivative, such as multi-arm PEG derivatives. The concentration of the branched can be from 0.1% to 10% (w/w), preferably from 1% to 5% (w/w), more preferably about 1%, 1.5%, 2%, 2.5%, 3%, 3.5%, 4%, 4.5% or about 5%. Preferred branched PEG derivatives are selected from the group consisting of tripentaerythritol (8ARM(TP) PEG) (also referred herein as 8arm-PEG10K-Acrylate), tripentaerythritolhexaglycerol (8ARM PEG), dipentaerythritol (6ARM PEG), pentaerythritol (4ARM PEG), glycerol (3ARM PEG), 3arm and 4arm Heterofunctional PEGs, and finally Heterobifunctional PEGs. All of them could have variable PEG length.

In Example 9.1 was tested the resistance to exposure to uv light of a composition of the invention which further comprises a branched polyethyleneglycol derivative, such as multi-arm PEG derivatives at concentrations of 1% and 5% (w/w). The concentration of 1% (w/w) showed a fairly cross-linked hydrogel after 2 passes of the warming UV light without signals of dehydration. Furthermore, said formulation was shown to maintain its viscosity and Newtonian behavior. On the other hand, the 5% (w/w) formulation was shown to resist dehydration even after 4 passes. Moreover, crosslinking reactivity was shown to be further improved.

In a preferred embodiment, said composition further comprises a branched fluorosurfactant with less than 6 carbons and a branched PEG derivative as described herein. According, to the experimental results described herein such a composition would have the following characteristics:

Newtonian behavior

Low viscosity (5.5-20 cP)

Low surface tension

High crosslinking reactivity and structural integrity

Good mechanical properties (compressive modulus between 25-100 kPa)

Good higroscopicity

Cytocompatibility

Good nutrients, metabolites and gases diffusion.

In a preferred embodiment, optionally in combination with one or more of the features described above or below, said composition comprises:

1% to 20% (w/v) of cold-adapted marine species (preferably, salmon) methacryloyl gelatin functionalized in more than 80% (preferably, in more than 85%) of its lysine groups;

a branched PEG derivative (preferably, 8arm-PEG10K-Acrylate tripentaerythritol) at a concentration from 0.1 to 10% (w/w), preferably at a concentration from 1% to 5% (w/w);

a fluorosurfactant at a concentration from 0.005% to 0.1% (w/v); and a photoinitiator at a concentration from 0.01% to 5% (w/v).

In an even more preferred embodiment, optionally in combination with one or more of the features described above or below, said composition comprises:
- 15% (w/v) of cold-adapted marine species (preferably, salmon) methacryloyl gelatin functionalized at approximately 90% of its lysine groups;
- a branched PEG derivative (preferably, 8arm-PEG10K-Acrylate tripentaerythritol) at a concentration from 1% to 5% (w/w);
- a branched fluorosurfactant with less than 6 carbons (preferably, with a $C_2F_5$ chain) at a concentration from 0.005% to 0.1% (w/v); and
- a photoinitiator at a concentration from 0.05% to 0.5% (w/v), preferably of about 0.2% (w/v).

In another preferred embodiment of the first aspect of the invention, the solution is pre-treated with temperature of from 5° C. to 15° C., prior to cross-linking, during a time interval of from 1 msec to 4 hours, preferably from 1 second to 4 hours, more preferably from 1 minute to 4 hours, preferably from 10 minutes to 4 hours, more preferably from 30 minutes to 4 hours, more preferably from 45 minutes to 4 hours, still more preferably from about 1 hr to about 4 hrs, still more preferably from about 1 hr to about 3 hrs.

Figure 6:
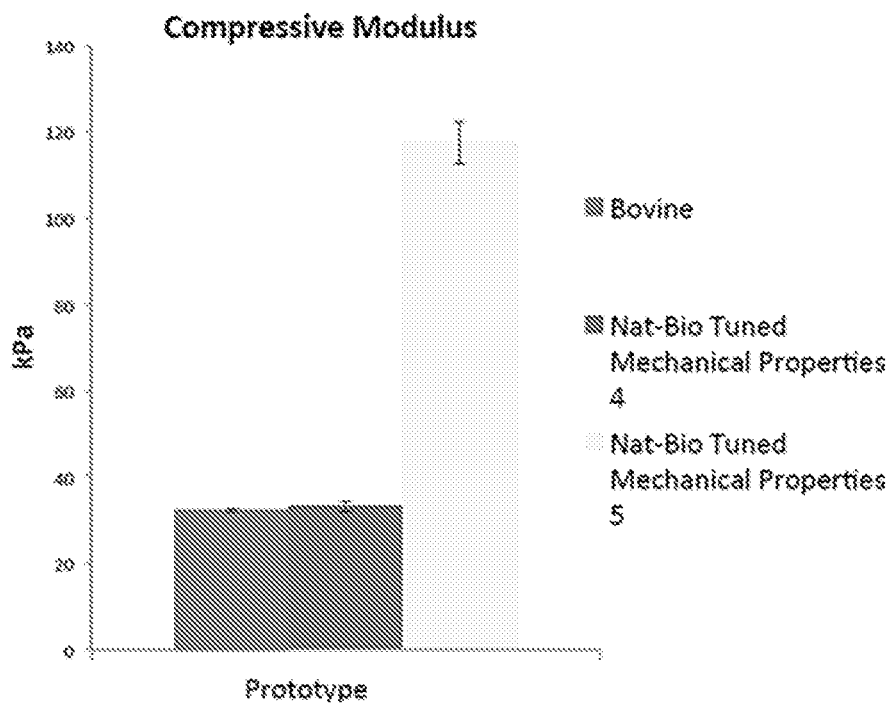
FIG. 6. Compressive modulus of photocrosslinked (0.5% photoinitiator) hydrogel of methacrylated bovine gelatin at 10% concentration and 80% functionalization at lysine amino acids, and comparisons to hydrogel based on salmon gelatin at the same concentration but with 78% functionalization (purple), and 78% functionalization with a cooling pre-treatment of 2 hrs at 4 C.° (yellow).
Figure 7:
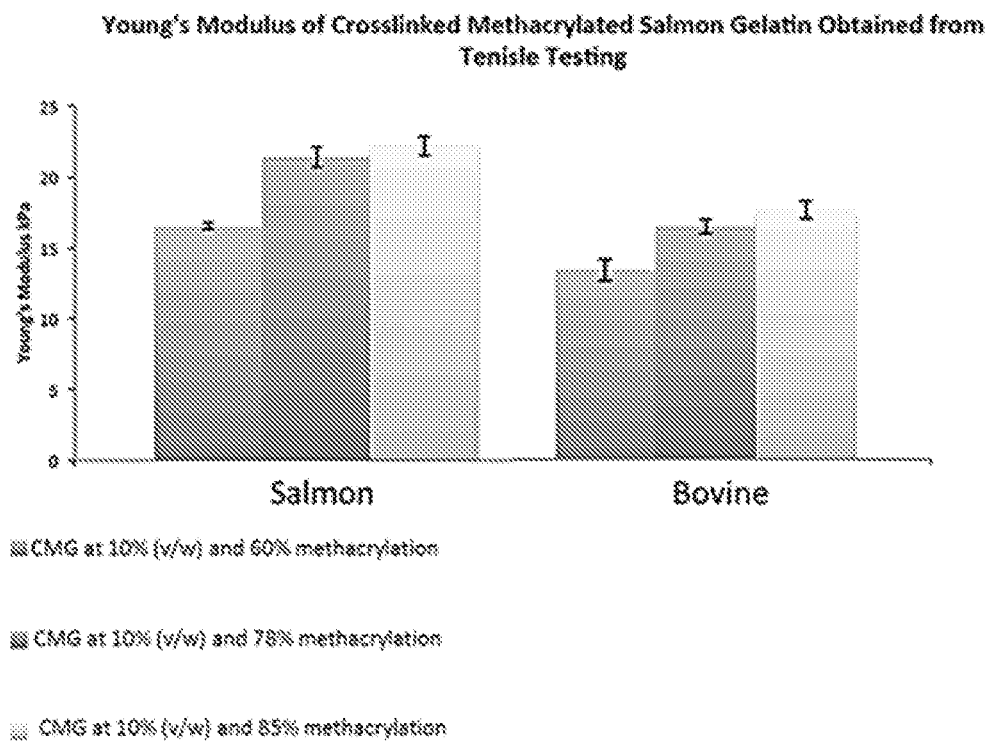
FIG. 7. Tensile young's modulus. Tensil testing of Cross-linked methacrylated Gelatin (CMG) hydrogel with different degree of functionalization at lysine groups (60%, 78% and 85%) were tested comparing Salmon and bovine origin Similar results were observed with slightly higher values for salmon gelatin.

As illustrated in FIG. 6, a temperature pre-treatment before crosslinking within the range of 1° C. to 12° C. during a variable time, preferably less than 4 hours, greatly increases the mechanical properties (compressive modulus) of the polymerized/crosslinked biomaterial.

Figure 8:
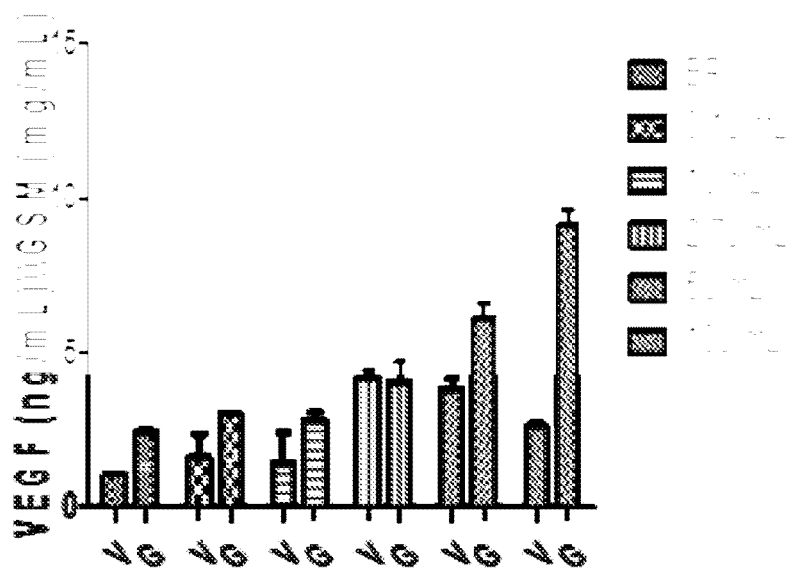
FIG. 8. Delivery rate of encapsulated factor in 24 hr. Hydrogels of methacrylated salmon gelatin at 10% (v/w) concentration and 80% functionalization with encapsulated factor (VEGF) at a concentration of 100 ng/ml were incubated in cell culture media at 37° C. Different concentrations of collagenase type II (Whortington) were used and evaluated the rate of VEGF delivery into the supernatant. The graft shows concentration of delivered VEGF and soluble polymers of salmon gelatin.
Figure 9:
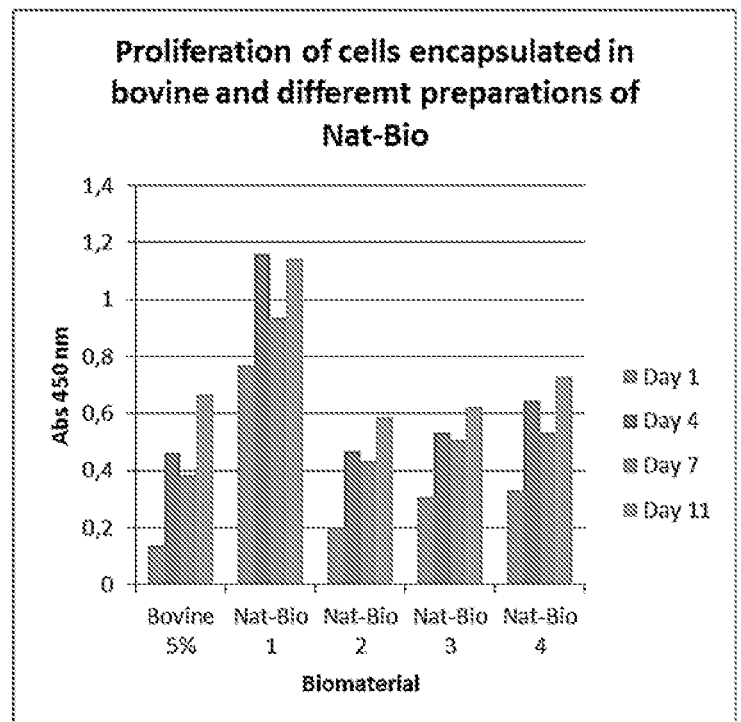
FIG. 9. Cell proliferation assessment of encapsulated HUVEC in the crosslinked biomaterials were performed using the WST-1 Cell Proliferation Colorimetric Assay Kit (K302, Biovision, USA) following the manufacturer instructions. Briefly, this assay quantifies the metabolic cleavage of WST-1 to generate formazan by cellular mitochondrial dehydrogenases. Here comparisons of hydrogels of methacrylated bovine gelatin at 10% (v/w) concentration and 78% functionalization (at lysine side-chains) were compare to methacrylated salmon gelatin at 10% (v/w) concentration and 20% functionalization (Nat-Bio 1), 60% functionalization (Nat-Bio 2), 78% (Nat-Bio 3) and 85% (Nat-Bio 4).
Figure 10:
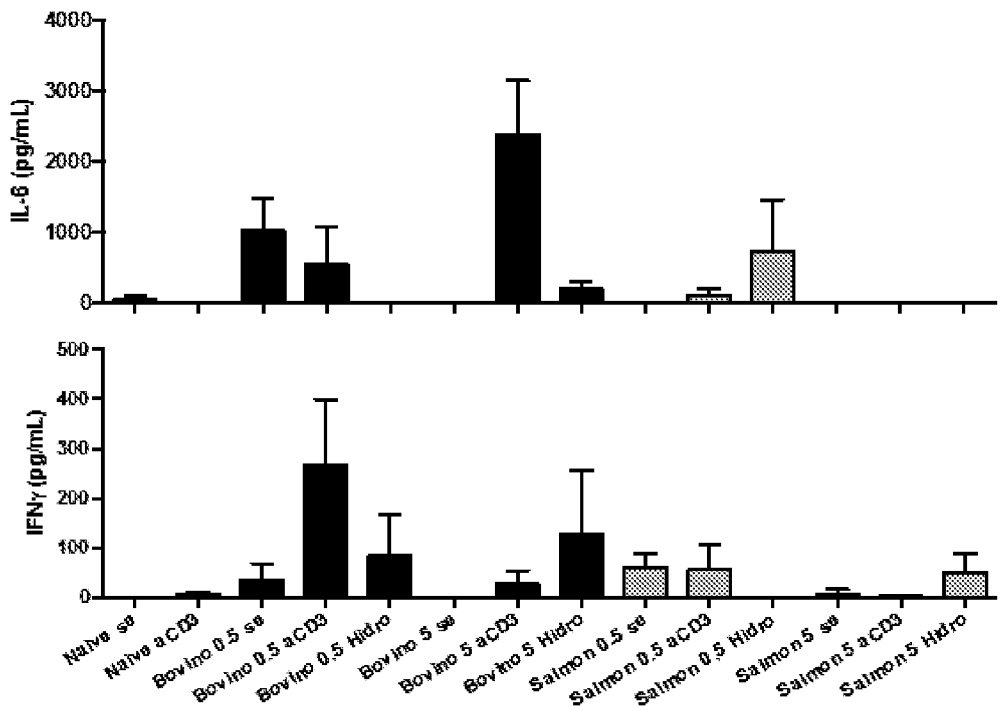
FIG. 10. Imunogenecity of crosslinking hydrogel and comparison between salmon and Bovine. Salmon and Bovine gelatin hydrogels at 10% (v/w) concentration with 20% functionalization (Bovine 0.5, Salmon 0.5) or 78% functionalization (Bovine 5, Salmon 5) were prepared and implanted subcutaneously in mice (C57 b1/6). After 14 days, leucocytes from the mice axillar lymph node were isolated and culture in absence or presence of the activating agent of resting T lymphocytes anti-CD3 (aCD3), bovine and salmon gelatin (Hidro). IL-6 and IFN as inflammatory factors were measured to quantify the immunoreactivity of salmon and bovine hydrogel. These results showed a higher immunereactivity of Bovine compared to Salmon.
Figure 11:
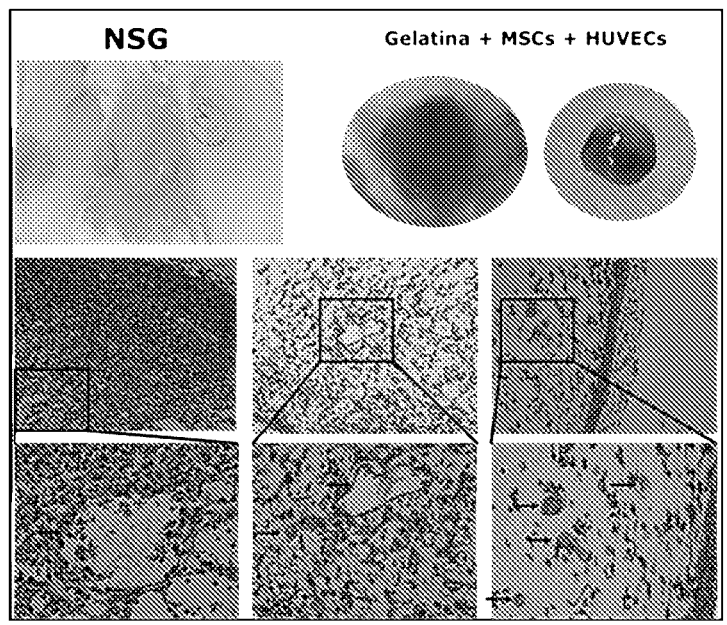
FIG. 11. Subcutaneous implantation of salmon hydrogels after 3 weeks showed a full vascularization inside the hydrogel, cell invasion from surrounding mouse cells. Arrows indicate blood vessels inside the implanted hydrogel. These results showed a very good tissue integration of the hydrogel.

Such mechanical properties can be tuned within the range of 5 kilopascals to 700 kilopascals. Therefore, in a concentration range of the methacryloyl gelatin polymer, with a variable degree of functionalization at the acidic side chains, especially lysine, from 5% to 100% and a temperature pre-treatment before crosslinking within the range 1° C. to 12° C. during a variable time below 4 hours, different physicochemical and biological properties of the polymerized/crosslinked biomaterial can be tuned. For example, the delivery rate of encapsulated soluble factors to control micro-environment around the hydrogel as shown in FIG. 8, or the proliferation of encapsulated cells as shown in FIG. 9. Other physicochemical and biological properties of the polymerized/crosslinked biomaterial that can be tuned are:
- Cell invasiveness within the biomaterial;
- Time of passive degradation;
- Time of active degradation by cell activity (secretion of enzymes);
- Remodeling capability;
- Cell adhesion; and
- Immunogenicity.
- Capacity of angiogenesis formation within the material when is implanted in vivo
- Capacity of tissue integration when implanted (very related to angiogenesis capacity)

Consequently, as shown above, a solution comprising an amino acidic chain gelatin polymer, derived from natural sources of cold-adapted marine species, in particular from the genus *Salmo* and *Oncorhynchus*, and chemically functionalized to become reactive to polymerization or cross-linking in presence of free radicals, at a concentration of about 1% to 20% (w/v), provides for a composition with improved properties in comparison to other amino acidic polymer-based biomaterials derived from mesophilic species such as mammalians and also, surprisingly, in comparison to non-methacrylated salmon gelatin (SG).

Accordingly, in a further aspect, the invention is directed to a process comprising the following steps:
i. subjecting a composition comprising a solution which in turn comprises an amino acidic chain gelatin polymer chemically functionalized to become reactive to polymerization or crosslinking in presence of free radicals, at a concentration from 1% to 20% (w/v), to temperatures lower than the gelling point of the gelatin polymer thus inducing physical crosslinking; and
ii. inducing covalent crosslinking of the physically crosslinked chemically functionalized polymer obtained in step i);

wherein said gelatin polymer is derived from natural sources, preferably from cold-adapted marine species as described herein.

A person skilled in the art will know how to determine the gelling point, which may be for instance determined by differential scanning calorimetry on cooling. The gelling point can depend on the specific fish species, but typically cold water adapted species have a gelling point lower than 10° C.

A polymerizing initiator may be present in the solution in step i) or be added prior to conducting step ii): Preferably, said solution in step i) further comprises a polymerizing initiator.

In a particular embodiment, optionally in combination with one or more of the features described above or below, the polymerizing initiator is a chemical photoinitiator and is preferably found at a concentration of 0.5%, and wherein step ii) comprises exposing the solution comprising the chemically modified amino acidic chain and a chemical photoinitiator to light, visible, UV light or infrared depending on the nature of the photoinitiator, to provide a cross-linked composition.

In step i) the composition is subjected to temperatures lower than the gelling point of the gelatin polymer typically from 1° C. to 12° C. (preferably about 4° C.), for less than 4 hours, preferably for 2 hours.

In a preferred embodiment, optionally in combination with one or more of the features described above or below, the composition of step i) is obtained by a method comprising the following steps:
a. obtaining an amino acidic chain gelatin polymer derived from natural sources of cold-adapted marine species, preferably from the genus *Salmo* or *Oncorhynchus*, and dissolving it in a solvent to a final concentration between 1% and 20% (w/v);
b. chemically modifying the primary structure of the amino acidic chain gelatin polymer of step a), by adding a chemical agent capable of becoming reactive to polymerization or crosslinking in presence of free radicals;
c. removing all unreacted chemically agent from the solution of step b);
d. optionally, adding a radical-derived initiator such as photoinitiator and/or a surfactant;
e. optionally, filtering and freeze drying the resultant composition from step c) or d) if applicable.

The pH of extraction of gelatin from the skin of a cold-adapted marine species is typically between 3 and 5.5, preferably it is between 4 and 5, such as about 4.1, 4.2, 4.3, 4.4, 4.5, 4.6, 4.7, 4.8, 4.9 or 5, more preferably it is about 5.

In a further aspect, the invention refers to a composition comprising a cross-linked/polymerized gelatin polymer obtained or obtainable by a process according to the above aspect. Other features of said gelatin polymer and composition are as described herein under the first aspect of the invention.

The invention will be more readily understood by reference to the following examples. It is noted that the following examples merely serve to illustrate the invention and do not limit the same.

EXAMPLES

Example 1

Manufacture of a Solution of Methacryloyl Salmon Gelatin

Salmon Gelatin Extraction:
1. Remove all the remaining meat and scales from the salmon skin.
2. Cut the skin in small cubes squares (3-5 cm/side)
3. Add 6 mL of NaOH 0.1M per gr of skin, maintain constant agitation (900 0 rpm) at 10° C. for 1 h.→6 mL/g*500 g=3 L (measured pH=13)
4. Remove the solution and wash the skins with $dH_2O$ by filtering and soaking.
5. Add 6 mL of NaOH 0.1M per gr of skin, maintain constant agitation at 10° C. for 1 h.→3 L (measured pH=13)
6. Remove the solution and wash the skins with $dH_2O$ by filtering, rinsing and soaking the filtered skin with $dH_2O$.
CAUTION: a too extensive washing at this step may influence the pH of the acidic solution in step 7 that may lead to a higher acidity that induce partial extraction of gelatin that needs to be avoided at this stage.
7. Add then 6 mL of 0.05M $CH_3COOH$ per gr of skin, maintain constant agitation at 10° C. for 1 h. (measured pH=3.3)
8. Wash the skins with $dH_2O$ first and submerge them in $dH_2O$, 6 ml per gr of skin.
9. Set the pH to 4.0 by adding $CH_3COOH$ drop wise.
10. Incubate for 4 h maintaining constant agitation and 60° C.
11. Check the pH and temperature every 60 minutes.
12. Remove the skins from the solution.
13. Filter the solution using a vacuum pump and filter paper 22 µm.
14. Dry the gelatin solution for 48 h at 60° C. by putting it in drying pans.
15. Ground the gelatin films into powder.

Salmon Gelatin Functionalization with Methacryloyl Groups

Methacryloyl salmon gelatin, was synthesized after mixing methacrylic anhydride, and reacting with amino groups, mainly lysine, from a gelatin solution as previously described (Nichol et al. 2010; Van Den Bulcke et al. 2000). Briefly, the grounded salmon gelatin was dissolved to a final concentration of 10% (w/v) in PBS 1× (pH 7.4) at 60° C. After fully dissolved, while still stirring, methacrylic anhydride (276685, Sigma, USA) was added slowly to a final concentration of 8% (v/v). Different levels of methacryloyl functionalization require different concentrations of methacrylic anhydride. After 3 hrs of reaction, 5× dilution in PBS 1× was performed and the reacted gelatin dialyzed against deionized water at 40° C. for 1 week. Daily replacements of fresh deionized water were done to remove all unreacted methacrylic anhydride during dialysis. Finally, the dialyzed mixture was filtered using 8 µm porous filter paper, and freeze dried before storage.

Example 2

Manufacture of a Solution of Methacryloyl Bovine Gelatin

Similarly to example 1, methacryloyl bovine gelatin was synthesized after mixing methacrylic anhydride, and reacting with amino groups, mainly lysine, from a gelatin solution as previously described (Nichol et al. 2010; Van Den Bulcke et al. 2000). Briefly, bovine gelatin (Bloom 220, Rousselot, Netherlands) was dissolved to a final concentration of 10% (w/v) in PBS 1× (pH 7.4) at 60° C. After fully dissolved, while still stirring, methacrylic anhydride (276685, Sigma, USA) was added slowly to a final concentration of 8% (v/v). Different levels of methacryloyl functionalization require different concentrations of methacrylic anhydride. After 3 hrs of reaction, 5× dilution in PBS 1× was performed and the reacted gelatin dialyzed against deionized water at 40° C. for 1 week. Daily replacements of fresh deionized water were done to remove all unreacted methacrylic anhydride during dialysis. Finally, the dialyzed mixture was filtered using 8 µm porous filter paper, and freeze dried before storage.

Example 3

Manufacture of a Solution of Non-Methacryloyl Salmon Gelatin

Salmon gelatin is extracted as explain in example 1 and non-methacryloyl salmon gelatin is usually prepared by dissolving the obtained gelatin to a final concentration of 10% (w/v) gelatin in PBS 1× (pH 7.4) at 60° C. Solutions having different concentrations of gelatin require the dissolution of different amounts of grounded gelatin in PBS 1×.

Example 4

Composition of the Invention and Its Use in Biomedicine

4.1. Materials and Methods

Extraction of Salmon Gelatin.

80 kg of salmon skins were received from the salmon farm called Los Fiordos Ltda. and kept frozen at −20° C. on 10 Jan. 2016. After a controlled thawing step, the remaining meat residues and scales were manually cleaned off. To date, 5 rounds of cleaning have been performed, processing 5 kg of skin each time, with an approximate yield of 17% of clean skins (850 gr). The skins are then cut into pieces having a 4 $cm^2$ surface area. An extraction protocol previously established by Professor Javier Enrione's laboratory was carried out, consisting of two pre-treatment steps with 0.1 M NaOH for 1 h at 10° C., each followed by a skin washing step using distilled water. A third pretreatment is performed for 1 h at 10° C. in a 0.05 M acetic acid solution and the skins are subsequently washed with distilled water. Acid extraction is finally performed, incubating the skins for 3.5 h at 60° C. in distilled water in which the pH is adjusted to different levels by adding different amounts of acetic acid. The tested pHs were 3, 4 and 5. The extracted gelatin yield, hydrolysis level of and gel strength were evaluated.

Chemical Modification of the Salmon Gelatin.

Functionalization of the salmon gelatin with methacryloyl groups to allow polymerization by means of irradiating with light is done by means of reacting methacrylic anhydride (Sigma) with the free amino groups of the lysine side chains in the gelatin. A 10% solution (w/v) comprising salmon gelatin was prepared for this purpose using 1×PBS (phosphate-buffered saline). This solution was kept at 60° C. for 1 h for complete solubilization. Different volumes of methacrylic anhydride were added drop-wise under a chemical extraction hood and under stirring (10, 5, 2, 1 or 0.5 ml are added to 100 ml of solution) and it was left to react for 3 hrs under controlled stirring and assuring that the temperature is kept at 60° C. The pH of the solution was kept at 7, otherwise it may become acidic and the degree of hydrolysis of the modified gelatin may increase.

Figure 13:
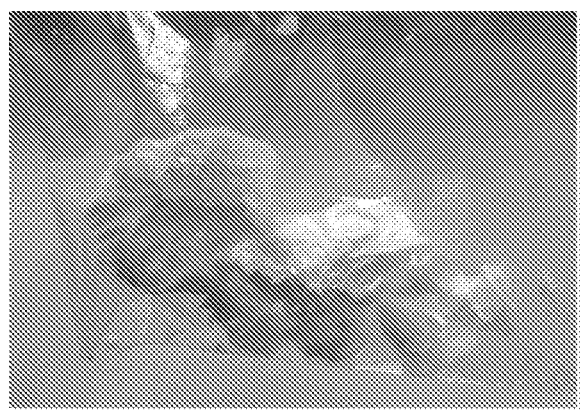
FIG. 13. Appearance of the modified and freeze-dried salmon gelatin. To prepare the bioink, this is the basic component of the formulation which is prepared at different concentrations in phosphate-buffered saline pH 7.4.

After functionalization of the salmon gelatin, the reaction mixture was diluted by adding 3 volumes of 1×PBS pH 7.4 and then dialyzed against 20 volumes of distilled water for 7 days at 40° C. changing the water twice a day. Once the dialysis process for removing unreacted methacrylic anhydride had ended, the reaction mixture was filtered through membranes with an 8 um pore size to then freeze-dry and store it at −80° C. (see FIG. 13).

Figure 14:
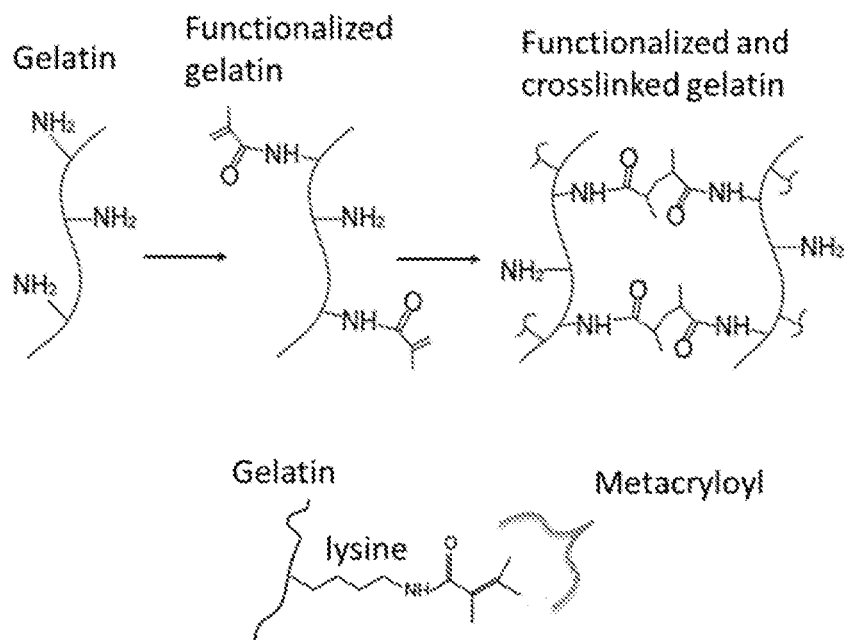
FIG. 14. Schematic depiction of the functionalization of salmon gelatin and crosslinking of modified salmon gelatin.

Once the salmon gelatin was chemically modified, the percentage of functionalized free amines or lysines was quantified using the OPA method previously described in the literature (Journal of Food Science 2001, 66(5), 642). By means of quantifying the free amines before and after the reaction, the number of lysines functionalized with the total methacryloyl groups can be determined (see FIG. 14).

Mechanical Characterization of the Salmon Gelatin Methacrylate After UV Light-Induced Crosslinking.

To induce photopolymerization, a concentration of 0.5% W/V of photoinitiator Irgacure 2919 (Sigma) was included in a solution of modified salmon gelatin (5%, 7%, 10%, 15% (w/v) in 1× PBS or distilled water) and it was irradiated with UV light (365 nm, 800 mW/cm$^2$) for 2 min in a cylindrical mold 10 mm in diameter and 3 mm tall. The modified salmon gelatin (MSG) hydrogels or scaffold formed had different mechanical properties (Young's modulus) depending on the amount of methacrylic anhydride added to the methacrylation reaction, and hence level of functionalization, and also depended on the MSG concentration used to generate the hydrogels. The mechanical tests were performed using both a DMA (Dynamic Mechanical Analyzer) and a texture analyzer. The tests were performed in both compression mode and tension mode.

Rheological Characterization of a Basic Formulation (Also Referred to Herein as "Bioink").

According to the protocols described in example 4 above, MSG with an 85% degree of functionalization in gelatin lysine residues was generated. Solutions having different modified gelatin concentrations in distilled water were prepared (5%, 10% and 15% (w/v)) to conduct the rheological studies. Viscosity data at a shear rate of 100 s$^{-1}$ were recorded using an Anton Paar MCR 301 rheometer and a conical geometry. The surface tension value of these solutions was additionally quantified using drop volume tensiometer equipment (Lauda TVT2, Dr. R. Wobser GmbH and Co., Lauda-Königshofen, Germany), which was based on the determination of the volume of a drop at the tip of a capillary perfused at a controlled speed. When the drop reached its critical volume it fell from the capillary due to gravity. The surface tension was calculated based on this critical volume, density of the solution and radius of the capillary (Food Hydrocolloids 25(5):958-967). This methodology required the precise determination of the density. This was done by means of the digital density meter (DMA 45, Anton Paar KG, Graz, Austria). These experiments were performed at the Universidad Tecnológica Metropolitana under the supervision of Professor Rommy Zùñiga.

Preliminary Measurements of the Effects of Incorporating Surfactants and Mechanical Reinforcement Components (Cellulose Nanowhiskers) on the Rheological Parameters of the Basic Bioink.

Figure 15:
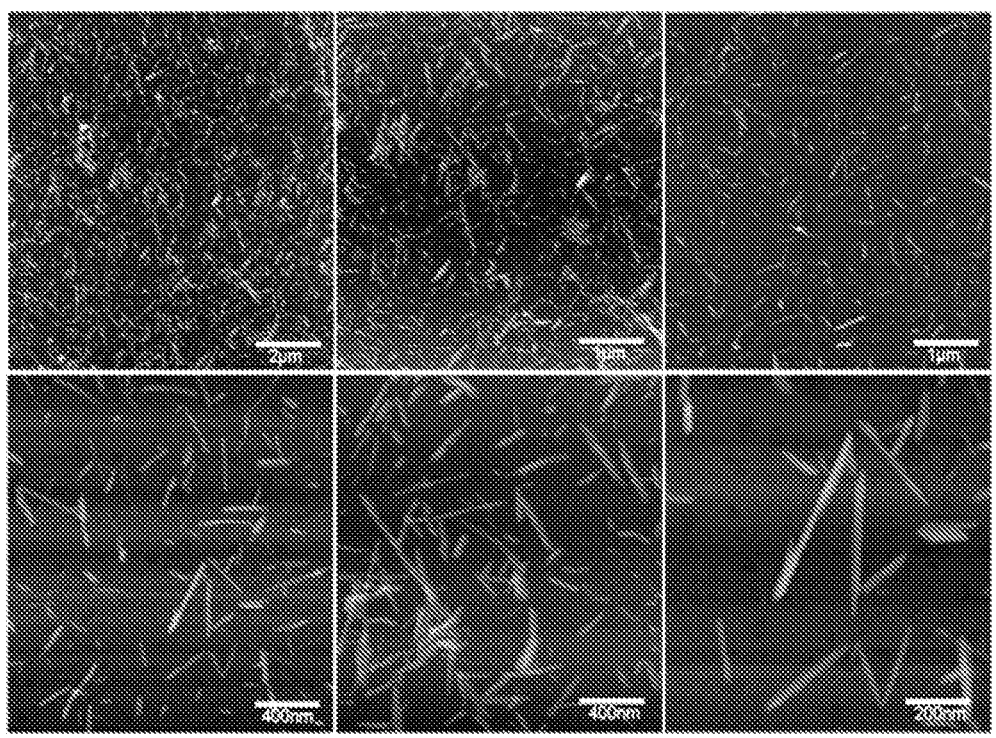
FIG. 15. Images taken by atomic force microscopy (AFM) of cellulose nanowhiskers prepared in the laboratory to be incorporated into the basic bioink (MSG functionalized at 85% and at a concentration of 10% (w/v)). These bacterial cellulose nanowhiskers were prepared under the supervision of Professor Franck Quero of the Universidad de Chile.

Measurements were taken of the viscosity and viscoelastic component of solutions comprising 15% salmon gelatin functionalized at 85% in lysine residues, additionally supplemented with 0%, 3% and 5% (w/v) of bacterial cellulose nanowhiskers. The experiments were performed with an Anton Paar MCR 301 rheometer using a conical geometry (see FIG. 15).

Development of Crosslinking Strategies of Gelatins Modified in the Crosslinking Process.

One of the natural activities of unmodified gelatin polymers when they are subjected to temperatures that are lower than gelling point temperatures is the formation of triple helixes of polymers resulting in the formation of thermoreversible hydrogels. In other words, once the hydrogels are formed at low temperatures, they can return to their liquid state when they are subjected to higher temperatures. One of the proposed strategies for improving the mechanical properties of crosslinked hydrogels is to allow the formation of triple helixes induced by low temperature before inducing light-mediated crosslinking. This allows forming more ordered and mechanically reinforced molecular structures before setting the conformation by means of establishing covalent bonds formed by light induction. This strategy allowed obtaining a 20-fold increase of post-polymerization mechanical properties compared with crosslinking without inducing the formation of tripe helixes. These increases were not seen before by means of any other technique, which holds excellent promise for being transferred to patients and the market, given that despite their good bioactivity, one of the weaknesses of these hydrogels as a material are their low mechanical properties. The mechanical properties were measured by means of compression testing using a texture analyzer. Solutions at a concentration of 10% (w/v) of modified gelatin having different degrees of functionality in the lysine residues were prepared (22% and 90%) and incubated at 4° C. for 2 h before inducing light-mediated crosslinking. The mechanical properties of the hydrogels subjected to pre-cooling steps were compared to those that were not.

Optimized Biomaterial Biocompatibility Study.

Proliferation of Human Umbilical Vein Endothelial Cells (HUVECs) Encapsulated in Hydrogels Formed with Modified Salmon Gelatin with Different Degrees of Functionalization.

Figure 16:
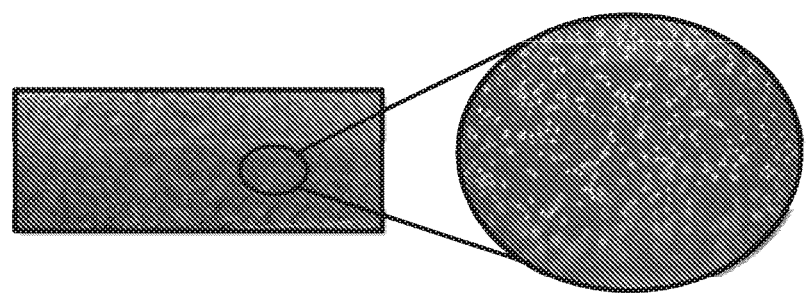
FIG. 16. Microscopic image of cells encapsulated in crosslinked hydrogels of modified salmon gelatin functionalized in 80% of their lysines with methacryloyl.

As described above, salmon gelatin-based hydrogels modified to different levels of functionalization of their lysines (20%, 50%, 60%, 80% and 90%) were prepared together with the photoinitiator as described above in the report (l.c.). Before photopolymerizing or crosslinking the hydrogels, they were mixed with HUVEC cells at a final concentration of 6×10$^6$ cells/ml. The hydrogels were incubated in DMEM culture medium supplemented to 10% in FBS, 1% Pen/Strep and 1× glutamine. The medium was changed every 2 days and kept in a cell incubator at 37° C. and 5% $CO_2$. Proliferation of the encapsulated cells was evaluated using the WST-1 Cell Proliferation Colorimetric Assay Kit (K302, Biovision, USA) according to the suppliers' instructions. In short, this assay quantifies the metabolic conversion of WST-1 to formazan, which is mediated by mitochondrial dehydrogenases of the cells (see FIG. 16).

Immune Response of the Modified Salmon Gelatin Subcutaneously Implanted in a Murine Animal Model.

Figure 17:
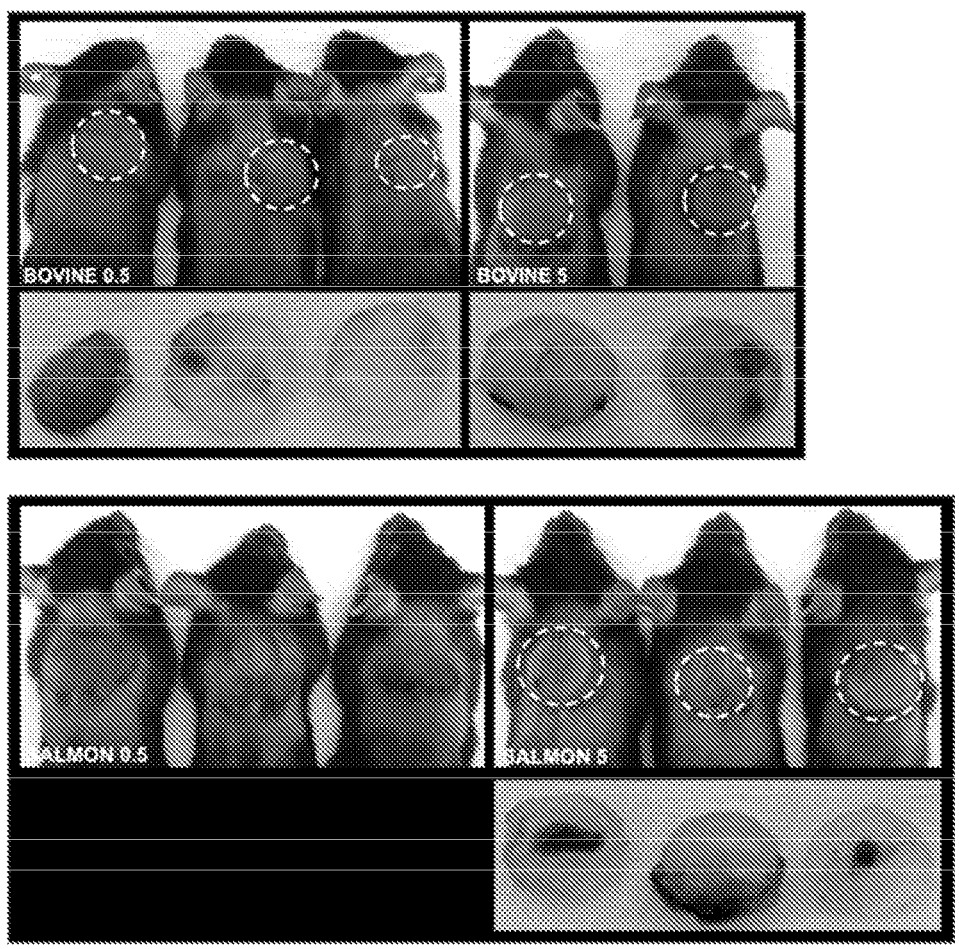
FIG. 17. C57BL/6 mice with 7-day hydrogel implants bovine and salmon gelatin-based modified to levels of lysine functionalization of 20% and 80% (referred to as 0.5 and 5, respectively). The hydrogels explanted after 7 days are seen to have a significant presence of vascular irrigation. The modified 20% salmon hydrogels could not be explanted because they had a higher level of tissue integration and remodeling thereof, and no defined presence of this tissue was observed in the back of the mouse.

Modified salmon hydrogels with different levels of lysine functionalization (20% and 80%) were prepared. The dimensions of the cylindrical hydrogels were 10 mm in diameter and 3 mm tall. These were implanted subcutaneously in the back of C57BL/6 mice. They were removed after 7 days to analyze the immune response. In short, the immune cells present in the lymph glands and the cells that migrated or that were integrated in the hydrogels were analyzed, and the inflammation level in response to the presence of this hydrogel was evaluated. All the experiments were performed such that they were compared with hydrogels manufactured with bovine gelatin with the same levels of functionalization (see FIG. 17).

Capacity of Cell Invasion in Hydrogels Formed from the Salmon Gelatin Functionalized to Different Levels.

One of the relevant points in the design of the bioink for manufacturing cellularized 3D structures is that the encapsulated cells must be able to respond biologically by migrating, remodeling the actual hydrogel, and allow other cells close to the 3D construct implantation area to migrate and interact with the implant, for example by means of forming vasculature. To evaluate this on a preliminary level, assays on cell invasion through salmon gelatin hydrogels modified by means of functionalization to different levels were performed. These results were also compared with the results obtained using bovine gelatin modified. Basically, the assay involved the use of a transwell device. Said device has two chambers, a top chamber and a bottom chamber bounded by a membrane with an 8 um pore size through which the cells migrate from one chamber to another mediated by an attractant stimulus present in the bottom chamber. A hydrogel is deposited on the membrane with a thickness of about of 1 mm and the cells are seeded on the hydrogel. The cells used are bone marrow-derived mesenchymal stem cells as a cell model used in tissue engineering. The cells that could be seen on the membrane from the top of the bottom chamber part of the of the bottom chamber had to migrate through the hydrogel and the porous membrane. Quantification of the number of migrated cells proves the capacity of the cells to migrate in the hydrogel.

4.2. Results

Chemical Modification of Salmon Gelatin.

Figure 18:
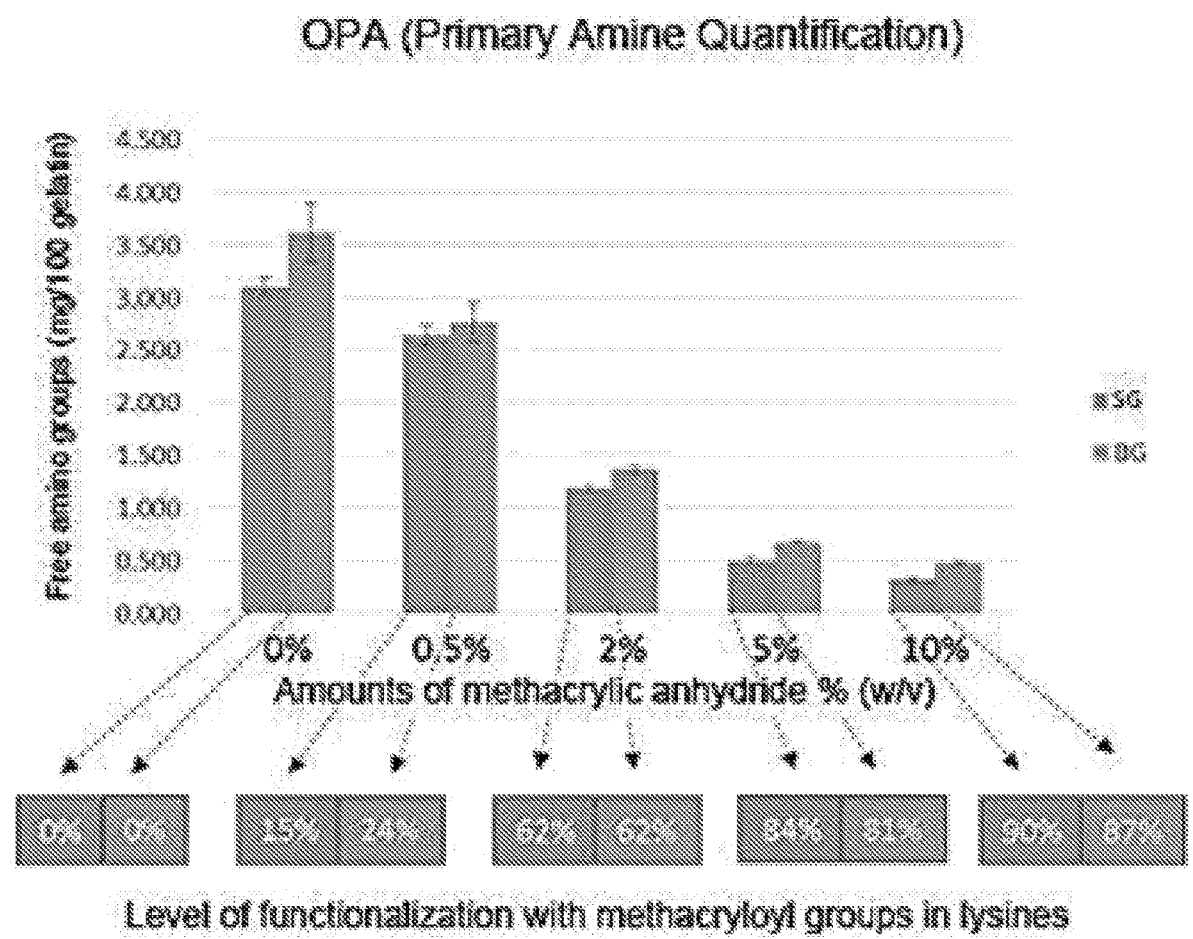
FIG. 18. Quantification of primary amines in modified gelatins. The amount of methacrylic anhydride added in the chemical functionalization reaction is expressed as a percentage, where a certain amount of methacrylic anhydride in grams is added to 100 ml of gelatin (bovine or salmon) solution at a concentration of 10% (w/v). The percentage of lysine functionalization of each gelatin is calculated as the percentage of non-quantifiable lysines by means of the OPA method with respect to the same gelatin but not functionalized.

The chemical modifications of the salmon gelatin by means of the functionalization with methacryloyl groups in the gelatin lysines were checked by means of the OPA method previously described in the literature (Journal of Food Science 2001, 66(5), 642). Basically, this method quantifies the free amino groups or primary amines present in the gelatin polypeptide chain by means of a specific reagent. The reactive free amino groups for the reaction with the OPA method for the most part come from the lysine side chain, and a small percentage (2-4%), depending on the degree of hydrolysis, corresponded to the N-terminal amino of the polypeptide chain of the molecule. The reaction of functionalization with methacrylic anhydride incorporates the methacryloyl functional group in the lysine primary amine, not allowing their reaction with the OPA reagent at the time of quantifying the number of free aminos (see FIG. 18).

Mechanical Characterization of Methacrylated Salmon Gelatin After UV Light-Induced Crosslinking.

Figure 19:
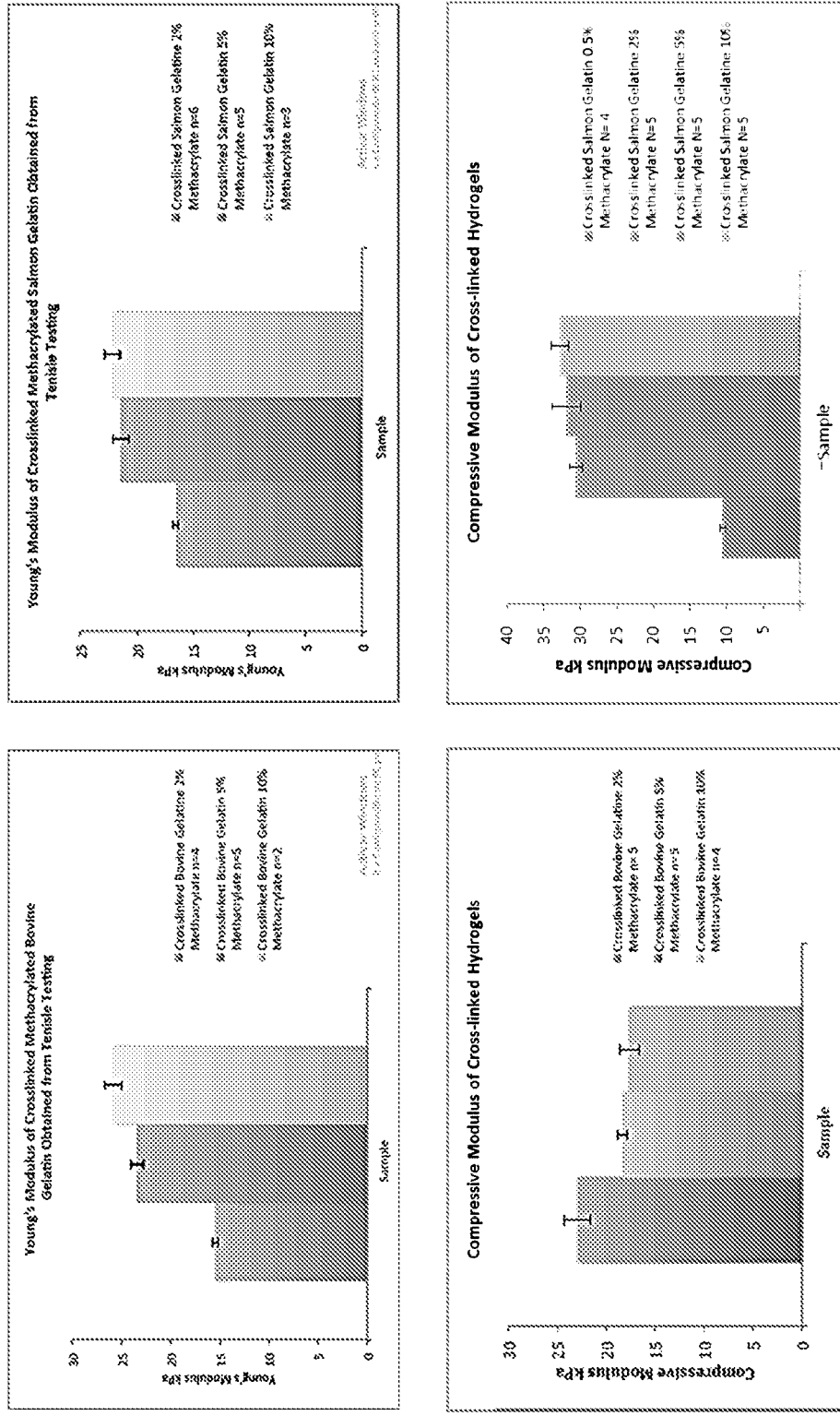
FIG. 19. Young's modulus and Compressive modulus for hydrogels formed from modified salmon and bovine gelatin at different levels of lysine functionalization with methacryloyl groups. All the hydrogels were manufactured from 10% (w/v) gelatin solutions and irradiated with the same dose (365 nm, 800 mW/cm$^2$ for 2 min). 0.5%=20% functionalization; 2%=60% functionalization; 5%=80% functionalization; 10%=90% functionalization.

As mentioned in previous sections, level of functionalization with methacryloyl groups in gelatin lysines should conceptually determine on a certain level the mechanical properties of the hydrogels formed by inducing their crosslinking. The higher the number of methacryloyl groups, the higher the number of covalent inter and intra-molecule bonds formed at the time of inducing crosslinking. This higher level of crosslinking in the hydrogels would bring about an increase in the mechanical properties of the constructs (*Young's modulus and Compressive modulus*). The results of mechanical properties for hydrogels manufactured from a 10% (w/v) modified gelatin solutions at different levels of functionalization and identical light-induced crosslinking of the methacryloyl groups are shown in FIG. 19. These parameters were compared for salmon and bovine gelatin (see FIG. 19).

Interestingly enough, no differences in the compressive moduli (measured by means of compression testing) were observed when the hydrogels had different levels of functionalization, while Young's moduli (measured by means of tensile testing) showed an increased as the level of functionalization was greater.

Rheological Characterization of a Basic Formulation of the Invention.

The droplet formation in the inkjet (Polyjet) printing process depends on rheological properties. The main objective of the rheological study was to acquire the initial values to perform a first optimization step of a new formulation according to the pre-defined multifactorial experimental design.

Gelatin is a proteinaceous biomaterial derived from the partial degradation of collagen, capable of forming a thermoreversible physical lattice. As the chains of the gelatin are cooled, they experience a conformational transition from amorphous to helicoidal (triple helix) to form the lattice bonding points. That study concentrated on the effect of the molecular characteristics of gelatin through functionalization with methacryloyl groups and their rheological behavior.

Rheology is the study of how a material deforms and flows; it includes elasticity, plasticity and viscosity.

Some of the most important rheological properties are:

Apparent viscosity (relation between shear stress and shear rate)

Storage modulus and loss modulus (linear viscoelastic behavior)

Transition temperatures.

In that study, all the rheological measurements were taken with an Anton-Paar MCR301 stress-controlled rheometer (Anton-For, Graz, Austria).

Due to the low viscosity values expected for salmon gelatin, different geometries were used to analyze their effect on measurement precision and sensitivity.

Measuring Geometries

Figure 20:
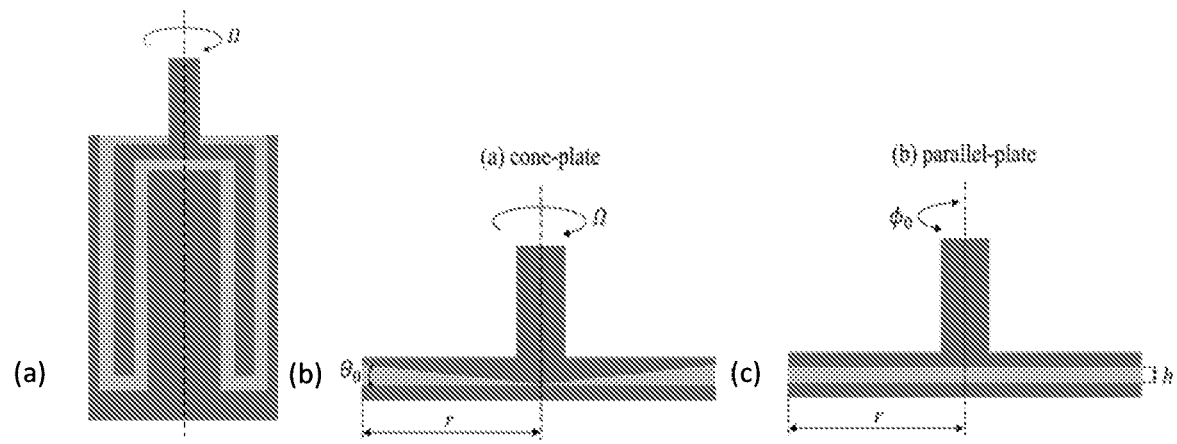
FIG. 20. Measuring geometries. (a) Double Gap, (b) Cone-plate (c) Plate-plate.
Figure 21:
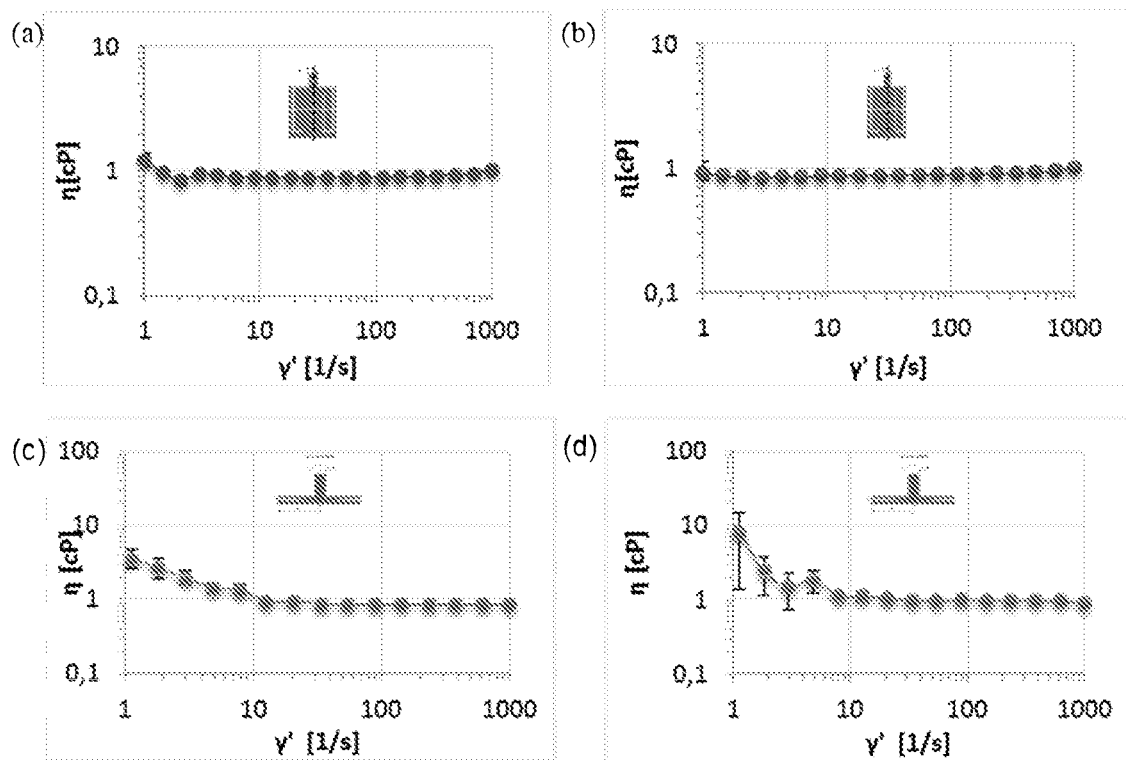
FIG. 21. Viscosity of water (a,c) and 1×PBS (b, d) at a different shear rate calculated at 25° C. with double gap geometry (a, b) and cone-plate geometry (c, d).
Figure 22:
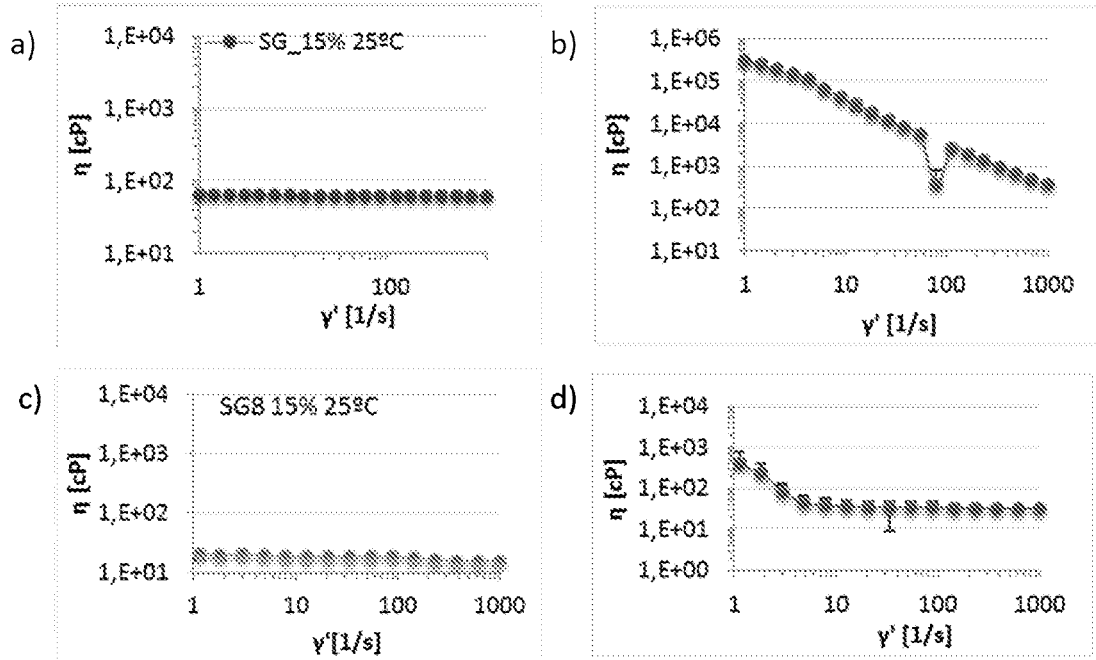
FIG. 22. The double gap geometry allows obtaining a more suitable description of the Newtonian behavior of salmon gelatin and a smaller variation between different measurements. At 25° C., the double gap geometry allows best observing the essential difference between the bovine and salmon gelatin samples. The bovine gelatin is in gel state, as the formation of triples helixes is observed at around 25° C.
Figure 23:
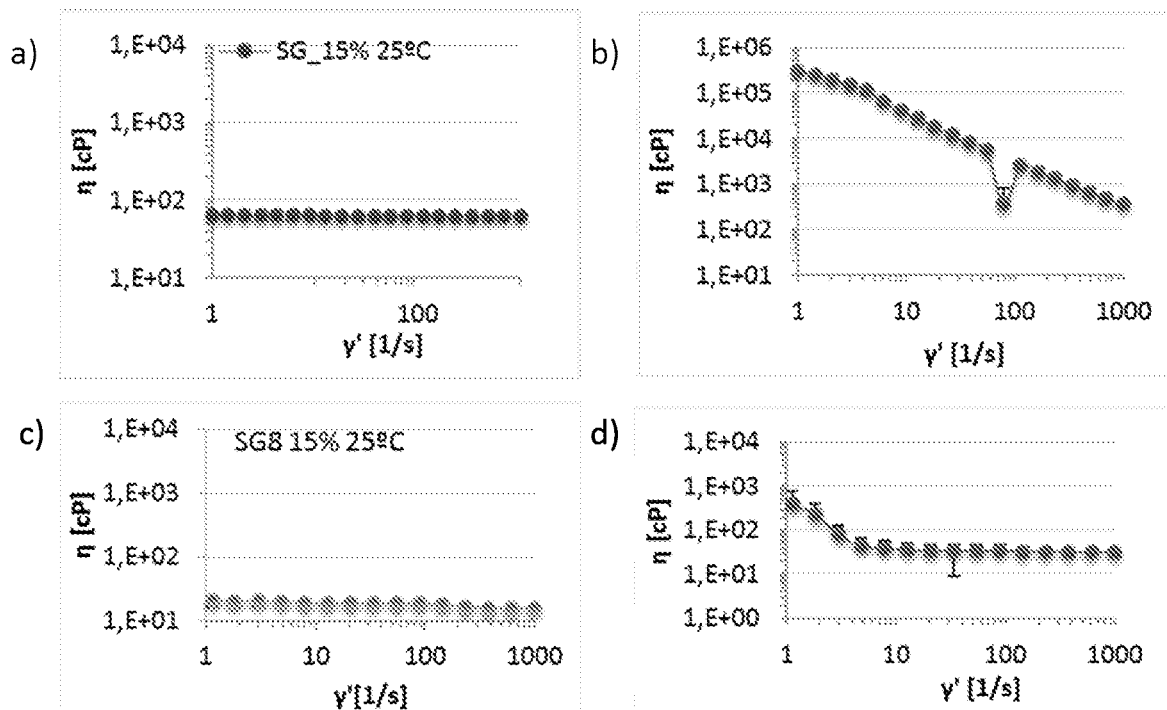
FIG. 23. Viscosity of salmon gelatin (a,c) and bovine gelatin (b,d) according to the shear rate at 25° C. calculated with double gap geometry (a,b) and cone-plate geometry (c,d).
Figure 24:
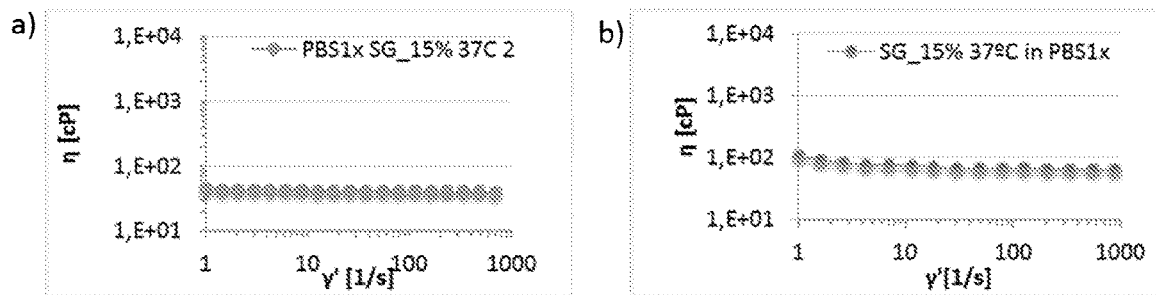
FIG. 24. Viscosity of salmon gelatin according to the shear rate at 37° C. calculated with double gap geometry (a) and cone-plate geometry (b).
Figure 25:
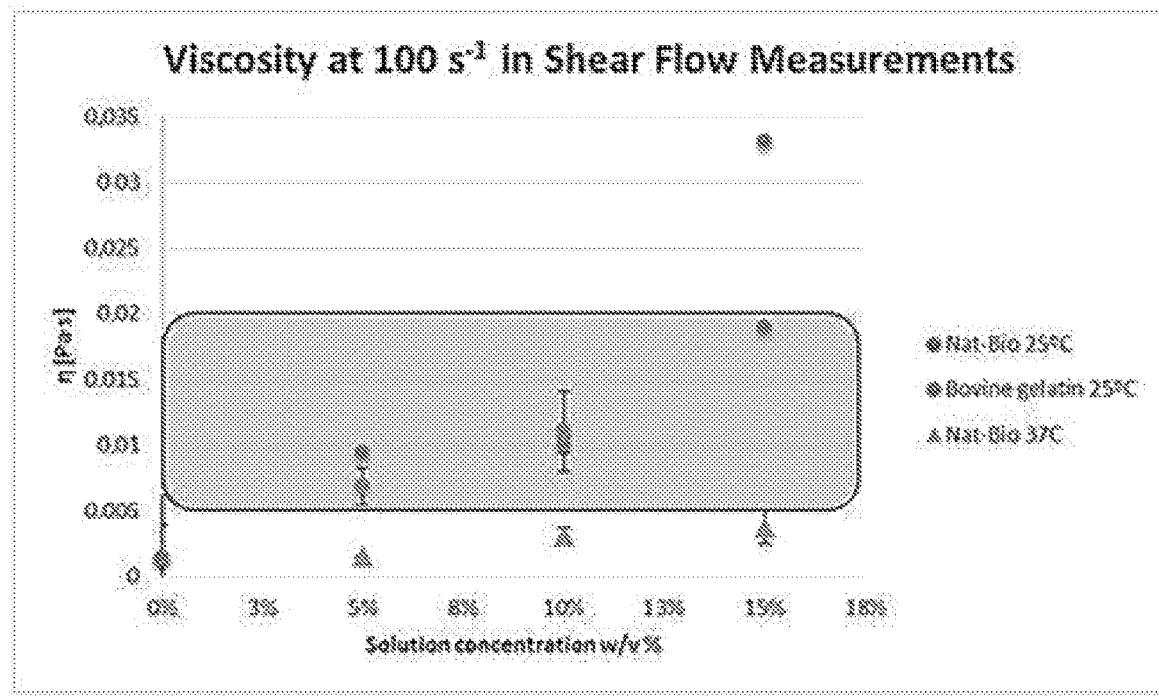
FIG. 25. Viscosity of salmon gelatin (Nat-Bio=salmon gelatin with 85% functionalization in lysines) and bovine gelatin functionalized and calculated at a shear rate of 100 s$^{-1}$. The bound area corresponds to the viscosity values allowed by the Polyjet equipment. Each experiment was replicated 3 times to obtain the average and respective standard deviation.

Double Gap (above in FIG. 20a)). Geometry providing better measurement sensitivity in the event of low stress because the area of contact with the sample is very large. Otherwise, more material is needed for each measurement (10 mL vs. 300 μL in cone-plate) and the rapid temperature control is limited due to the amplitude of the surface of the geometry.

Cone-Plate (FIG. 20b)). Optimal geometry which provides a homogenous distribution of shear stresses as a result of the angle of the cone. It is not as sensitive as the double gap, but it, too, allows good measurements also with low viscosity materials. It is not recommended for particle systems. A cone-plate with an angle of 0.5° and 50 mm in diameter was used for these viscosity measurements.

Plate-plate (FIG. 20c)): This is the most flexible geometry as it allows regulating the amplitude of the gap, quick temperature changes and shear rate. Measurement sensitivity increases with the diameter of the top plate (50 mm in that study). Although the sensitivity is lower than that of the preceding geometries, this geometry allows quick and homogenous temperature control, so it was used in the gelling study.

The apparent viscosity was measured for the salmon and bovine gelatins at different concentrations from 5% to 15% (w/v) through flow scan with a shear rate between 1 and 1000 s$^{-1}$ at 25° C. and 37° C., initially comparing the measurement sensitivity of the Double Gap and cone-plate geometries. A frequency scan with a deformation of 1% and frequency between 0.1-100 Hz, and an amplitude scan with a frequency of 1 Hz and deformation amplitude between 0.01 and 100% were performed to determine the linear zone. The storage modulus G' and loss modulus G", as well as the gelling $T_g$ and melting temperature $T_m$ were extrapolated from temperature scan measurements for temperatures from 37° C. to 3° C. and from 3° C. to 20° C. by applying a deformation of 1% and a frequency of 1 Hz.

The salmon gelatin (SG) was extracted from salmon skins. The bovine gelatin (BG) derived from bovine bones by alkali processing.

The gelatin was functionalized with methacryloyl groups through the reaction with methacrylic anhydride (276685, Sigma). In short, the gelatins of salmon and bovine were dissolved in PBS (pH 7.4) at 60° C. to a concentration of 10% (w/v). Under continuous stirring, the methacrylic anhydride was added slowly to a concentration of 8% w/w. After three hours, the reaction is stopped by dilution with PBS and subsequent dialysis in distilled water for one week at 40° C. The end product (SG8 and BG8, salmon and bovine, respectively) is obtained by filtration in 8 um pores and freeze-drying.

The cellulose nanowhiskers (CNW) were obtained by acid hydrolisis of bacterial cellulose in sulfuric acid. The hydrolysis product was dialyzed to remove reaction byproducts, sonicated for re-suspension and finally purified through ion exchange resin to obtain a 0.1% solution (w/v). To obtain 3 and 5% w/w solutions in a gelatin solution, the CNWs were concentrated through a rotovapor.

Gelatin Solutions

A 15% stock solution (w/v) was prepared for each salmon gelatin (SG), bovine gelatin (BG) and the respective modified gelatins with 85% functionalization of their lysines (SG8 and BG8) by means of continuous stirring at 60° C. for 1 hour. The solutions were subsequently diluted until obtaining 10 and 5% solutions (w/v). The solutions were kept under constant stirring at 37° C. until they were measured.

Gelatin Solutions with CNW.

15% solutions (w/v) of salmon gelatin (SG) and modified salmon (SG8) supplemented with CNWs were prepared by adding 0.3 g of gelatin to 2 mL of a CNW solution containing 9 and 15 mg of CNW, respectively, to obtain solutions with concentrations of 3% or 5% (w/w) of CNW with respect to the gelatin.

At first, the effect of measurement geometry on measurement sensitivity was analyzed. The measurements, which were obtained in triplicate, show the best double gap sensitivity where the Newtonian behavior of the two fluids is described also at low shear rates.

One of the important points to be highlighted is that unlike modified bovine gelatin, the range of gelatin concentrations in the bioink that are acceptable for being used in Polyjet printers is broader for the case of salmon.

Preliminary Measurements of the Effects of Incorporating Surfactants and Mechanical Reinforcement Components (Cellulose Nanowhiskers) on the Rheological Parameters of the Basic Formulation.

Figure 26:
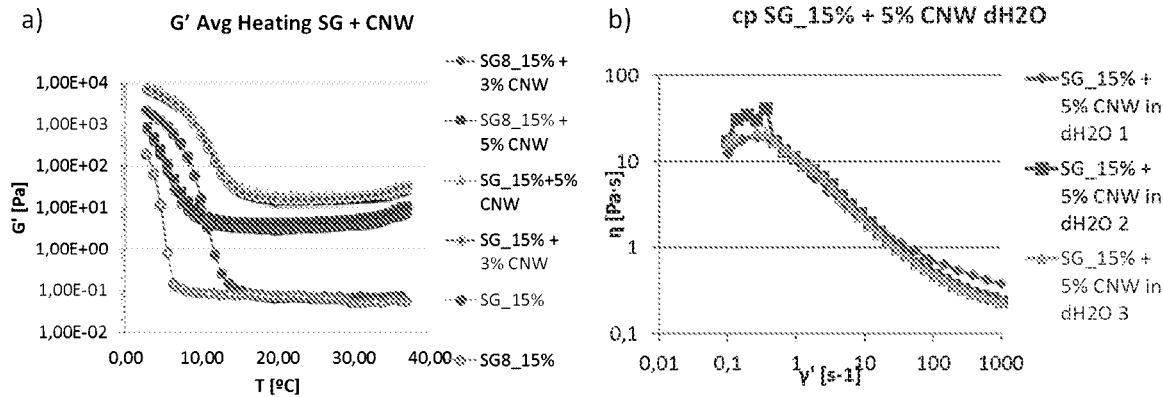
FIG. 26. Storage modulus (storage modulus) in a temperature scan for basic bioink formulation supplemented with CNWs and viscosity according to the shear rate of salmon gelatin. SG=salmon gelatin; SG8=modified salmon gelatin with a lysine functionalization of 85% with a methacryloyl group; CNW=cellulose nanowhiskers.
Figure 27:
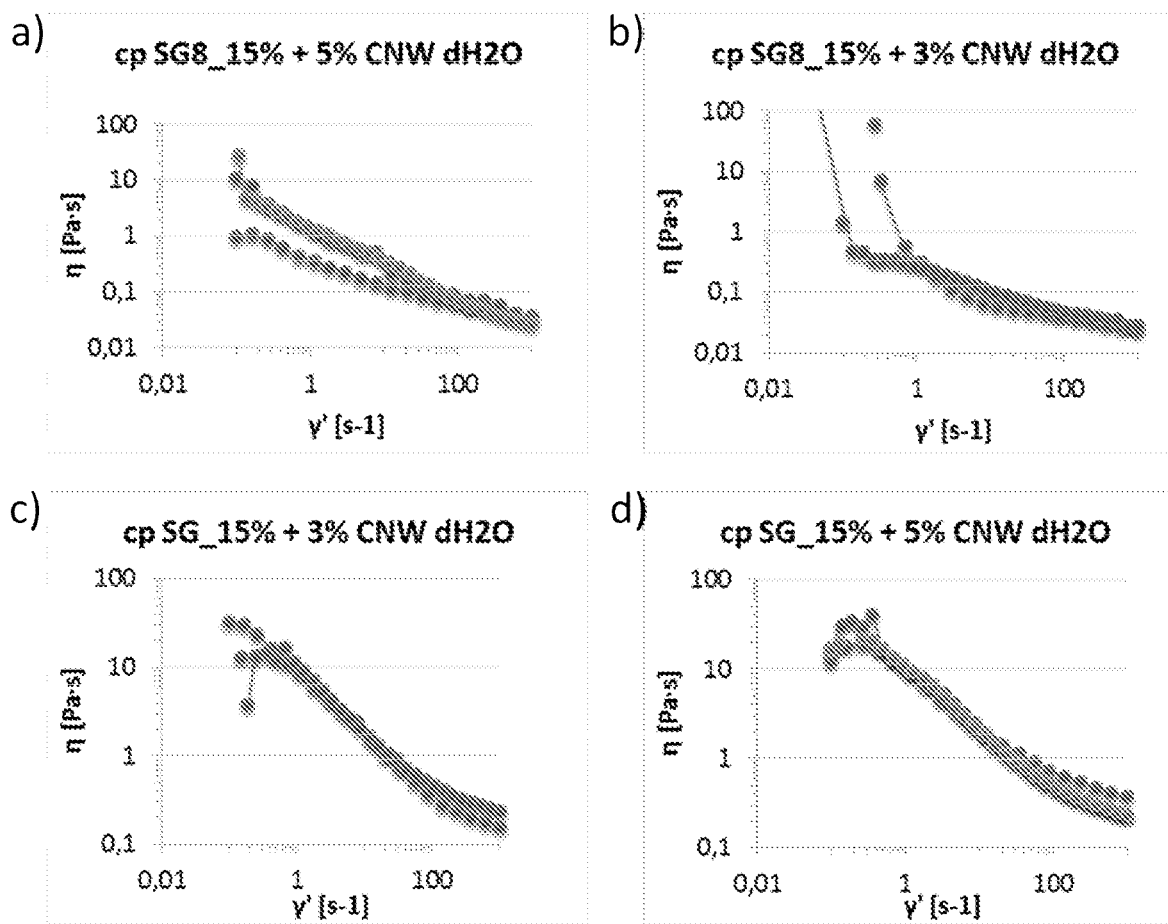
FIG. 27. Viscosity of the modified salmon gelatin compound (a,b) and non-modified gelatin (c, d) with 3% (a, c) and 5% w/w of CNW according to the shear rate at 37° C.
Figure 28:
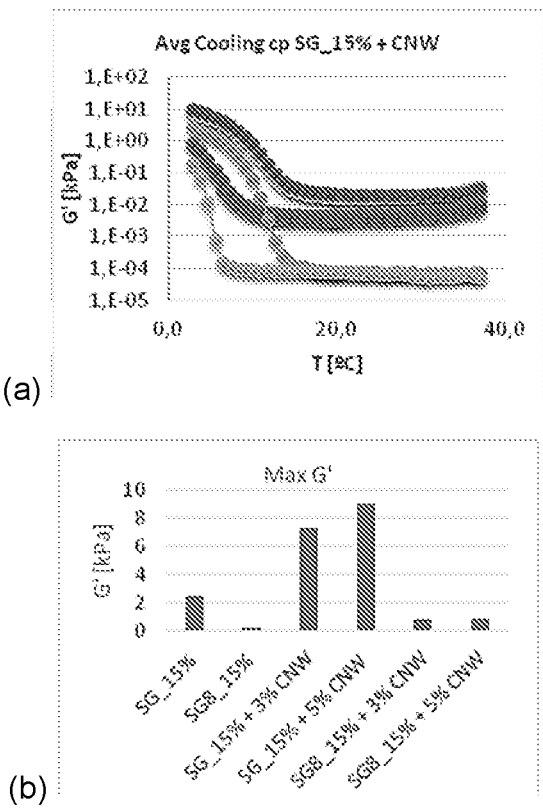
FIG. 28. (a) Storage moduli G' according to the temperature for salmon gelatin (-•-), modified salmon gelatin with a level of functionalization of 85% (-•-) and same at 3% (SG_CNW3 -•-, SG8_CNW3 -•-) and 5% (SG_CNW5 -•-, SG8_CNW5 -•-) of cellulose nanowhiskers (CNW) by applying a deformation of 1% and a frequency of 1 Hz. (b) Bar graph of the maximum storage modulus values for the different gelatins extrapolated from the curves of a).

The incorporation of cellulose nanowhiskers (CNW) in the basic formulation for the purpose of improving the mechanical properties after crosslinking can affect the final rheology of the bioink. For this reason, experiments were performed that included in the formulation a concentration of 3% and 5% (w/w) of CNW in relation to the grams of gelatin in the solution. The results showed an increase in the storage modulus in the supplemented bioink, which is interpreted as an increase of the force of interactions between the different polymers and particles in the bioink formulation. This would translate into an increase in mechanical properties, however the increase in solution viscosity leaves the bioink outside the ranges allowed by Polyjet technology. Additionally, it can be seen that a change from Newtonian behavior to non-Newtonian behavior (viscosity is inversely proportional to the shear rate applied to the fluid) by adding the nanowhiskers, which is not recommended for Polyjet equipment (see FIGS. 26, 27 and 28).

Development of Crosslinking Strategies of Gelatins Modified in the Crosslinking Process.

Figure 29:
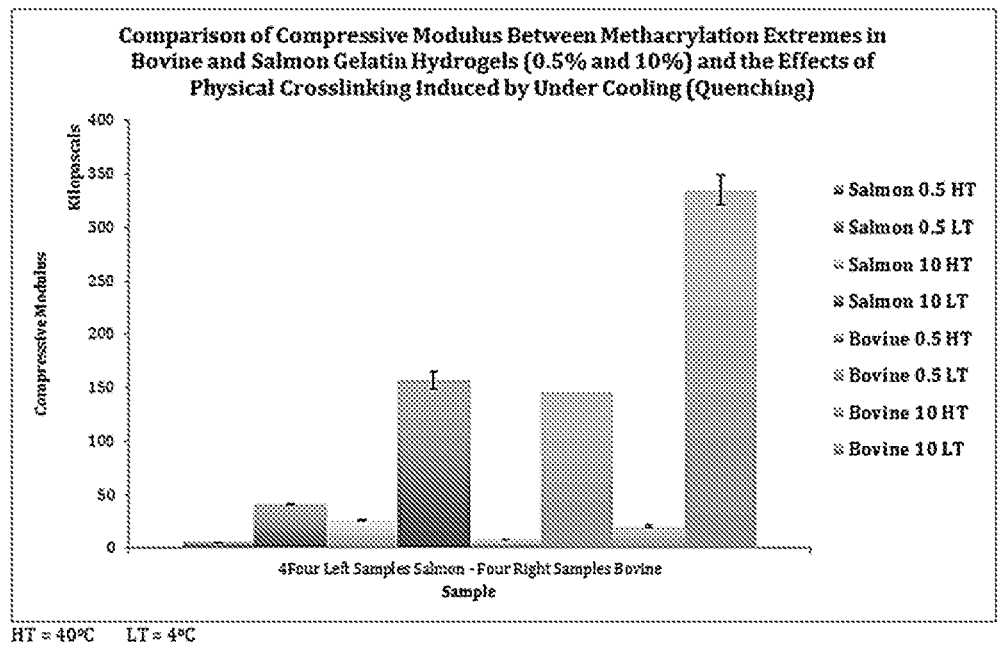
FIG. 29. Mechanical properties improved by means of pre-treatment at temperatures inducing gelling (physical crosslinking) prior to inducing covalent crosslinking of methacryloyl groups. The results were compared to pretreatment with temperatures that do not induce gelling and bovine gelatin was simultaneously compared to salmon gelatin. Note that for the case of "Bovine 0.5 LT," there is only one replica, while for the other samples, n=3. 0.5=20% functionalization of lysines; 10%=90% functionalization of lysines.
Figure 52:
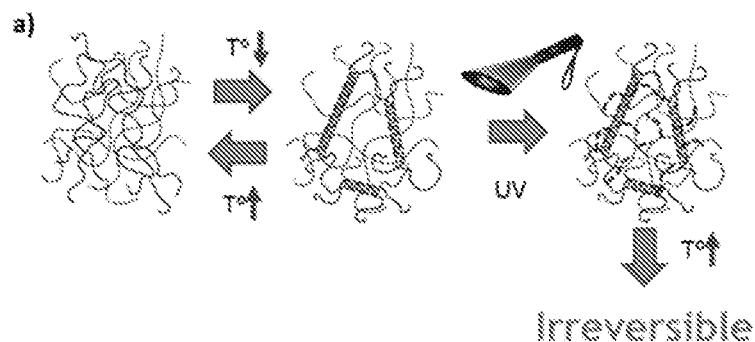
FIG. 52. A) Graphical depiction of gelatin polymers and its structural modification upon submission to cooling pretreatment and photo-crosslinking. It is shown the triple helix formation upon temperature decrease and the subsequent structural fixing through light-induced covalent linking B) Compressive Modulus testing of a 15% (w/v) solution of salmon gelatin with various degrees of methacrylation when submitted to pre-cooling.
Figure 52:
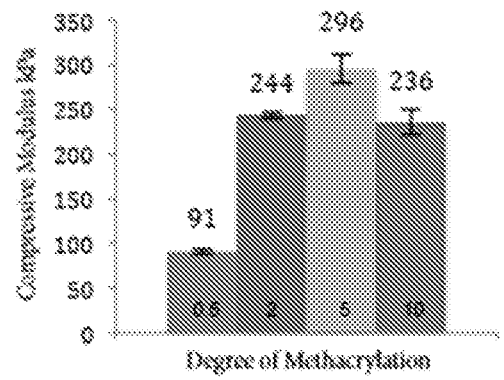

One of the main reasons for studying new strategies for reinforcing hydrogels was the fact that the incorporation of cellulose nanowhiskers changed the rheological properties of bioinks, making them unsuitable for Polyjet technology. Based on the natural understanding of thermoreversible gelling by temperature of the gelatin, where the formation of a triple helix arrangement of gelatin monomers is induced, the possibility of inducing the formation of a triple helix first (physical crosslinking), followed by inducing light-mediated crosslinking of methacryloyl groups (chemical or covalent crosslinking) was studied. As mentioned above, chemical crosslinking of the gelatin already arranged as a triple helix, fixes the triple helix structure and reinforces it, making it irreversible against increases in temperature. Surprisingly, this strategy allowed a 20-fold increase in mechanical properties, and such a level of reinforcement was not previously seen by means of other strategies studied (see FIG. 29). This is extremely relevant for applications in tissue engineering, since the mechanical properties achieved are compared with natural soft tissues, which allows in vivo implantation. New FIG. 52(a) graphically represents triple helix formation at gelling temperature and (irreversible) covalent cross-linking upon exposure to uv light. FIG. 52(b) shows the compressive modulus results (kPa) for methacrylated salmon gelatin hydrogel at 15% wherein prior to cross-linking it has been submitted to a pre-cooling treatment at 4° C. The tested gelatin has various degrees of methacrylation (0.5, 2, 5 and 10). This figure shows that pre-cooling treatment results in a reinforcement of the structural properties of gelatin hydrogels, reaching high level of compression modulus.

Optimized Biomaterial Biocompatibility Study

Figure 30:
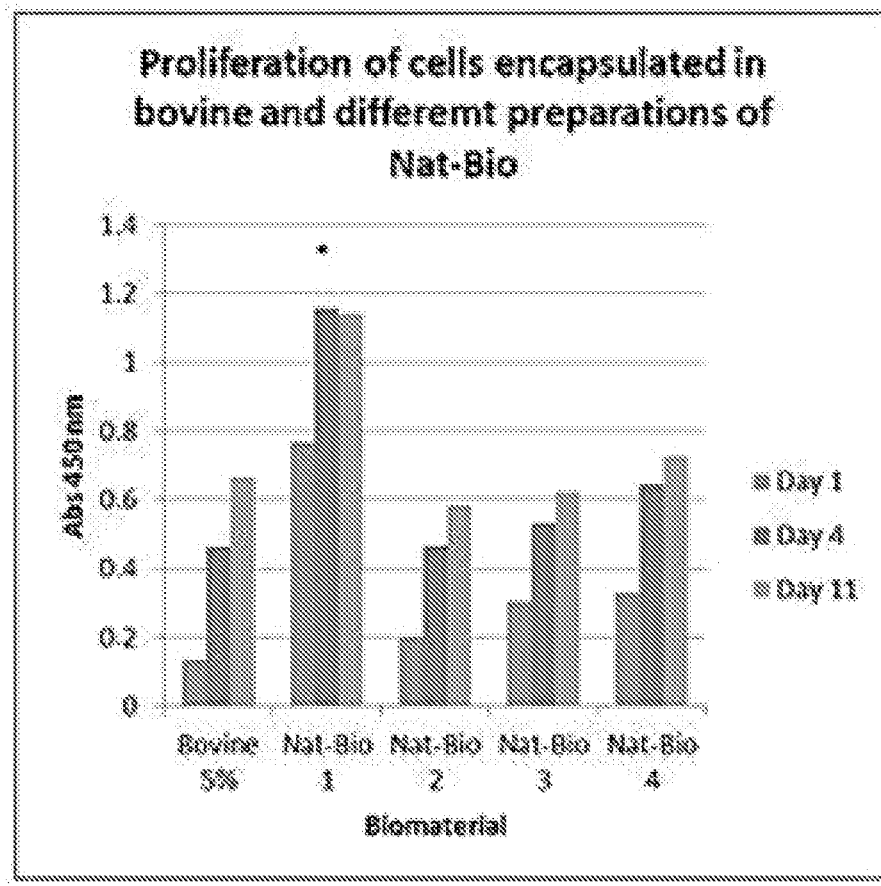
FIG. 30. Encapsulated cell proliferation evaluated by means of "WST-1 Cell Proliferation Colorimetric Assay Kit" (K302, Biovision, USA). Three experiments per condition with 3 WST-1 metabolization quantification replicas were performed. The hydrogels were manufactured from solutions of modified gelatin at concentration of 10% (w/v) in 1×PBS. Additionally, and for the sake of comparison, encapsulation in bovine gelatin hydrogels with functionalization of 80% of lysines was included. Nat-Bio 1=20% functionalization; Nat-Bio 2=60% functionalization; Nat-Bio 3=80% functionalization; Nat-Bio 4=90% functionalization.

Proliferation of Human Umbilical Vein Endothelial Cells (HUVECs) Encapsulated in Hydrogels Formed with Modified Salmon Gelatin with Different Degrees of Functionalization One of the main concerns with these processes of encapsulating cells in hydrogels or scaffolds is the state in which the cells end up after the process. For this reason, proliferation assays were performed as explained above. In this case, mitochondrial metabolism of WST-1 was quantified on day 1, 4 and 14 after crosslinking and cell encapsulation, and it was correlated with cell proliferation in the hydrogel. Higher proliferation in hydrogels with lower mechanical properties was observed, as in the case of the hydrogel based on modified salmon gelatin by means of functionalization of 20% of its lysines with the methacryloyl group. However, levels of functionalization of 60%, 80% and 90% did not show significant differences (see FIG. 30).

Immune Response of the Modified Salmon Gelatin Subcutaneously Implanted in a Murine Animal Model.

Figure 31:
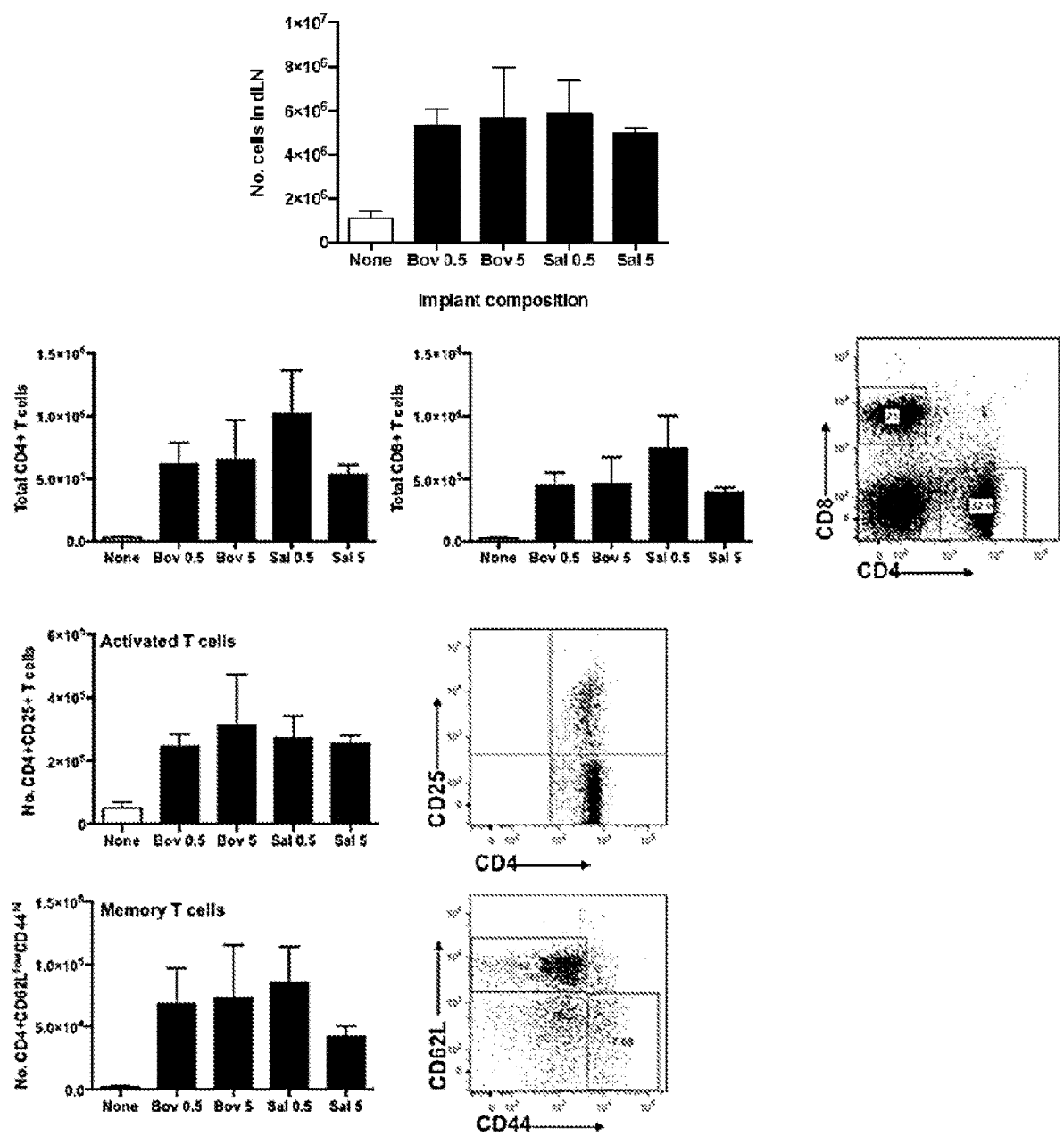
FIG. 31. Characterization of lymphoid cells present in the lymph glands irrigating the area where the gelatin hydrogels were implanted. Salmon and bovine gelatin hydrogels, and different levels of functionalization (0.5=20% functionalization; 5=80% functionalization) are compared. There are no significant differences between the different conditions 7 days after implantation, with the exception of salmon gelatin hydrogel at 20% functionalization. Given that the data is preliminary (n=2), the following experiments must be performed in the presence of a control surgical procedure in order to rule out the increase of lymphoid cells given the inflammation generated by the surgical procedure itself and not as a result of the presence of the hydrogel.
Figure 32:
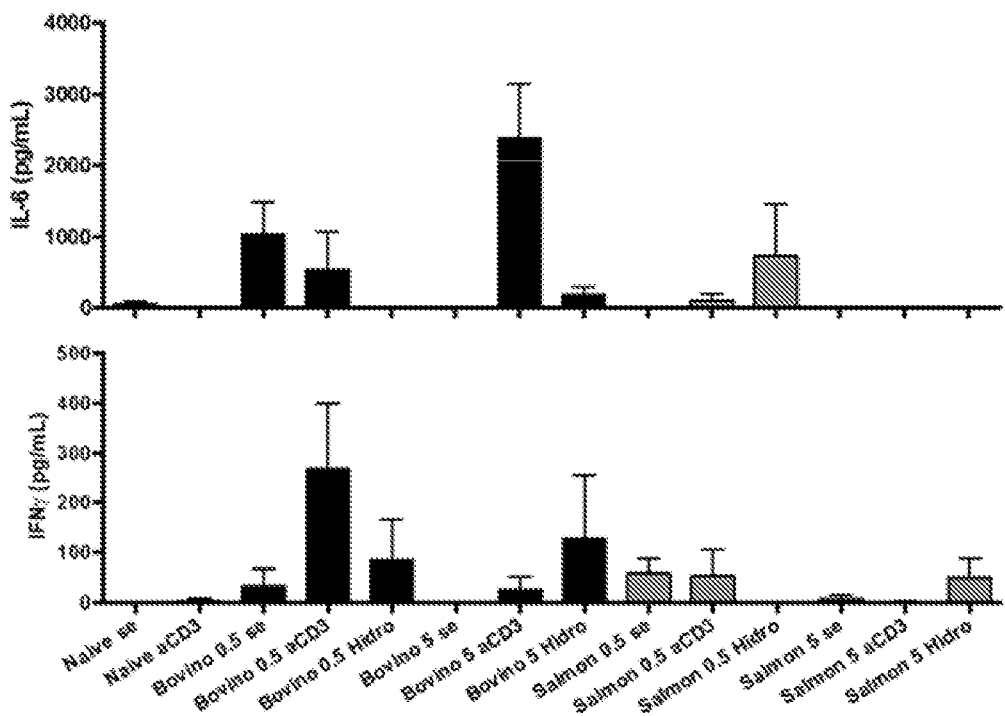
FIG. 32. Production of pro-inflammatory cytokines by the presence of modified salmon or bovine gelatin. Cells isolated from the lymph nodes of mice implanted with the hydrogels were cultured in vitro and subjected to inflammatory induction of memory by means of the presence of modified salmon or bovine gelatin. Greater immune reaction is observed when stimulated with bovine gelatin compared with salmon gelatin, and greater for the case of gelatins with a lower degree of functionalization. Naive=non-implanted mice; se=no stimulus; aCD3=general (stimulated) T cell activator; 0.5=lymphocytes from nodes of mice implanted with gelatin hydrogels functionalized at 20%; 5=lymphocytes from nodes of mice implanted with gelatin hydrogels functionalized at 80%; Hydro=memory stimulation with gelatin modified in the in vitro cultures, whether 20% or 80% stimulated; IL-6=interleukin 6; IFNgamma=Interferon gamma Inflammatory response is associated with the production of inflammatory factors (IL-6, IFNgamma).
Figure 33:
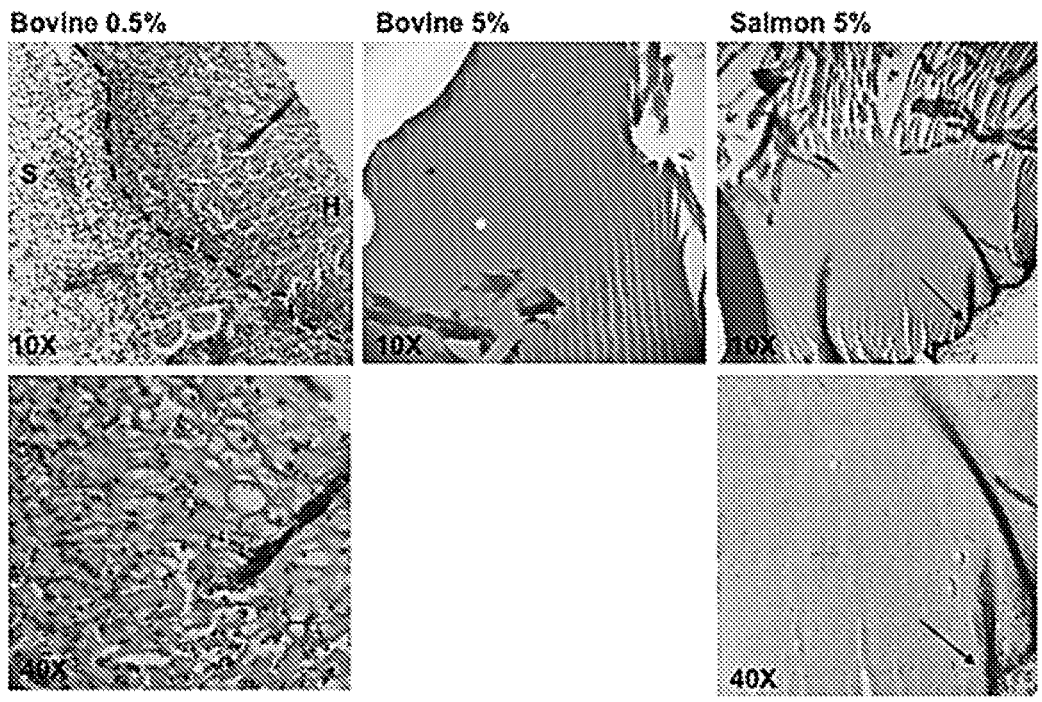
FIG. 33. Histological images of the explants of modified bovine and salmon gelatin-based hydrogels at different levels of lysine functionalization (functionalization with methacryloyl groups). For the case of gelatin-based hydrogels functionalized at 20% (0.5%), deep tissue integration, cell invasion and vascularization are observed, while for higher functionalizations (80%), the cells primarily stay in the periphery of the hydrogel. The salmon gelatin-based hydrogels functionalized in 20% of its lysines could not be recovered due to their level of remodeling. Complete tissue integration or rapid degradation of the biomaterial by the activity of cells that migrated to the area is assumed.
Figure 34:
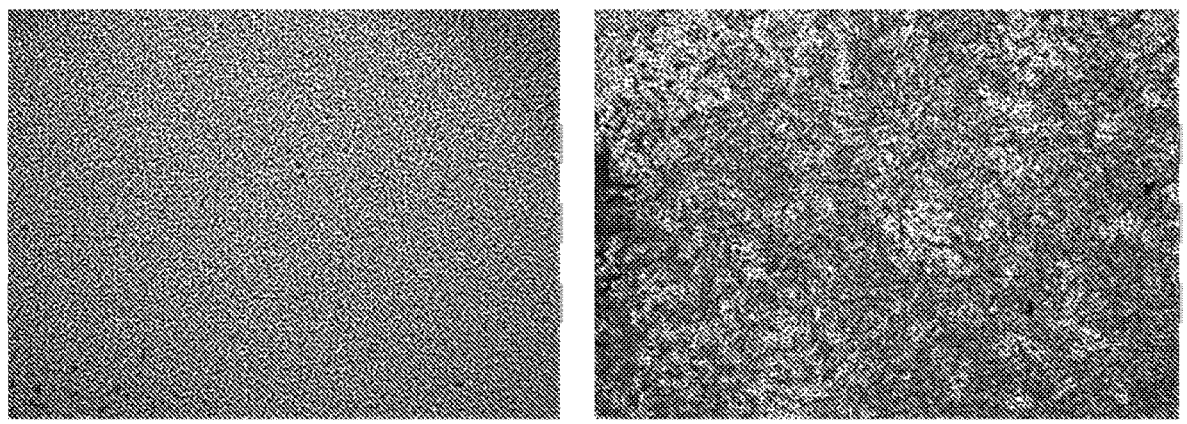
FIG. 34. Modified gelatin-based hydrogel invasion assay. These images correspond to the negative control (left) and positive control (right) of these assays. In particular, these assays are performed in Transwell devices by forming a 1 mm layer of hydrogel on the porous membrane dividing the top and bottom chambers. The hydrogels are formed from modified gelatin from a solution at a concentration of 2.4%. After the assay, the cells that migrated to the bottom surface of the porous membrane are stained blue. The negative control is performed in the presence of the migration inducer in both the top and bottom chambers (DMEM+10% FBS). The positive control is performed in the presence of the migration inducer only in the bottom chamber.

As mentioned in the preceding section of this report, the immune response against the presence of a foreign scaffold when it is implanted can be a determining factor for the success of the integration of an engineered tissue for the treatment of tissue pathologies. An immunogenic rejection can result in elimination of the hydrogel (with or without encapsulated cells) or damage to the patient due to a very widespread inflammatory response. To evaluate this, the preliminary subcutaneous implantation experiments were performed in mice with hydrogels manufactured from salmon or bovine gelatin modified by means of low functionalization (20%) or high functionalization (80%). The results generally showed higher immunogenicity associated with the presence of bovine gelatin compared with salmon gelatin, and furthermore, the immune response seems to be lower when the hydrogel is functionalized to a higher degree (see FIGS. 31 and 32). With respect to this concept, this effect can be related to the higher cell invasion capacity and vasculature formation in hydrogels that are less functionalized than those that are more functionalized, which would allow more contact of cells from the immune system with the hydrogel in the cases that are less functionalized (see FIG. 33). It should be highlighted that immune responses are generally fairly low, which corroborates earlier findings described for gelatin in general.

Capacity of Cell Invasion in the Hydrogels Formed from the Salmon Gelatin Functionalized at Different Levels.

Figure 12:
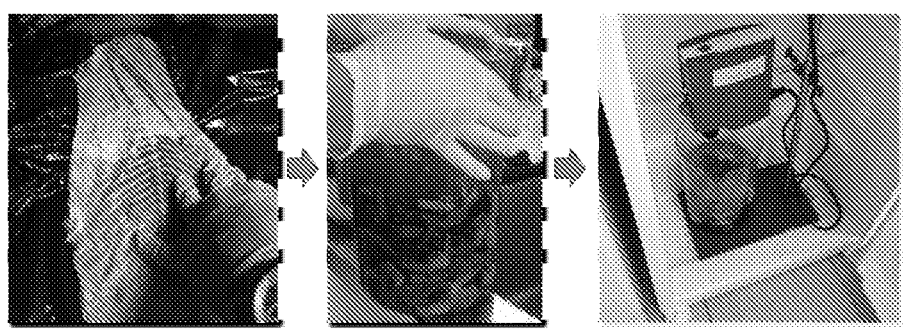
FIG. 12. Images of the process of cleaning skins and preparing solutions for pre-treatment and extraction, and an image of the incubation during pretreatments at 10° C.

The assay could be set up with respect to this subactivity, which is intended for quantifying in vitro the invasion capacity of the modified bovine and salmon gelatin-based hydrogels with different degrees of functionalization, and the experiments are currently being conducted. FIG. 12 shows the negative and positive controls of this assay, which uses hydrogels formed from gelatin solutions at a concentration of 2.4%. The negative control is performed in the presence of an inducing factor in both chambers of the Transwell, while the positive control is performed only in the bottom chamber, quantifying only cell chemotaxis and not random migration.

Example 5

Melting Characterization of Salmon and Bovine Gelatin Solutions (Functionalized and Non-Functionalized)

The melting temperature ($T_m$) and enthalpy ($\Delta H_m$) of salmon and bovine gelatin solutions (7 w/v %) were evaluated using Differential Scanning calorimetry (DSC) and are shown in Table 1. The $T_m$ of Salmon gelatin (4.2±0.026° C.) is significantly lower than the $T_m$ of Bovine gelatin (12.2±0.008° C.). When these gelatins have been functionalized, the melting temperatures decrease significantly ($p<0.05$, t-test). The $T_m$ of modified salmon gelatin is, however, much lower than for modified Bovine gelatin ($p<0.05$, t-test). This difference between $T_m$ of Salmon and Bovine gelatins can be used as a technological advantage allowing wider application windows such as tissue engineering in which biofabrication technologies require an stable liquid aggregation states within a broader range of temperature (broader processing window), for example without changing viscosity over time until gelification is to extended to perform appropriately in technological applications.

It is also important to highlight that melting transition temperature range in table 1 ($\Delta T$) proves also that the transition occurs a at more well defined temperature with allows better control of the triple helices formation hence the viscoelastic properties of the salmon gelatin compared to bovine gelatin.

TABLE 1

Melting characterization of gelatin solutions (7%).

| | Salmon Gelatin | | Bovine Gelatin | |
|---|---|---|---|---|
| | Non-functionalized | Functionalized | Non-functionalized | Functionalized |
| Tm (° C.) | 4.26 (±0.026) | 4.09 (±0.080) | 12.20 (±0.008) | 9.69 (±0.198) |
| $\Delta H_m$ (J/g) | 0.88 (±0.028) | 0.48 (±0.088) | 1.20 (±0.016) | 0.73 (±0.010) |
| $\Delta T$ (° C.) | 11.19 (±0.020) | 10.97 (±0.143) | 19.72 (±0.013) | 17.46 (±0.163) |

Results are shown as average (±standard deviation).

Example 6

Gel Strength in Non-Functionalized Salmon and Bovine Gelatin

Gel strength (bloom strength) was measured following the method reported by Wainewright (1977). Salmon and bovine gelatin gels (6.67% w/v) were prepared in Bloom jars (150 mL, Stable Micro Systems, UK) by dissolving dry gelatin in distilled water at 60° C. during 20 min and after holding the suspension at 40° C. during 40 min. The prepared suspension was held in an incubator at 3° C. during 16-18 h. Gel strength was assessed on a texture analyser TA.XTplus (Stable Micro Systems, UK) with a load cell of 5 kg, cross-head speed of 1 mm/s, and equipped with a R1.27-cm-diameter cylindrical probe. The maximum force (in g) was determined when the probe penetrated a distance of 4 mm into the gelatin gels. The results of this assay are shown in FIG. 35.

Figure 35:
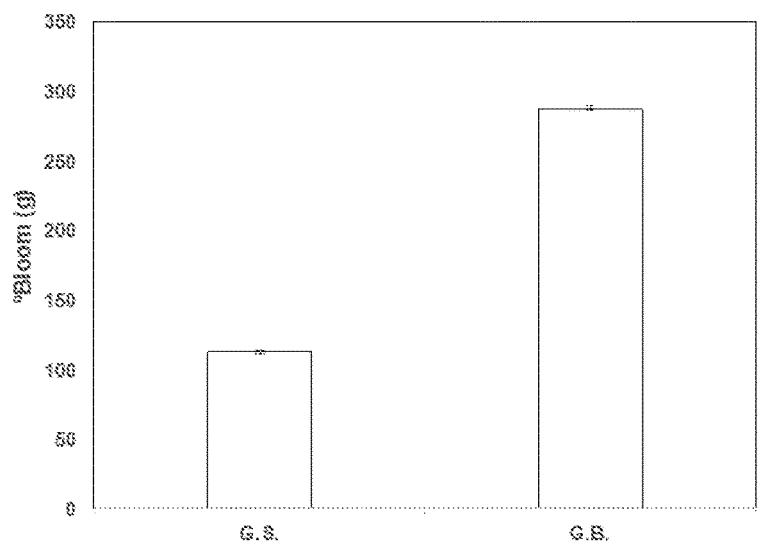
FIG. 35. Gel strength of a non-functionalized salmon gelatin (G.S.) and that of a non-functionalized bovine gelatin (G.B.).

FIG. 35 shows the gel strength measured in salmon gelatin (SG) and bovine gelatin (BG). It is quite evident the significant differences between gelatin obtained from different sources (fish and mammals, respectively) in terms of their gel strength, the gel strength of non-functionalized bovine gelatin being about 2.5-fold higher than that of non-functionalized salmon gelatin. This behavior can be related with the existing difference in molecular weight and amino acid profile of the gelatins. It has been reported in the literature that molecular weight of salmon gelatin is lower than bovine gelatin. On the other hand, glycine and imino acids (proline and hydroxyproline) content is higher in bovine gelatin. Hence, the lower molecular weight and reduced content of certain amino acids (glycine, proline and hydroxyproline) in salmon gelatin may explain a reduced ability to fold helical structures which has a direct impact on the gelatin gel strength.

Figure 38:
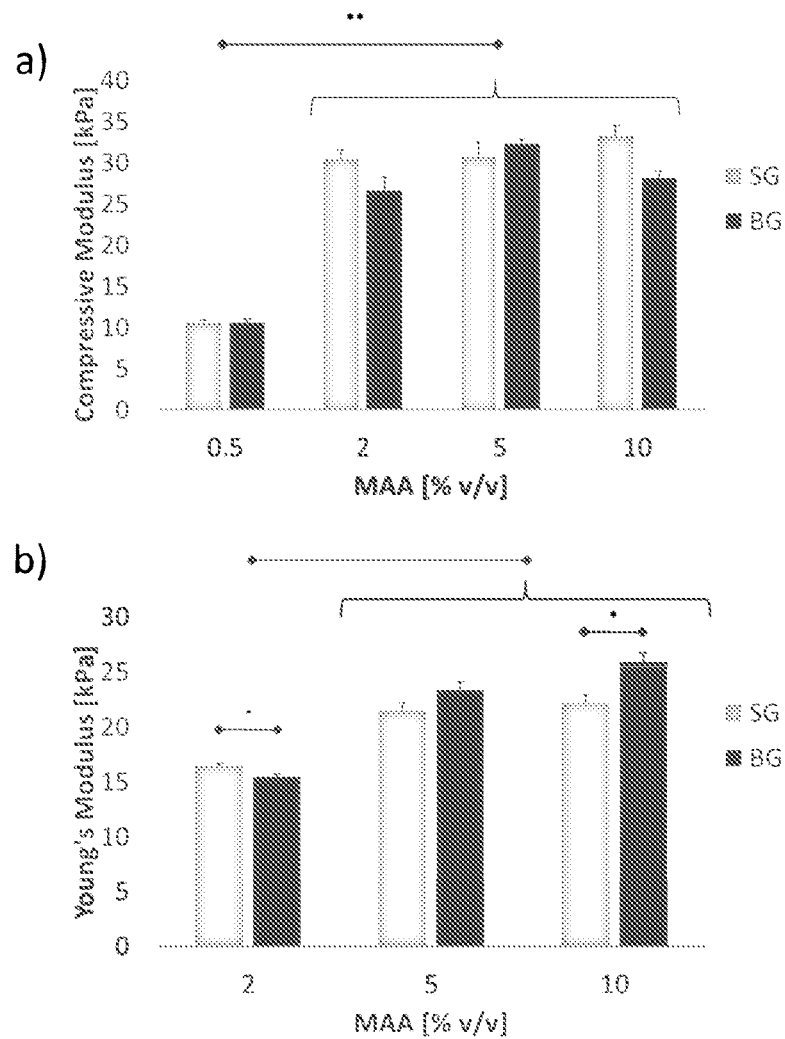
FIG. 38. a) Graphical comparison of the mean compressive moduli of the Salmon and Bovine gelatin derived hydrogels—testing carried out on DMA. b) Graphical comparison of the mean Young's Moduli obtained from a tensile testing of the Salmon and Bovine gelatin derived hydrogels—testing carried out using a mechanical tester. *P<0.05; **P<0.01 (Mann-Whitney), n=5-6.

In view of the much lower initial strength of not cross-linked and not functionalized salmon gelatin with respect to bovine gelatin, the finding that the cross-linking/polymerization of methacrylated fish gelatin results in almost instant polymerization providing a gel with compressive and tensile properties in the same range as those of methacrylated cross-linked bovine gelatin (see FIGS. 19 and 38 as shown herein) was completely unexpected.

Example 7

Additional Characterization of the Methacrylated Salmon and Bovine Gelatin Solutions Rheological Characterization A comparative rheological study of bovine and salmon gelatin substituted and non-substituted with methacryloyl groups was performed in other to project their usability in high precision systems.

Figure 36:
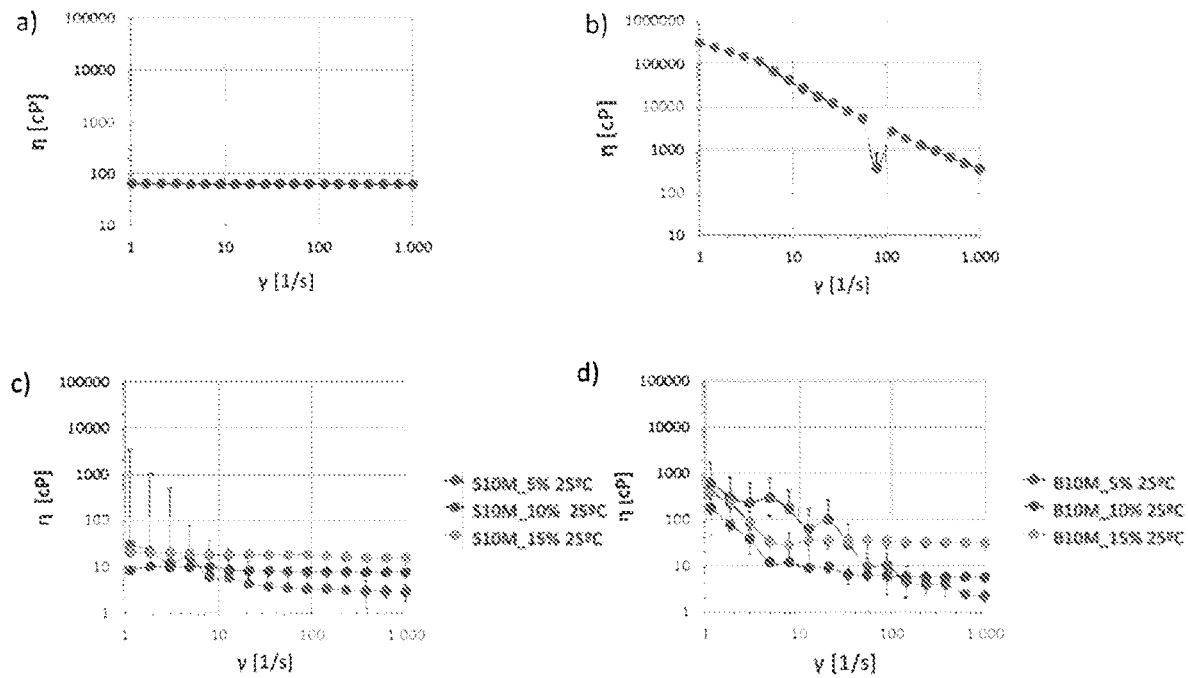
FIG. 36. Viscosity measurement at different shear rate. a) solution of salmon gelatin at 15% [p/v] concentration maintained at 25° C. b) solution of bovine gelatin at 15% [w/v] concentration maintained at 25° C. c) solutions of salmon gelatin functionalized at 90% of lysines with methacryloyl groups, prepared at 3 different concentrations (5%, 10%, 15% [w/v]) and maintained at 25° C. d) solutions of bovine gelatin functionalized at 90% of lysines with methacryloyl groups, prepared at 3 different concentrations (5%, 10%, 15% [w/v]) and maintained at 25° C. Note: In the case of salmon gelatin 90% methacrylation, viscosity was very low, creating imprecise measurements due to sensibility limits in the equipment, specially between 0.1 and 10 s-1. Error bars=SD, n=3 experiments.
Figure 37:
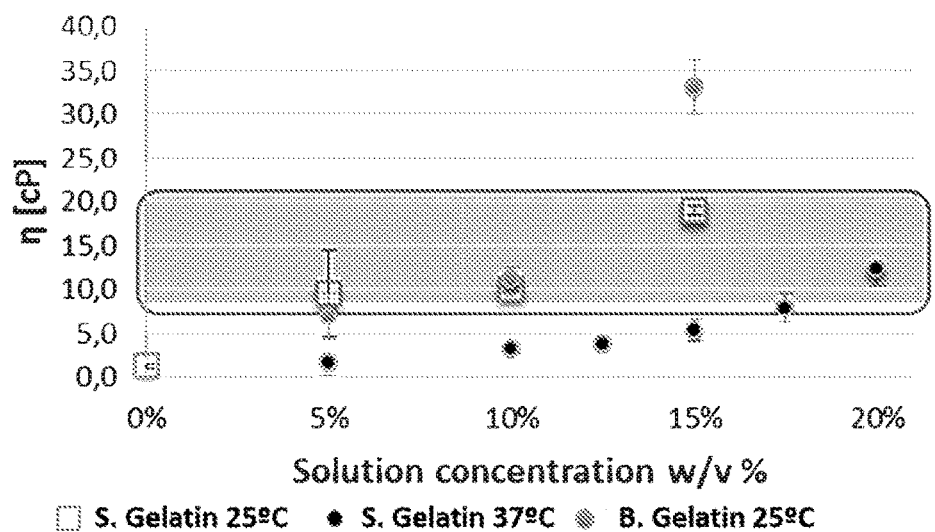
FIG. 37. Summary graph for viscosity measurements at 100 s-1 in shear flow for salmon and bovine gelatin with 90% degree of methacryloyl functionalization at lysine amines Error bars=SD, n=3 experiments.

Viscosity measurements at different shear rate were conducted as described above. The results showed on the one hand a lower viscosity for solutions of non-functionalized and functionalized salmon gel compared to bovine, and on the other a Newtonian behavior for salmon gelatin solutions (functionalized and non-functionalized), while for bovine gelatin solutions a non-Newtonian behavior (see FIG. 36). The non-newtonian behavior is revealed by shear-thinning effects in viscosity for bovine solutions as the shear rate increases, whereas for salmon solutions the viscosity stay unaltered along different levels of shear stress. Newtonian behavior is a strict prerequisite for good jetting or drop formation in drop-on-demand printing and 3D printing systems, which would be another advantage for salmon gelatin in biofabrication uses. Another interesting aspect is that salmon gelatin can performed within the appropriated viscosity range even at concentration of 20% [w/v], which means a broader work range in terms of concentration, hence mechanical properties after crosslinking (see FIG. 37).

Mechanical Characterization

The mechanical properties, measured through dynamic mechanical analysis (DMA), of hydrogels derived from Salmon and Bovine gelatin are in agreement with the o-phtaldialdyde (OPA) primary amine quantification results and previous research (Billiet T. et al., Biomaterials 2014, 35: 49-62), as the compressive modulus increased with de degree of functionalization signifying a positive correlation. Both hydrogels based on Salmon and Bovine gelatin are modified in a reaction using a concentration of 0.5 MAA [% v/v] exhibited a compressive modulus of 11 kPa (10.6±0.7 S.D. kPa and 10.5±0.9 S.D. kPa, respectively) (see FIG. 38a). Salmon gelatin hydrogels at 2 MAA [% v/v] exhibited a compressive modulus of 30.5±2.2 kPa in comparison to 26.6±3.6 kPa for hydrogels derived from Bovine gelatin under the same functionalization condition. Bovine gelatin derived-hydrogels modified through a reaction of 5 MAA [% v/v] showed a similar compressive modulus than hydrogels derived from Salmon gelatin with 32±1.3 kPa to 30.7±4 kPa respectively. Moreover, hydrogels from gelatins modified at 10 MAA [% v/v] displayed an interesting difference, close to significant (p=0.06, Mann-Whitney), as Salmon exhibited an average of 33 kPa whilst hydrogels based on Bovine gelatin at 10 MAA [% v/v] showed a compressive modulus of 28.2±1.7 kPa, which means a reduction considering the 32±1.3 kPa obtained for hydrogels derived from Bovine gelatin at 5 MAA [% v/v], even though the OPA and nuclear magnetic resonance (NMR) results indicated a higher degree of functionalization at 10 MAA [% v/v]. Overall neither hydrogels derived from Salmon nor from Bovine gelatin has managed to outcompete the other in terms of compression mechanical properties.

Neither hydrogels of the Salmon- nor Bovine-derived gelatin generated through reaction at 0.5 MAA [% v/v] were of sufficient integrity to enable tensile testing using the mechanical tester. However, the results obtained from hydrogels generated at reaction conditions between 2 and 10 MAA [% v/v] (see FIG. 38b)) support those obtained by the DMA showing a positive correlation between the degree of functionalization and Young's Modulus.

Furthermore, hydrogels derived from Salmon gelatin reacted at 10 MAA [% v/v] exhibited a Young's modulus of 22.2±1.2 S.D. kPa (a 1 kPa increase from the Salmon hydrogels at 5 MAA [% v/v]) which resulted in a clear positive correlation between the degree of functionalization and Young's modulus. This result was also seen for Bovine gelatin obtained from reactions at 10 MAA [% v/v], in which hydrogels are showing a 3 kPa increase. In general, the small changes in degree of methacryloyl substitution are reflected in the mechanical testing with good correlation, and no differences in mechanical behavior are observed between photo-crosslinked modified gelatin from Salmon and Bovine.

Hydrolysis Evaluation

Figure 39:
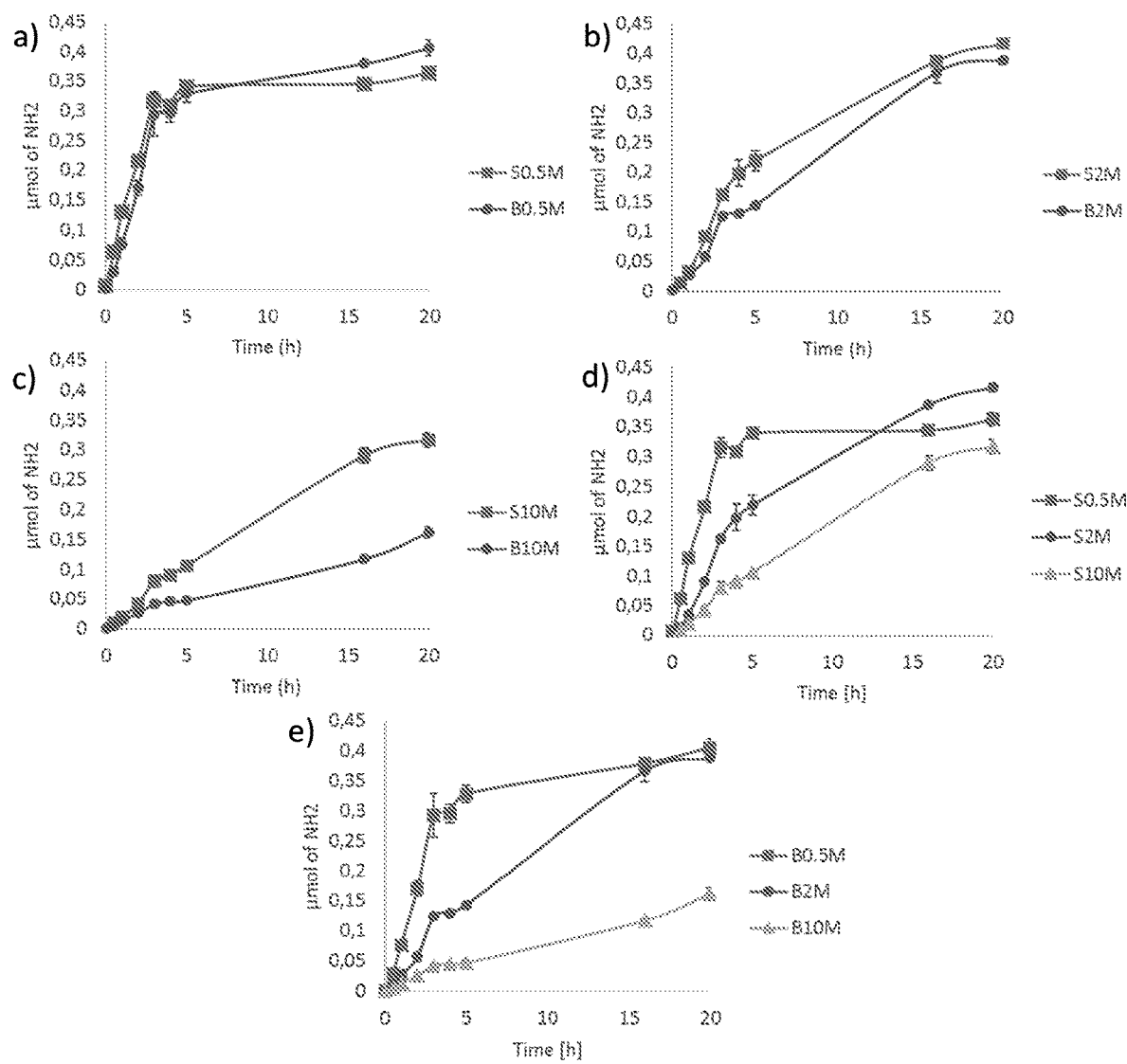
FIG. 39. Progress curves of hydrogels hydrolysis by collagenase type 2. Comparative hydrolysis kinetics between hydrogels derived from gelatin of different sources and similar degree of functionalization (a)-(c). Comparative hydrolysis kinetics between hydrogels derived from the same gelatin source but different degree of functionalization (d)-(e). Hydrolysis reaction were performed in triplicates at 37° C. B2M, B5M, B10M represent hydrogels fabricated with gelatin submitted to functionalization reaction at 0.5, 2 and 10 MAA [% v/v]. B stand for Bovine and S for Salmon. 3 hydrolisis reaction were performed for this experiment. Error bars=S.E.

As seen previously, the degree of methacryloyl functionalization could enhance the mechanical properties of photo-crosslinked hydrogels (see FIG. 38), hence tissue engineering application, where mechanical challenges are expected, could be favored. However, inclusion of bulky groups (methacryloyl) along the aa sequence of gelatin with the concomitant interruption of side chain sequence, could affect the material harboring and hydrolysis at the catalytic side of ECM (extracellular matrix) remodeling enzymes, therefore substrate specificity and catalysis could be compromised. To assess this aspect of biomaterial functionalization, photo-crosslinked hydrogels derived from the two different sources and different degree of methacrylation were subjected to hydrolysis with collagenase type 2. From the hydrolysis kinetics (see FIG. 39), no remarkable differences are observed when comparing salmon and bovine gelatin with similar degree of functionalization, excepting for the hydrogels prepared from gelatins that were submitted to functionalization reaction at 10 MAA [% v/v]. In that case, initial rate of hydrolysis and time to the stationary peak of hydrolysis was faster for salmon gelatin compare to bovine. In relation to degree of methacrylation, there is a decrease in the initial rate of hydrolisis and time to reach the stationary peak when methacryloyl substitution increase. Interestingly, although mechanically hydrogels from salmon and bovine hydrogels showed similar results, salmon gelatin hydrogels, especially at high degree of functionalization, showed faster enzymatic hydrolysis, expecting then faster enzymatic-derived tissue integration when implanted in vivo (faster vascularization, cell invasion and proliferation).

Example 8

Figure 40:
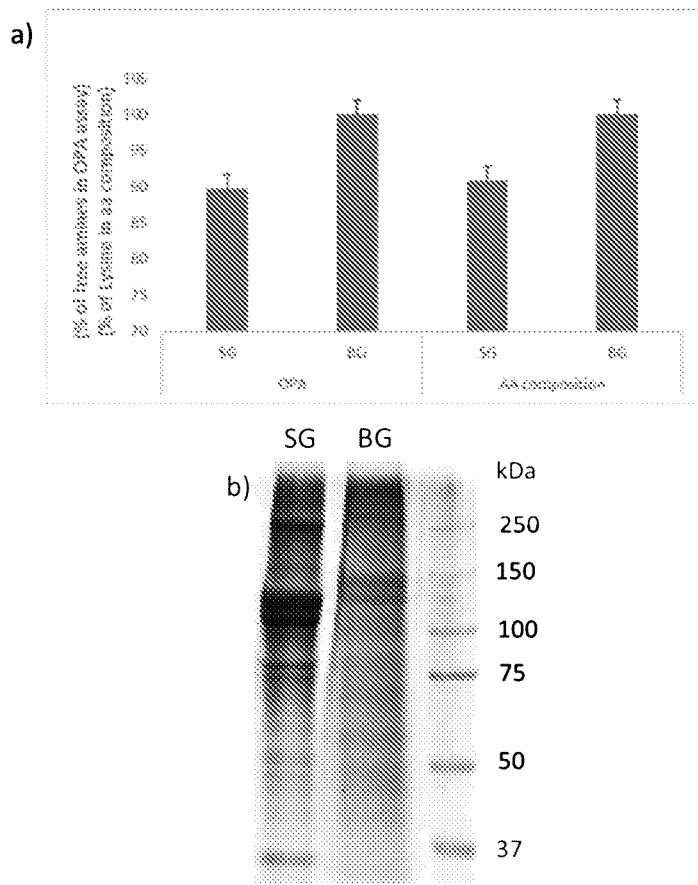
FIG. 40. a) Comparative quantification of free amine in salmon (SG) and bovine gelatin (BG) using the OPA assay and Lysine comparative quantification between SG and BG based on aa composition analysis. b) molecular weights SDS-PAGE analysis of SG and BG polypeptides. Percentage was calculated relative to bovine quantification. AA composition analysis were performed in duplicates and OPA analysis in triplicates.
Figure 41:
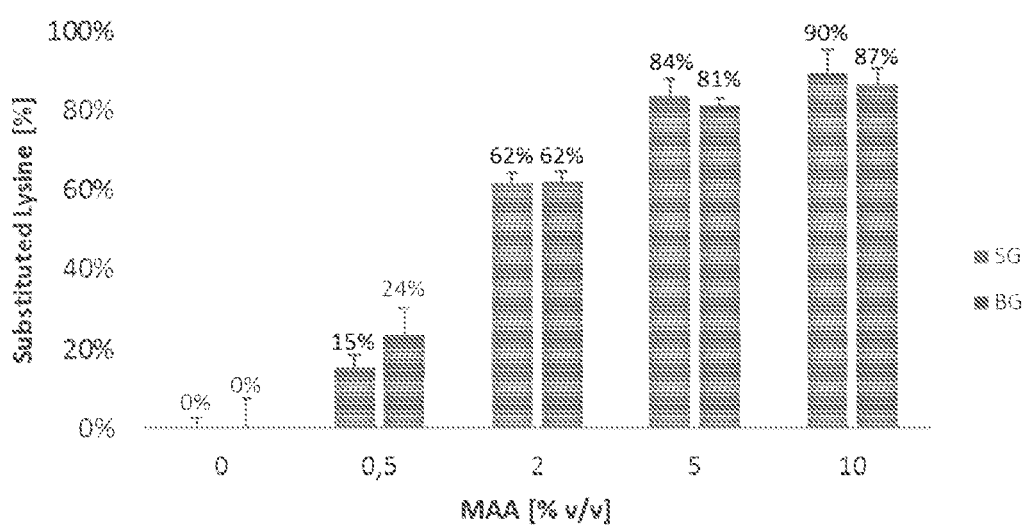
FIG. 41. Quantification of the functionalized lysine based on free amine measurements using the OPA method. Salmon (SG) and Bovine gelatin (BG) was reacted with methacrylic anhydride (MAA) using a 10% gelatin solution supplemented with 0.5, 2, 5 and 10% (v/v) of MAA. Using the same batch of functionalized gelatin, the OPA assay was performed 3 times. Error bars: S.D.

Characterization of the Functionalization of Methacrylated Salmon and Bovine Gelatins The reactive methacrylic anhydride is able to react and bind methacryloyl groups mostly to the free amine groups of lysines when mixture with gelatin under mild conditions (Nichol J W, Biomaterials. 2010, 31(21): 5536-5544). Quantification of remaining free amine groups in reacted methacryloyl gelatine through the o-phthaldialdehyde (OPA) assays (P. M. Nielsen, Journal of Food Science 2001, 66(5): 642-646) would be a reliable methodology to assess the degree of methacrylation or functionalization of gelatin. On the other side, OPA assays and SDS-PAGE analysis of salmon and bovine gelatin are capable to quantify the comparative hydrolysis level and molecular weight approximation, respectively (see FIG. 40). The amino acid composition analysis of Salmon and Bovine gelatin showed slightly higher amount of lysine in the case of bovine gelatin (9% higher number of lysines), which is equivalent to the 9% higher quantification of free amines using the OPA assay; therefore, the level of hydrolysis is equivalent for both extracted gelatins (bovine and salmon). This is deducted since different degree of hydrolysis in the gelatin preparations would result in OPA comparative quantification different from a comparative lysine composition analysis due to the new exposed amine after peptide bonds cleavage. Those quantifications helped us demonstrating that the amount of methacryloyl amine tuning in the different gelatin preparation are comparable between salmon and bovine gelatin, which are stated as a percentage relative to the free amine content in the unreacted salmon and bovine gelatin respectively (see FIG. 41).

Considering the distribution of molecular weight of purified Salmon and Bovine gelatin according to the SDS-PAGE analysis, the equivalent degree of hydrolysis demonstrated by the amine groups quantification and the lysine composition, and the number of functionalized lysine, the number of methacryloyl groups per gelatin monomer would be comparable between Bovine and Salmon gelatins prepared at various degrees of methacryloyl functionalization degree. In this regard, the importance of having comparable samples lies in the fact that differences in in vitro and in vivo assays are explained by the different nature of Salmon and Bovine gelatin (eg. proline and hydroxyproline content) and not due to differences in the molecular weight, hydrolysis degree or number of methacryloyl groups per monomer of polypeptide.

Figure 42:
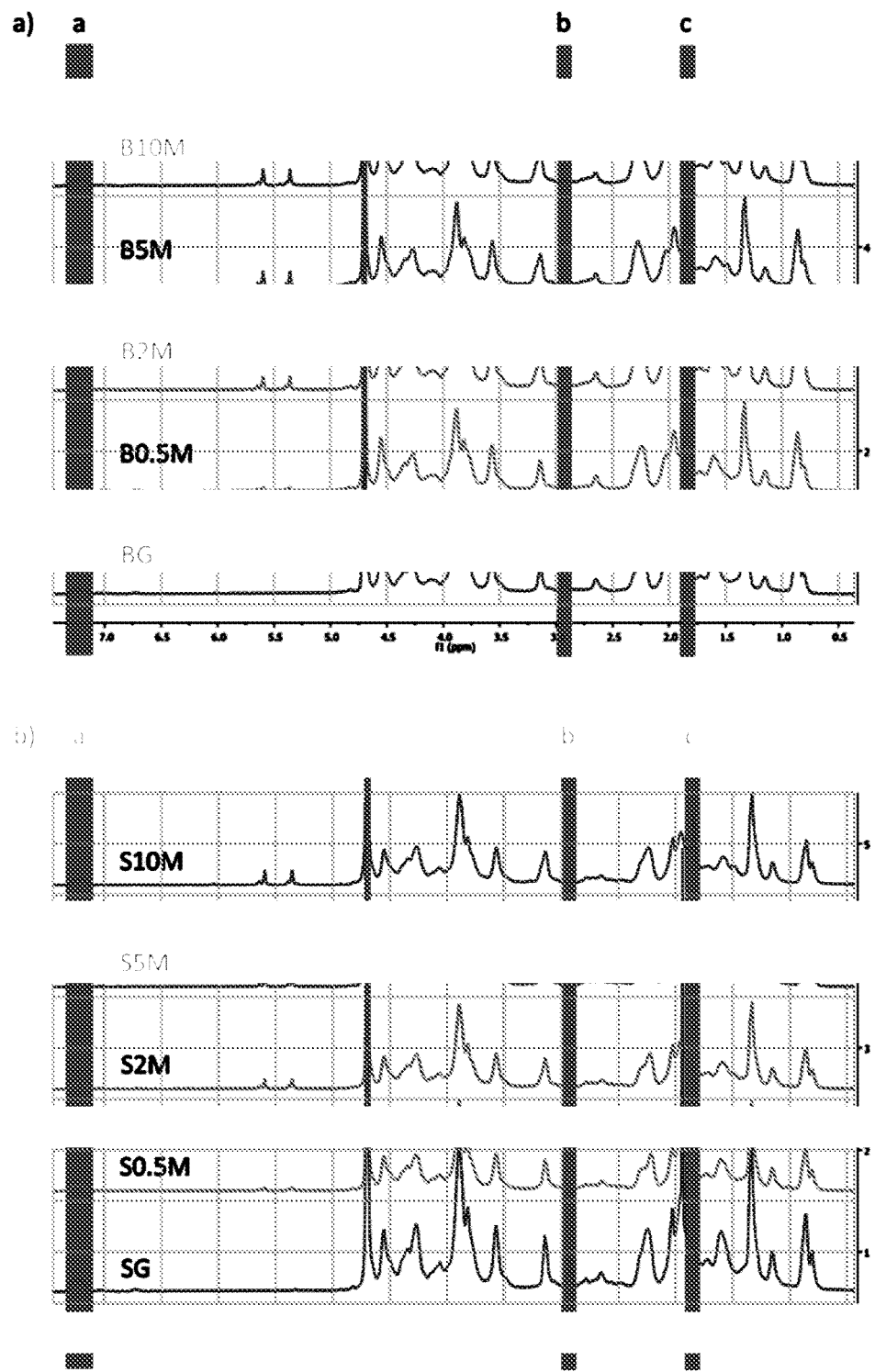
FIG. 42. $^1$H-NMR spectra of bovine (a) and salmon (b) gelatin at different degrees of methacryloyl substitution. Salmon (SG) and Bovine gelatin (BG) were reacted with methacrylic anhydride (MAA) using a 10% gelatin solution supplemented with 0.5 (i.e. S0.5M), 2, 5 and 10% (v/v) of MAA. "a" signals correspond to phenylalanine and was use for normalization of peaks integrals. "b" signals (2.9 ppm.) correspond to lysine methylene and its reduction is associated to lysine functionalization. "c" signals (1.8 ppm.) is related to the presence of the methacryloyl group. For comparative quantification, spectra normalization was performed using the phenylalanine signal (6.9-7.5 ppm, "a" peak in the spectra).
Figure 43:
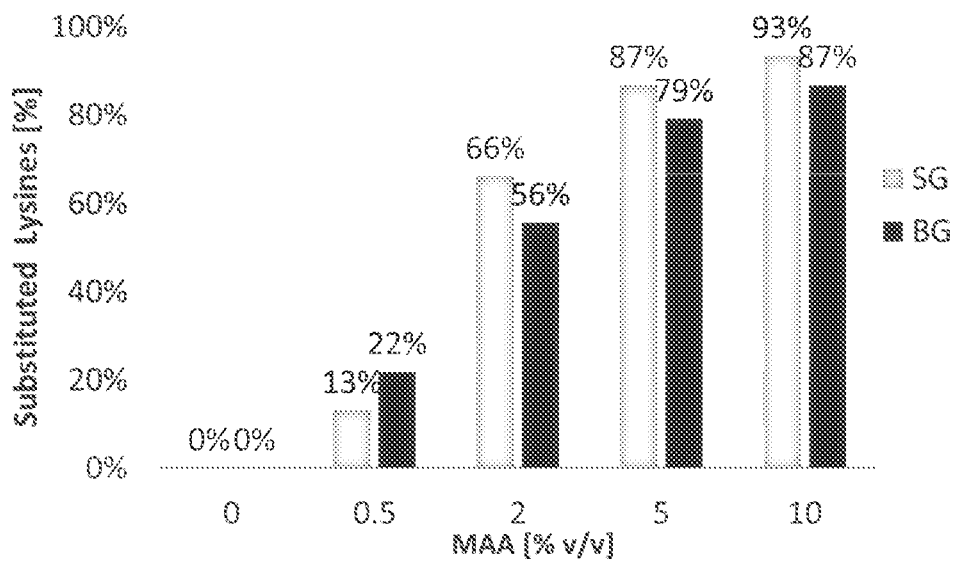
FIG. 43. Quantification of the functionalized lysine based on calculations in the reduction of lysine methylene signals using the $^1$H-NMR spectra of each gelatin preparation. Salmon (SG) and Bovine gelatin (BG) was reacted with methacrylic anhydride (MAA) using a 10% gelatin solution supplemented with 0.5, 2, 5 and 10% (v/v) of MAA. Using the same batch of functionalized gelatins tested in the whole study, the methacrylation degree was obtained from a unique NMR experiment and $^1$H-NMR spectra.

This approach, however, did not provide information if methacryloyl substitution in other less reactive amino acids occurred during the reaction, such as in serine, threonine, tyrosine, asparagine and glutamine. Therefore a second more informative quantitative method based on NMR analysis was carried out to discard the presence of methacryloyl groups in amino acids other than lysine. FIG. 42) shows the spectra obtained for bovine and salmon gelatins at different degree of methacrylation. Comparing non-modified and modified gelatins, and following the analysis of chemical shifts previously reported (J Mater Sci: Mater Med (2012) 23:2607-2617), the new peak observed in the spectra of functionalized gelatins at d=5.4 ppm and d=5.6 ppm was observed differentially amongst gelatin preparation with different degree of methacryloyl substitution. These are generated by the presence of the acrylic protons in the methacryloyl group, while the peak located at d=1.8 ppm. ("c" peak in the spectra) is due to the methyl function of the same added group. On the other hand, the decrease in the shift signal associated to the presence of lysine methylene, located at d=2.9 ppm ("b" peak in the spectra), demonstrates the functionalization of lysine. Other NMR peaks reported previously as possibly methacryloyl transfer at hydroxyl groups (J Mater Sci: Mater Med (2012) 23:2607-2617), were not observed in our gelatin preparations. $^1$H-NMR spectra obtained from non-modified and modified gelatins confirmed similar results compared to OPA assay. (see FIGS. 41 and 43). Under this premise, degrees of methacrylation obtained at the different conditions of reactions are similar between bovine and salmon gelatins.

Example 9

New Formulations Comprising Methacrylated Cold-Fish Gelatins

Example 9.1

Formulations Further Comprising Branched Polyethyleneglycol Derivatives (e.g. Multi-Arm Peg Derivatives)

Figure 44:
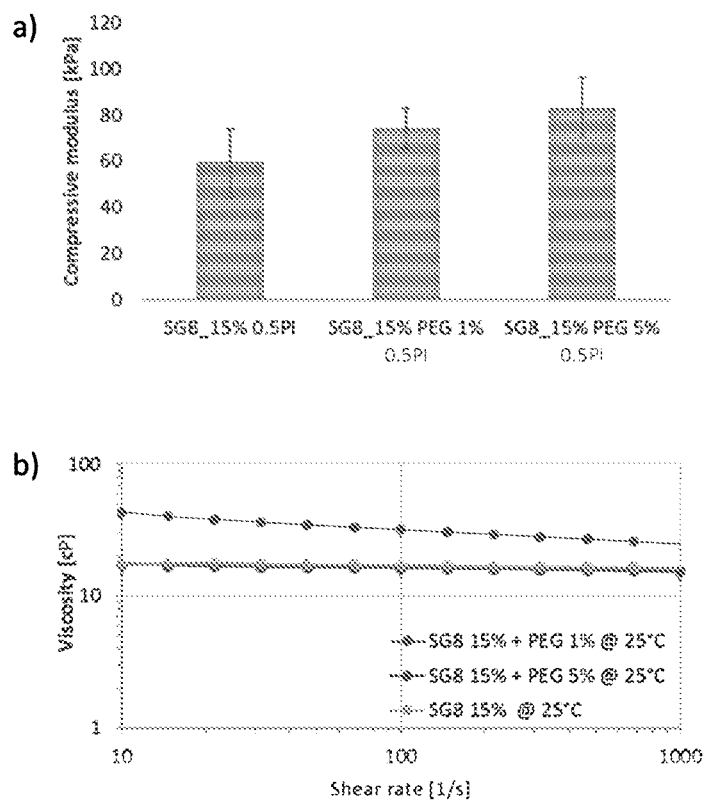
FIG. 44. Mechanical and rheological testing of new formulations. a) Compression testing and b) rheological testing were performed on the crosslinked SG8 formulation (15% [w/v] salmon gelatin functionalized at 90%) supplemented with 1% and 5% [w/w] of 8arm-PEG10K-Acrylate tripentaerythritol.

With the objective of creating new composites with improved crosslinking reactivity, better hygroscopicity (capacity to avoid dehydration) and larger compression and young's modulus, the master formulation SG8 (15% [w/v] salmon gelatin functionalized at 90%) was supplemented with different concentration of a branched poly-linker PEG (8arm-PEG10K-Acrylate tripentaerythritol) and tested for mechanical properties, rheological behavior, reactivity and resistant to dehydration. Increments in the concentration of PEG generated tougher formulations in terms of mechanic's post crosslinking, however the higher concentration of PEG turned the Newtonian formulation into a relatively non-Newtonian and more viscous formulation (see FIG. 44).

Figure 45:
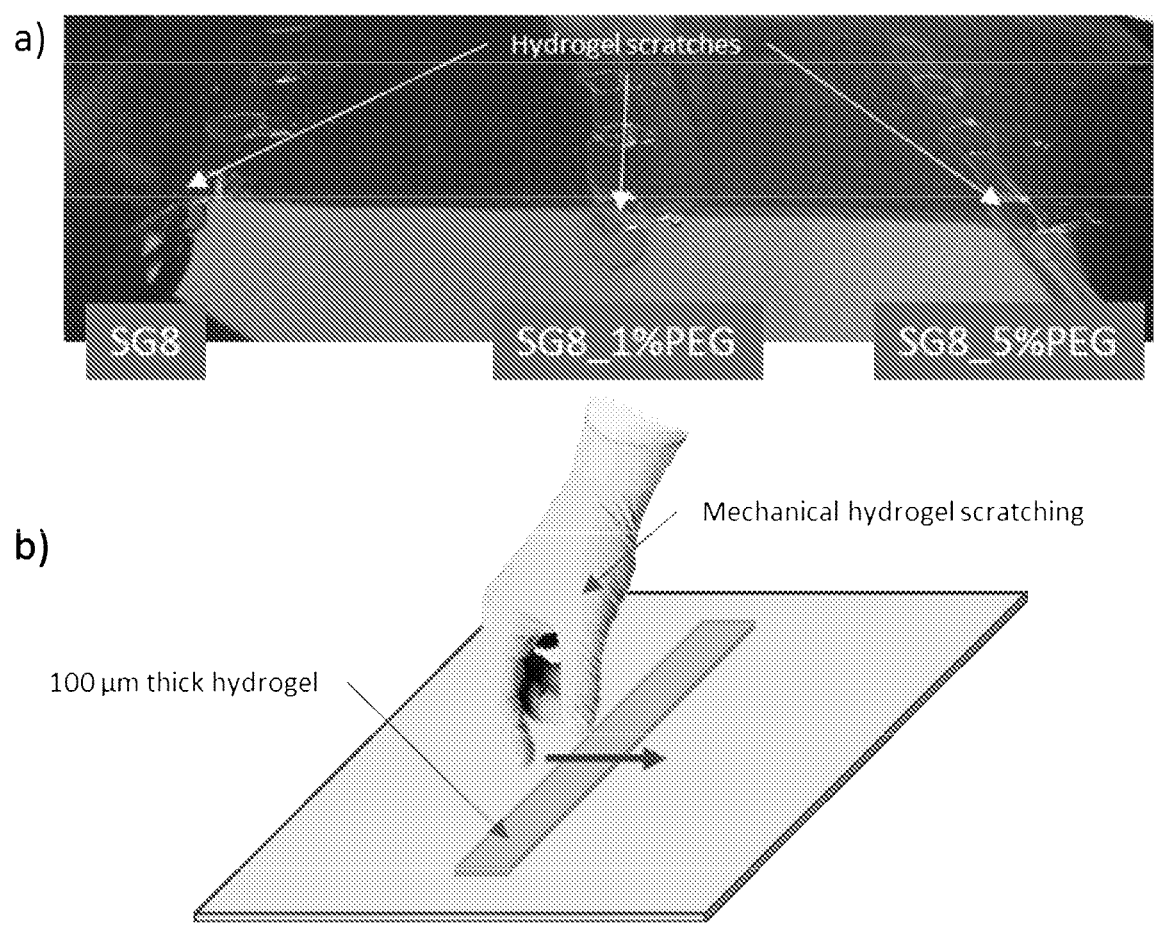
FIG. 45. Manual qualitative testing of crosslinking reactivity and hygroscopicity. a) picture of 100 μm thick hydrogels manually tested for reactivity and hygroscopicity. Reactivity was evaluated by the presence of non-crosslinked hydrogel after 2 and 4 passes of UV light from the printer head. Only liquid solution after mechanical scratching=non-crosslinked; liquid solution and lumpy hydrogels after mechanical scratching=partially crosslinked; Only a substantial hydrogel after mechanical scratching=crosslinked. Hygroscopicity was evaluated by the solution and hydrogel volume being displaced after mechanical scratching. There were 3 levels: hydrated, low hydration and dry, which are characterized approximately by a 50 μl hydrogel volume, 25 μl hydrogel volume and no volume displaced respectively. b) scheme of the scratch or hydrogel displacement protocol.

For reactivity testing, qualitative observations of crosslinked hydrogels were performed after 2 and 4 passes of the UV light from the printer head under normal working conditions (Objet30 3D printer, STRATASYS). The 100 μm height hydrogels based on the solely SG8 formulation were partially crosslinked and dehydrated after 2 passes, and completely dry-out after 4 passes, while the supplementation with 1% [w/w] PEG showed a fairly crosslinked hydrogel after 2 passes without signals of dehydration, however after 4 passes low hydration was observed. SG8 formulation supplemented with 5% [w/w] PEG resist dehydration even after 4 passes, and crosslinking reactivity was further improved (see FIG. 45).

Example 9.2

Formulations Further Comprising Surfactants

Surface Tension Measurements

As mentioned before, good jetting capability of a material in solution preferably has Newtonian fluid behavior, viscosity between 25-10 cP and low surface tension (25-30 mN/m). The SG8 master formulation complies with all the preferred rheological parameters excepting surface tension. We prepared a 15% [w/v] solution of salmon gelatin functionalized at 90% (SG8), which showed a static surface tension of 43 mN/m (see FIG. 46). To lower the surface tension to an appropriated range, different surfactant for water systems were used, BYK-345 (BYK, US), Tivida FL 2300 and Tivida FL 2500 (MERCK, Germany). By only adding small volumes, all surfactants were capable to decrease the static surface tension of the master formulation to 25 mN/m (see FIG. 46).

Figure 46:
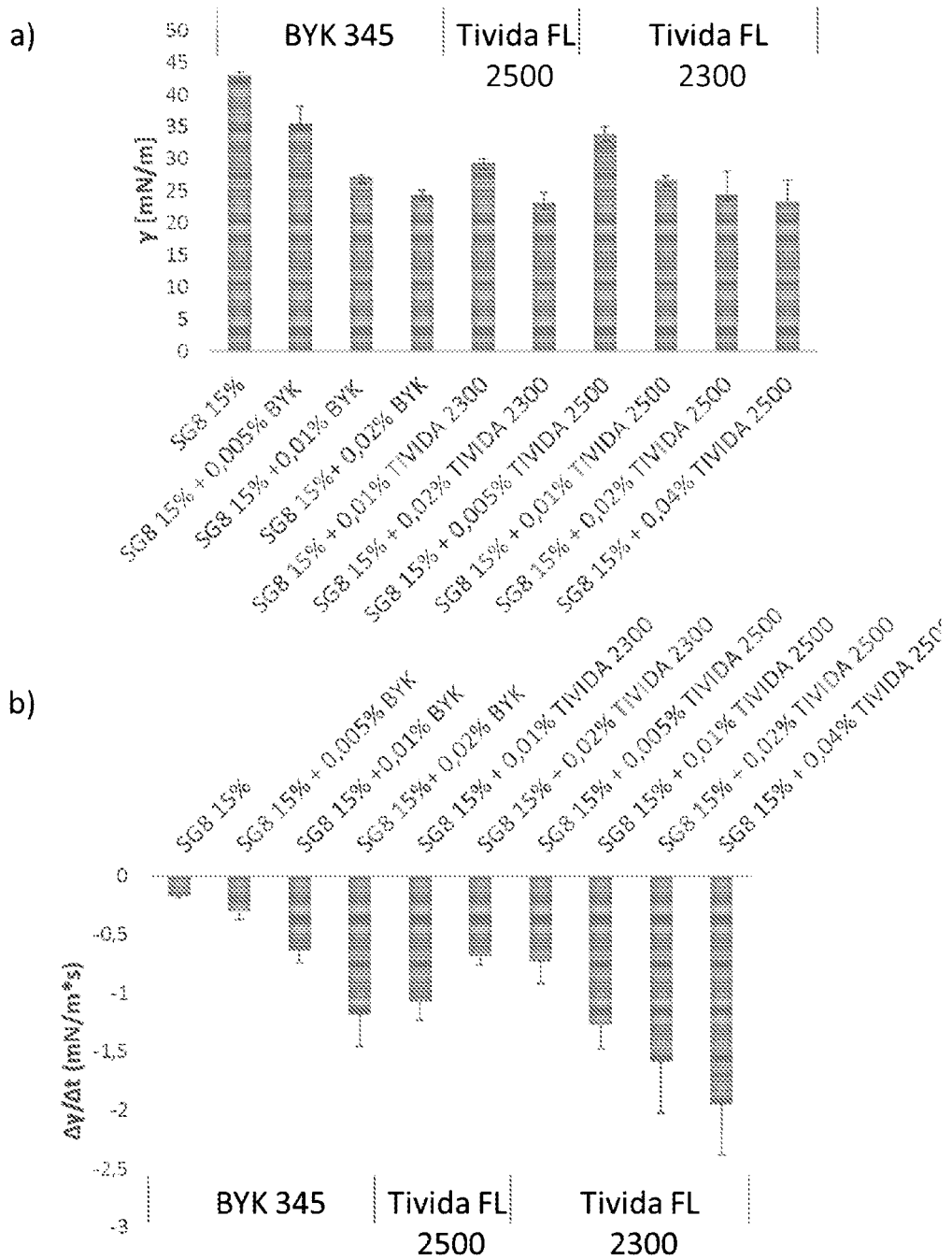
FIG. 46. Surface tension of the master formulation (15% [w/v] solution of salmon gelatin functionalized at 90% (SG8)) supplemented with different types and quantities of surfactant. Concentration of modified salmon gelatin and surfactants are expressed as w/v % and v/v % respectively. Error bars=SD, n=3 experiments. Results are presented as the a) static surface tension after 300 s of equilibrium and b) derivative of the dynamic surface tension.

Since most liquids are usually handled under circulating conditions, it is important to report the time variation component of the surface tension (see FIG. 46). This component varies depending on the concentration and nature of the surfactant. In this regard, surfactant with shorter times for equilibrium are more efficient in lowering the surface tension during pL drop formation. Taking into account the static surface tension, and the time requires to reach equilibrium, Tivida FL2300 at 0.02% [v/v] concentration and BYK 345 at 0.02% appear as the most promising surfactants conditions to be used for pL drop formation in an inkjet system.

Cell Viability and Cell Compatibility Determinations

In order to verify cell viability and cell compatibility of the new complex formulations, Hydrogel based on this formulation were fabricated with encapsulated cells.

An already known phenomenon, describing that transglutaminase-crosslinked gelatin gel in which cells are encapsulated, cells at a distance longer than 100 um from the hydrogel surface, their proliferative profile is reduced drastically (PLoS One. 2014 Aug. 18; 9(8):e105616). Deducted limitation of nutrients, oxygen and metabolites diffusion and exchange for cells at an even longer distances, would presume important effects in their viability too.

Figure 47:
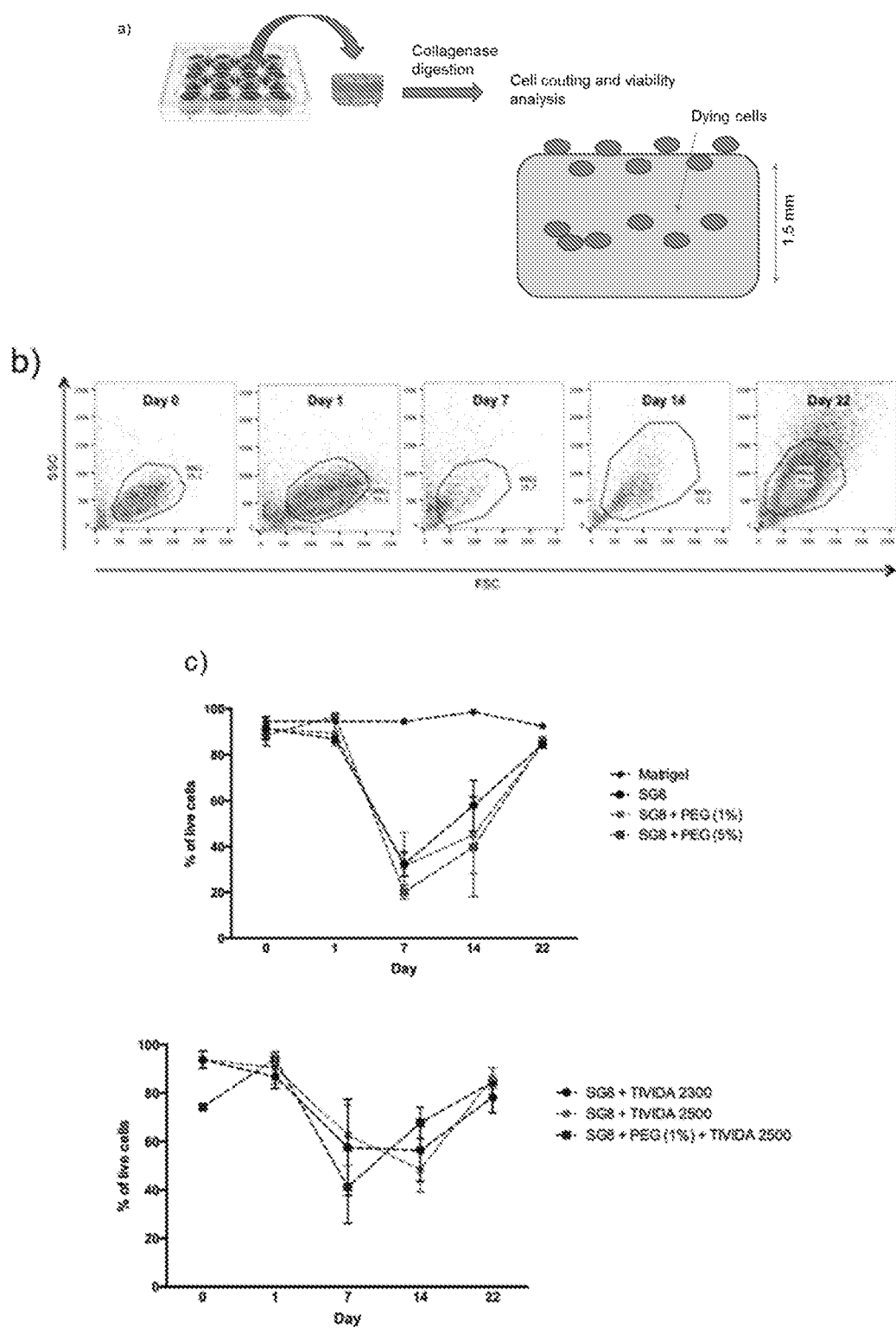
FIG. 47. Cell viability for encapsulated cells in hydrogels based on the new formulation.

Similar conditions were tested with our new formulations, in which cells ($2 \times 10^6$ cells/mL) were encapsulated in a hydrogel 1.5 mm height and 8 mm in diameter. After different times interval (0, 1, 7, 14, 21 days), encapsulated cells were recover from hydrogels (FIG. 47*a*), counted (FIG. 47*b*) and viability tested (FIG. 47*c*). As expected, number of recovered cells diminished until day 7, possibly due to cells death of encapsulated cells deep in the hydrogel. After day 7, cells number increases again, possibly due to cells proliferation of encapsulated cells close to the hydrogel surface.

Interestingly, and non-expected, hydrogel formulation in presence of surfactant TIVIDA 2300 and TIVIDA 2500, reduces the cell death observed at day 7, while surfactant BYK-345 killed all the cells, most likely because of its particular chemistry affecting the integrity of cells membrane. In the case of TIVIDA 2300 and TIVIDA 2500, cell viability was much higher, even higher than the control of hydrogel based on modify salmon gelatin alone. It is possibly that this better cell viability is correlated to a higher diffusion coefficient of nutrients, metabolites and gases within the hydrogel due to presence of fluorosurfactants (TIVIDA 2300, TIVIDA 2500).

Example 10

Extraction of Salmon Gelatin at Different pHs

Salmon gelatin was extracted from Atlantic salmon (*Salmo salar*) skins following the protocol previously explained. Briefly, after pre-treatments which included cleaning for eliminate residues of muscle and scales and a series of treatments with 0.1 M solution NaOH and 0.05 M acetic acid solution, the salmon gelatin extraction was carried out under different pH (3, 4 and 5) at 60° C. during 3.5 h. The supernatant liquid was vacuum filtered (22 mm) and dried in oven at 55° C. during 24 h. The dried gelatin obtained was grounded and stored at 5° C. until further use.

Salmon gelatins obtained at different pH conditions, were characterized in terms of their biochemical properties (proximate composition, molecular weight and aminoacid profile) and physical properties, specifically gel strength, thermal and rheological properties and molecular configuration by Raman spectroscopy.

Biochemical Properties Characterization

Figure 48:
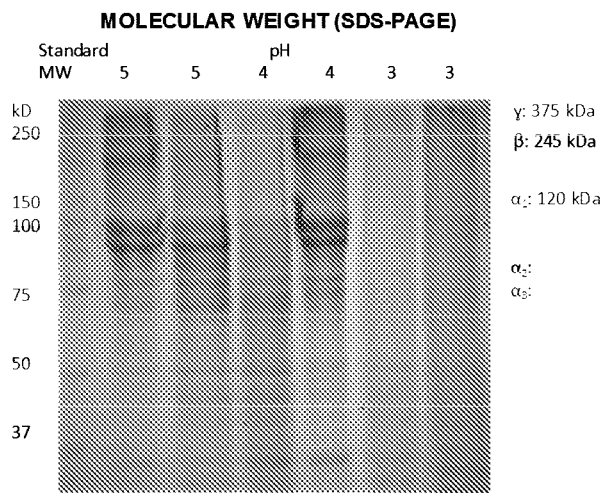
FIG. 48. Electrophoresis SDS-PAGE for salmon gelatin extracted at different pH conditions.

Regarding with biochemical properties, proximate composition was tested using methods described and validated by AOAC (2015) and used previously in gelatin characterization (Journal of the Science of Foods and Agriculture 91(2011):2558-2565, Food Hydrocolloids 71(2017):118-128). Molecular weight was determined by SDS-PAGE electrophoresis and aminoacid profile was determined by HPLC (Journal of the Science of Foods and Agriculture 91(2011):2558-2565, Food Hydrocolloids 71(2017):118-128). Results showed that in term of proximate composition, extracting gelatin at different conditions of pH does not affect significantly the macronutrients composition (Table 2. Significant differences in protein content (around 99% dry basis in all gelatin tested) and ash content (around 0.6% dry basis) were not detected, whereas fat content was below the detection limit of method used and non-nitrogenous fraction was also non-detected. On the other hand, aminoacid composition did not showed significant differences attributable to pH extraction. The content of most important aminoacid for gelatin stability (glycine, proline and hydroxyproline) was not influenced by pH extraction (Table 2). However, the molecular weight evaluated by SDS-PAGE electrophoresis showed that pH extraction is a key-value for determining the molecular weight of gelatin strands due to as lower pH used for extraction higher is the molecular weight distribution on the electrophoresis gel, because of the higher hydrolysis conditions taking place at lower pH. Thus, gelatin extracted at pH 5 showed clearly molecular weight bands situated around 120 kDa which most possibly correspond to α-helix, and other bands around 250 kDa related with more complex gelatin strands (e.g. β-helix) (FIG. 48). But, gelatin extracted at pH 3 shows molecular weight bands distributed between 37 and 100 kDa, depicting the higher hydrolytic conditions promoted at lower pH value (FIG. 48).

TABLE 2

Proximate composition and aminoacid content for salmon gelatin obtained at different pHs.

| | pH | | |
|---|---|---|---|
| | 3.0 | 4.0 | 5.0 |
| Moisture (% ww) | 11.5 | 5.4 | 3.7 |
| Protein (% dw) | 99.4 | 99.4 | 99.5 |
| Non-nitrogenous Extract | 0.0 | 0.0 | 0.0 |

TABLE 2-continued

Proximate composition and aminoacid content
for salmon gelatin obtained at different pHs.

| | pH | | |
|---|---|---|---|
| | 3.0 | 4.0 | 5.0 |
| Lipid (% dw) | ND+ | ND+ | ND+ |
| Ash (% dw) | 0.6 | 0.6 | 0.5 |
| Glycine (mg/100 g protein) | 24.56 (3.27)* | 25.26 (1.03) | 26.68 (1.57) |
| Proline (mg/100 g protein) | 10.95 (1.29) | 11.60 (0.14) | 12.24 (0.32) |
| Hydroxyproline (mg/100 g protein) | 8.24 (0.47) | 8.60 (0.02) | 8.81 (0.10) |

*values in brackets correspond to standard deviation

Physical Properties Characterization

Figure 49:
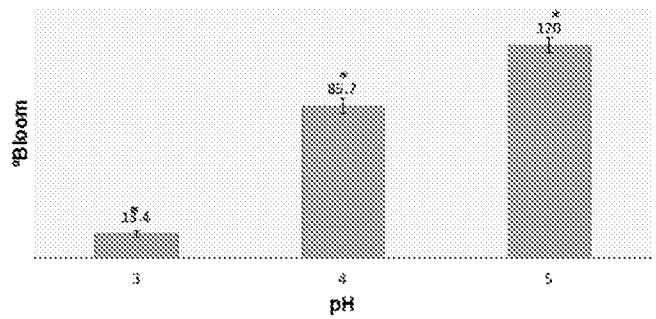
FIG. 49. Gel strength (Bloom, g) for salmon gelatin extracted at different pH conditions.

In terms of physical properties characterization, the pH extraction showed a strong effect on gel strength (FIG. 49). Thus, highest pH extraction tested (pH 5) had higher gel strength and the lowest pH tested (pH 3) showed lower gel strength, which is consistent with higher molecular weight showed by gelatin extracted at pH 5 assessed by SDS-PAGE. This behavior has been related with higher capacity of gelatin with high molecular weight to form higher amount of helical structures (Biomaterials 25(2004):5675-5680). The behavior described by gel strength results is directly correlated with thermal parameters of gelatin extracted at different pHs. Thermal properties were studied by Differential Scanning calorimetry (DCS) applying a temperature scan from 70° C. to −5° C. at 10° C./min and evaluating the temperature at which occur the exothermal transition related with helical structure formation (gelling point) from random gelatin strands. DSC data shows that higher energy (enthalpy) is involved in gel formation from gelatin extracted at pH 5, and less energy is involved in gel formation with gelatin obtained at pH 3 (Table 3). Thus, salmon gelatin extracted at pH 5 has higher molecular weight which produces stronger gelatin gels which implies using higher energy to promote the gelatin folding. Otherwise, the transition temperature is also correlated with cited parameters, where in higher molecular weight gelatin the transition takes place at certain temperature and along the molecular weight is decreasing the transition temperature is shifting to lower values (Table 3).

Figure 50:
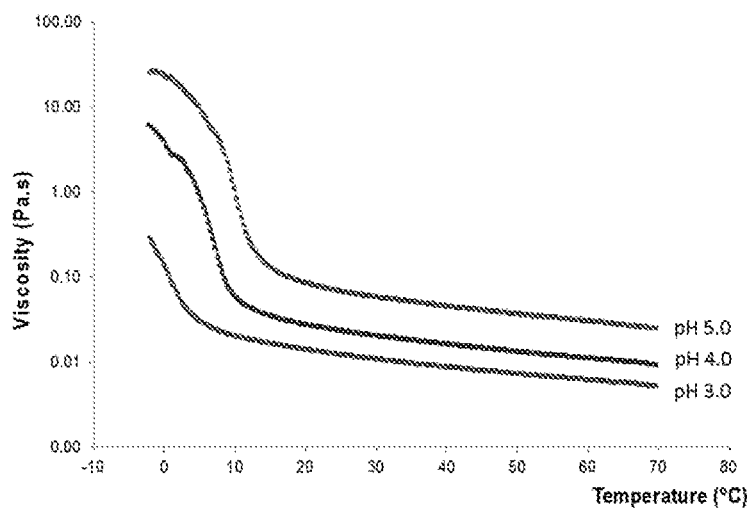
FIG. 50. Viscosity as a function of temperature (tested by flow temperature ramp) for salmon gelatin extracted at different pH conditions.

With respect to rheological characterization of salmon gelatin obtained at different pHs, the results obtained are also directly correlated with results previously showed. FIG. 50 shows the viscosity behavior of salmon gelatin samples tested as a function of temperature (flow temperature ramp). Is quite evident the effect of molecular weight of gelatin strands on viscosity behavior, where gelatin extracted at pH 5 showed the higher viscosity in all the temperature range tested, while the opposite was observed in gelatin extracted at pH 3. These results are also highlighting that gelatin strands with higher molecular weight and able to form higher amount of helical structures (higher gel strength), promote higher flux resistance and show higher viscosity. For instance, at 4° C. the viscosity values obtained were 0.035, 1.477 and 12.50 Pa·s for gelatin extracted at pH 3, 4 and 5, respectively. Through rheological analysis is also possible to evaluate the gelling point of gelatin, by reading the intersection point between modulus G' and G" (data not showed). Thus, interestingly the gelling point recorded by rheology are consistent with those gelling points recorded previously by DSC (Table 3).

TABLE 3

Thermal and rheological parameters for salmon
gelatin obtained at different pHs.

| pH | T gelling (° C.) - DSC | ΔH (Jg$^{-1}$)(db) - DSC | T gelling (° C.) - Rheology |
|---|---|---|---|
| 3.0 | 3.6 (0.3)*a | −2.3 (0.5)$^a$ | 3.0$^a$ |
| 4.0 | 9.4 (0.5)b** | −6.7 (1.1)$^b$ | 7.0$^b$ |
| 5.0 | 10.6 (0.3)c | −8.6 (1.1)$^c$ | 10.5$^c$ |

*values in brackets correspond to standard deviation
**different letters in same column represent significant differences (p < 0.05)

Figure 51:
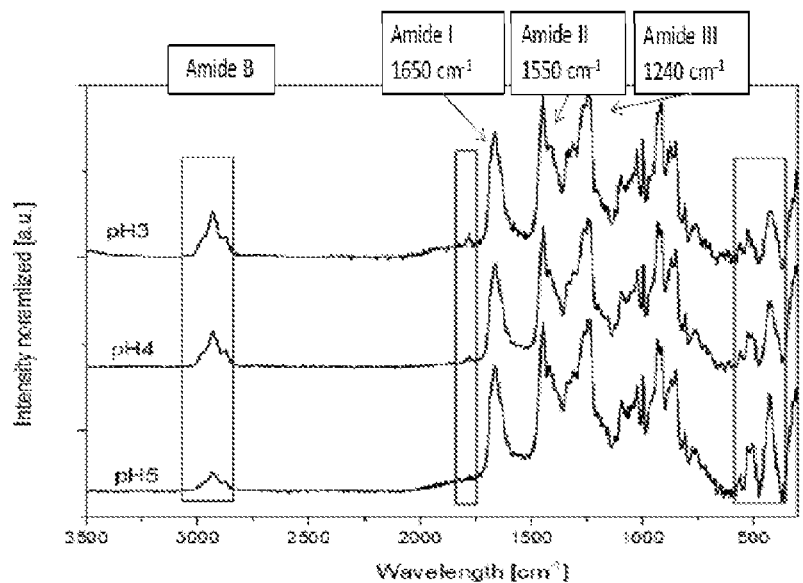
FIG. 51. Raman spectra for salmon gelatin extracted at different pH conditions.

Finally, the analysis of molecular configuration by Raman spectroscopy also shows results close related with later analysis. The Raman spectra are showed in FIG. 51. Raman spectra obtained to gelatin extracted at different pHs are the expected spectra for this kind of proteins. For example, different groups Amide I, II and III were detected at Raman shift reported for these group in literature (1650 cm$^{-1}$, 1550 cm$^{-1}$ and 1240 cm$^{-1}$, respectively). Interesting is the behavior showed by Amide B group, which peak shows an increase in intensity when the pH of extraction is decreasing. Amide B group is related with hydroxyl group situated at the terminal zone of protein backbone, and in this case, is suggesting the presence of higher number of molecules with hydroxyl group at N-terminal. This behavior is consistent with more hydrolyzed gelatin chains obtained at pH 3 due to the hydrolytic effect of low pH. Thus, the Raman spectra results are compatible with SDS-PAGE results and consistent with gel strength and thermal and rheological properties.

The invention claimed is:

1. A composition comprising a solution, which in turn comprises an amino acid chain gelatin polymer derived from the genus *Salmo* or *Oncorhynchus* comprising a proline and a hydroxyproline content of 20% or less with respect to the total amino acid content at a concentration from 1% to 20% (w/v) and a photoinitiator, wherein side chains of the amino acid chain gelatin polymer are chemically functionalized with methacryloyl groups or acryloyl groups to become reactive to photocrosslinking in the presence of free radicals, and wherein the solution has a viscosity lower than 25 centipoises and shows Newtonian behavior.

2. The composition of claim 1, wherein the solution comprises the amino acid chain gelatin polymer at a concentration from 5% to 20% (w/v).

3. The composition of claim 1, wherein the side chains are functionalized with methacryloyl groups.

4. The composition of claim 1, wherein the degree of functionalization of the amino acid side chains of the gelatin polymer with said chemical agent is from 30% to 100% of lysine residues of the amino acid chain gelatin polymer.

5. The composition of claim 1, wherein said solution is pre-treated at temperatures between 1° C. and 12° C. to induce gelling prior to inducing covalent crosslinking of the groups reactive to photocrosslinking in the presence of free radicals.

6. A process to manufacture a composition comprising a solution, which in turn comprises an amino acid chain gelatin polymer comprising a proline and a hydroxyproline content of 20% or less with respect to the total amino acid content wherein the amino acid chain gelatin polymer is from the genus *Salmo* or *Oncorhynchus*, at a concentration from 1% to 20% (w/v), which optionally further comprises a photoinitiator, and wherein the amino acid chain gelatin polymer is chemically functionalized with a chemical agent selected from the group consisting of methacryloyl groups or acryloyl groups to become reactive to photocrosslinking in the presence of free radicals, wherein the solution has a viscosity lower than 25 centipoises and shows Newtonian behavior, comprising the following steps:
- a) Obtaining an amino acid chain gelatin polymer comprising a proline and a hydroxyproline content of 20% or less with respect to the total amino acid content, wherein the amino acid chain gelatin polymer is from the genus *Salmo* or Onchorhynchus, and dissolving it in solvent, to a final concentration between 1% and 20% (w/v);
- b) Chemically modifying the primary structure of the amino acid chain gelatin polymer of step a), by adding methacrylic anhydride to the solution of step a);
- c) Removing all unreacted methacrylic anhydride from the solution of step b);
- d) Optionally adding a radical-derived photoinitiator or a surfactant, or both; and
- e) optionally filtering and freeze drying the resultant composition from step c) or d), if applicable.

7. A scaffold, bead, engineered tissue, engineered device or micro-device, comprising the composition of claim 1.

8. A food product comprising the composition of claim 1.

9. The method of claim 6, wherein the amino acid chain gelatin polymer is at a concentration from 5 to 20% (w/v).

10. The composition of claim 1, wherein after the polymerization or crosslinking the solution forms a hydrogel with a compressive modulus between 25-100 kPa.

* * * * *